(12) United States Patent
Lohray et al.

(10) Patent No.: US 7,348,426 B1
(45) Date of Patent: *Mar. 25, 2008

(54) SUBSTITUTED BICYCLIC HETEROCYCLES, PROCESS FOR THEIR PREPARATION AND THEIR USE AS ANTIOBESITY AND HYPOCHOLESTEROLEMIC AGENTS

(75) Inventors: Braj Bhushan Lohray, Hyderabad (IN); Vidya Bhushan Lohray, Hyderabad (IN); Ashok Channaveerappa Bajji, Salt Lake City, UT (US); Shivaramayya Kalchar, Taipei (TW); Ranga Madhavan Gurram, Hyderabad (IN); Ramanujam Rajagopalan, Hyderabad (IN); Chakrabarti Ranjan, Hyderabad (IN)

(73) Assignees: Dr. Reddy's Laboraties Limited, Hyderabad (IN); Dr. Reddy's Research Foundation, Hyderabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 09/959,093

(22) PCT Filed: Apr. 25, 2000

(86) PCT No.: PCT/IB00/00501

§ 371 (c)(1),
(2), (4) Date: Jul. 1, 2004

(87) PCT Pub. No.: WO00/66572

PCT Pub. Date: Nov. 9, 2000

(30) Foreign Application Priority Data

Apr. 28, 1999 (IN) .............................. 484/MAS/99

(51) Int. Cl.
*A61K 31/538* (2006.01)
*C07D 265/36* (2006.01)
*C07D 279/16* (2006.01)
*A61P 3/06* (2006.01)

(52) U.S. Cl. ............................. 544/51; 544/52; 544/4
(58) Field of Classification Search ............... 544/51, 544/52, 4
See application file for complete search history.

(56) References Cited

U.S. PATENT DOCUMENTS 5,104,888 A 4/1992 Yoshioka et al. ........... 514/369

6,809,095 B2 * 10/2004 Lohray et al. ........... 514/228.2

FOREIGN PATENT DOCUMENTS

| JP | 09012575 | 1/1997 |
|---|---|---|
| WO | 9210468 | 6/1992 |
| WO | 9413650 | 6/1994 |
| WO | 9604260 | 2/1996 |
| WO | 9725042 | 7/1997 |
| WO | 9728149 | 8/1997 |
| WO | 9731907 | 9/1997 |
| WO | 9736579 | 10/1997 |
| WO | 9802159 | 1/1998 |
| WO | 9920614 | 4/1999 |

OTHER PUBLICATIONS

Patent Abstracts of Japan Publication No. 09012575 dated Jan. 14, 1997.

* cited by examiner

*Primary Examiner*—Kahsay Habte
(74) *Attorney, Agent, or Firm*—Dority & Manning, Inc.

(57) ABSTRACT

The present invention relates to novel antiobesity and hypocholesterolemic compounds, their derivatives, their analogs, their tautomeric forms, their stereoisomers, their polymorphs, their pharmaceutically acceptable salts, their pharmaceutically acceptable solvates and pharmaceutically acceptable compositions containing them. More particularly, the present invention relates to novel β-aryl-α-oxysubstituted alkylcarboxylic acids of general formula (I), their derivatives, their analogs, their tautomeric forms, their stereoisomers, their polymorphs, their pharmaceutically acceptable salts, their pharmaceutically acceptable solvates and pharmaceutically acceptable compositions containing them (I)

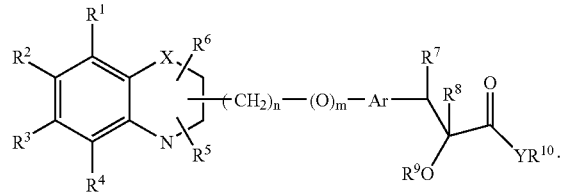

5 Claims, No Drawings

SUBSTITUTED BICYCLIC HETEROCYCLES, PROCESS FOR THEIR PREPARATION AND THEIR USE AS ANTIOBESITY AND HYPOCHOLESTEROLEMIC AGENTS

FIELD OF THE INVENTION

The present invention relates to novel antiobesity and hypocholesterolemic compounds, their derivatives, their analogs, their tautomeric forms, their stereoisomers, their polymorphs, their pharmaceutically acceptable salts, their pharmaceutically acceptable solvates and pharmaceutically acceptable compositions containing them. More particularly, the present invention relates to novel β-aryl-α-oxysubstituted alkylcarboxylic acids of the general formula (I), their derivatives, their analogs, their tautomeric forms, their stereoisomers, their polymorphs, their pharmaceutically acceptable salts, their pharmaceutically acceptable solvates and pharmaceutically acceptable compositions containing them.

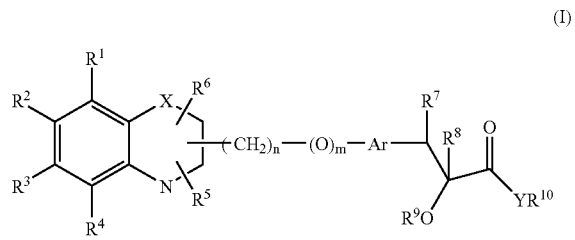

(I)

The present invention also relates to a process for the preparation of the above said novel compounds, their analogs, their derivatives, their tautomeric forms, their stereoisomers, their polymorphs, their pharmaceutically acceptable salts, pharmaceutically acceptable solvates and pharmaceutical compositions containing them.

The present invention also relates to novel intermediates, processes for their preparation and their use in the preparation of compounds of formula (I).

The compounds of the present invention lower total cholesterol (TC), increase high density lipoprotein (HDL) and decrease low density lipoprotein (LDL), which have a beneficial effect on coronary heart disease and atherosclerosis.

The compounds of general formula (I) are useful in reducing body weight and for the treatment and/or prophylaxis of diseases such as hypertension, coronary heart disease, atherosclerosis, stroke, peripheral vascular diseases and related disorders. These compounds are useful for the treatment of familial hypercholesterolemia, hypertriglyceridemia, lowering of atherogenic lipoproteins, VLDL (very low density lipoprotein) and LDL. The compounds of the present invention can be used for the treatment of certain renal diseases including glomerulonephritis, glomerulosclerosis, nephrotic syndrome, hypertensive nephrosclerosis and nephropathy. The compounds of general formula (I) are also useful for the treatment and/or prophylaxis of insulin resistance (type II diabetes), leptin resistance, impaired glucose tolerance, dyslipidemia, disorders related to syndrome X such as hypertension, obesity, insulin resistance, coronary heart disease and other cardiovascular disorders. These compounds may also be useful as aldose reductase inhibitors, for improving cognitive functions in dementia, treating diabetic complications, disorders related to endothelial cell activation, psoriasis, polycystic ovarian syndrome (PCOS), inflammatory bowel diseases, osteoporosis, myotonic dystrophy, pancreatitis, arteriosclerosis, retinopathy, xanthoma, inflammation and for the treatment of cancer. The compounds of the present invention are useful in the treatment and/or prophylaxis of the above said diseases in combination/concomitant with one or more HMG CoA reductase inhibitors, hypolipidemic/hypolipoproteinemic agents such as fibric acid derivatives, nicotinic acid, cholestyramine, colestipol and probucol.

BACKGROUND OF THE INVENTION

Atherosclerosis and other peripheral vascular diseases are the major causes effecting the quality of life of millions of people. Therefore, considerable attention has been directed towards understanding the etiology of hypercholesterolemia and hyperlipidemia and development of effective therapeutic strategies.

Hypercholesterolemia has been defined as plasma cholesterol level that exceeds arbitrarily defined value called "normal" level. Recently, it has been accepted that "ideal" plasma levels of cholesterol are much below the "normal" level of cholesterol in the general population and the risk of coronary artery disease (CAD) increases as cholesterol level rises above the "optimum" (or "ideal") value. There is clearly a definite cause and effect-relationship between hypercholesterolemia and CAD, particularly for individuals with multiple risk factors. Most of the cholesterol is present in the esterified forms with various lipoproteins such as Low density lipoprotein (LDL), Intermediate density lipoprotein (IDL), High density lipoprotein (HDL) and partially as Very low density lipoprotein (VLDL). Studies clearly indicate that there is an inverse correlationship between CAD and atherosclerosis with serum HDL-cholesterol concentrations, (Stampfer et al., *N. Engl. J. Med.,* 325 (1991), 373-381) and the risk of CAD increases with increasing levels of LDL and VLDL.

In CAD, generally "fatty streaks" in carotid, coronary and cerebral arteries, are found which are primarily free and esterified cholesterol. Miller et al., (*Br. Med. J.,* 282 (1981), 1741-1744) have shown that increase in HDL-particles may decrease the number of sites of stenosis in coronary arteries of human, and high level of HDL-cholesterol may protect against the progression of atherosclerosis. Picardo el al, *Arteriosclerosis* 6 (1986) 434-441 have shown by in vitro experiment that HDL is capable of removing cholesterol from cells. They suggest that HDL may deplete tissues of excess free cholesterol and transfer it to liver (Macikinnon et al., *J. Biol. chem.* 261 (1986), 2548-2552). Therefore, agents that increase HDL cholesterol would have therapeutic significance for the treatment of hypercholesterolemia and coronary heart diseases (CHD).

Obesity is a disease highly prevalent in affluent societies and in the developing world and is a major cause of morbidity and mortality. It is a state of excess body fat accumulation. The causes of obesity are unclear. It is believed to be of genetic origin or promoted by an interaction between the genotype and environment. Irrespective of the cause, the result is fat deposition due to imbalance between the energy intake versus energy expenditure. Dieting, exercise and appetite suppression have been a part of obesity treatment. There is a need for efficient therapy to fight this disease since it may lead to coronary heart disease, diabetes, stroke, hyperlipidemia, gout, osteoarthritis, reduced fertility and many other psychological and social problems.

Diabetes and insulin resistance is yet another disease which severely effects the quality of large population in the world. Insulin resistance is the diminished ability of insulin to exert its biological action across a broad range of concentrations. In insulin resistance, the body secretes abnormally high amounts of insulin to compensate for this defect; failing which, the plasma glucose concentration inevitably rises and develops into diabetes. Among the developed countries, diabetes mellitus is a common problem and is associated with a variety of abnormalities including obesity, hypertension, hyperlipidemia (*J. Clin. Invest.*, 75 (1985) 809-817; *N. Engl. J. Med* 317 (1987) 350-357; *J. Clin. Endocrinol. Metab.*, 66 (1988) 580-583; *J. Clin. Invest.* 68 (1975) 957-969) and other renal complications (patent publication No. WO 95/21608). It is now increasingly being recognized that insulin resistance and relative hyperinsulinemia have a contributory role in obesity, hypertension, atherosclerosis and type 2 diabetes mellitus. The association of insulin resistance with obesity, hypertension and angina has been described as a syndrome having insulin resistance as the central pathogenic link-Syndrome-X.

Hyperlipidemia is the primary cause for cardiovascular (CVD) and other peripheral vascular diseases. High risk of CVD is related to the higher LDL (Low Density Lipoprotein) and VLDL (Very Low Density Lipoprotein) seen in hyperlipidemia. Patients having glucose intolerance/insulin resistance in addition to hyperlipidemia have higher risk of CVD. Numerous studies in the past have shown that lowering of plasma triglycerides and total cholesterol, in particular LDL and VLDL and increasing HDL cholesterol help in preventing cardiovascular diseases.

Peroxisome proliferator activated receptors (PPAR) are members of the nuclear receptor super family. The gamma (γ) isoform of PPAR (PPARγ) has been implicated in regulating differentiation of adipocytes (*Endocrinology*, 135 (1994) 798-800) and energy homeostasis (Cell, 83 (1995) 803-812), whereas the alpha (α) isoform of PPAR (PPARα) mediates fatty acid oxidation (*Trend Endocrin. Metab.*, 4 (1993) 291-296) thereby resulting in reduction of circulating free fatty acid in plasma (*Current Biol.* 5 (1995) 618-621). PPARα agonists have been found useful for the treatment of obesity (WO 97/36579). It has been recently disclosed that there exists synergism for the molecules, which are agonists for both PPARα and: PPARγ and suggested to be useful for the treatment of syndrome X (WO 97/25042). Similar synergism between the insulin sensitizer (PPARγ agonist) and HMG CoA reductase inhibitor has been observed which may be useful for the treatment of atherosclerosis and xanthoma (EP 0 753 298).

It is known that PPARγ plays an important role in adipocyte differentiation (*Cell*, 87 (1996) 377-389). Ligand activation of PPAR is sufficient to cause complete terminal differentiation (*Cell*, 79 (1994) 1147-1156) including cell cycle withdrawal. PPARγ is consistently expressed in certain cells and activation of this nuclear receptor with PPARγ agonists would stimulate the terminal differentiation of adipocyte precursors and cause morphological and molecular changes characteristics of a more differentiated, less malignant state (*Molecular Cell*, (1998), 465-470; *Carcinogenesis*, (1998), 1949-53; *Proc. Natl. Acad. Sci.*, 94 (1997) 237-241) and inhibition of expression of prostate cancer tissue (*Cancer Research* 58 (1998) 3344-3352). This would be useful in the treatment of certain types of cancer, which express PPARγ and could lead to a quite nontoxic chemotherapy.

Leptin resistance is a condition wherein the target cells are unable to respond to leptin signal. This may give rise to obesity due to excess food intake and reduced energy expenditure and cause impaired glucose tolerance, type 2 diabetes, cardiovascular diseases and such other interrelated complications. Kallen et al (*Proc. Natl. Acad. Sci.* (1996) 93, 5793-5796) have reported that insulin sensitizers which perhaps due to the PPAR agonist expression and thereby lower plasma leptin concentrations. However, it has been recently disclosed that compounds having insulin sensitizing property also possess leptin sensitization activity. They lower the circulating plasma leptin concentrations by improving the target cell response to leptin (WO 98/02159).

A few β-aryl-α-hydroxy propionic acids, their derivatives and their analogs have been reported to be useful in the treatment of hyperglycemia and hypercholesterolemia. Some of such compounds described in the prior art are outlined below:

i) U.S. Pat. No. 5,306,726, WO 91/19702 disclose several 3-aryl-2-hydroxypropionic acid derivatives of general formulas (IIa) and (IIb) as hypolipidemic and hypoglycemic agents.

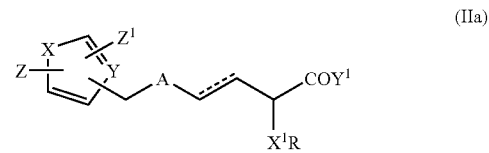

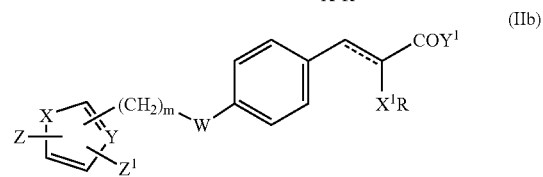

Examples of these compounds are shown in formulas (II c) and (II d)

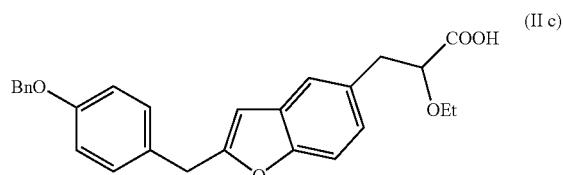

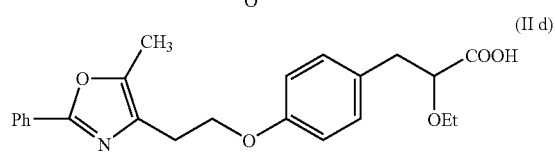

ii) International publication Nos. WO 95/03038 and WO 96/04260 discloses compounds of formula (II e)

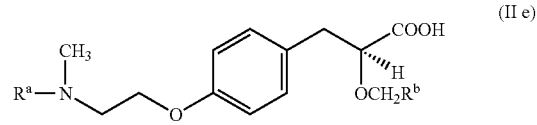

wherein $R^a$ represents 2-benzoxazolyl or 2-pyridyl and $R^b$ represent $CF_3$, $CH_2OCH_3$ or $CH_3$. A typical example is (S)-3-[4-[2-[N-(2-benzoxazolyl)-N-methylamino]ethoxy]phenyl]-2-(2,2-trifluoroethoxy)propanoic acid (II f).

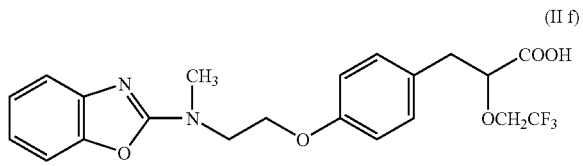

(II f)

iii) International publication Nos. WO 94/13650, WO 94/01420 and WO 95/17394 disclose the compounds of general formula (II g)

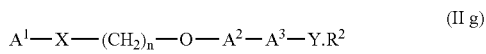

(II g)

wherein $A^1$ represents aromatic heterocycle, $A^2$ represents substituted benzene ring and $A^3$ represents a moiety of formula $(CH_2)_m$—CH—$(OR^1)$, wherein $R^1$ represents alkyl groups, m is an integer; X represents substituted or unsubstituted N; Y represents C=O or C=S; $R^2$ represents $OR^3$ where $R^3$ may be alkyl, aralkyl, or aryl group; n represents an integer in the range of 2-6.

An example of these compounds is shown in formula (IIh).

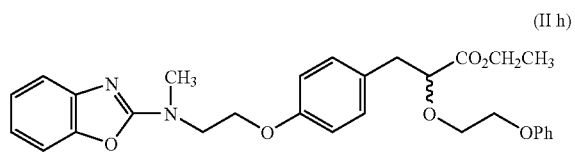

(II h)

iii) U.S. Pat. No. 5,227,490 disclose compounds of general formula (II i)

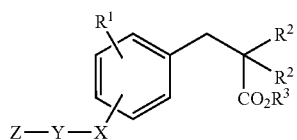

(III)

wherein $R^1$ is chosen independently from $(C_1-C_6)$alkyl, aryl$(C_4-C_{10})$alkyl, aryl, carboxy, $(C_1-C_6)$alkyloxy, carboxy $(C_0-C_6)$alkyl, hydroxy$(C_0-C_6)$alkyl, $(C_1-C_4)$alkylsulfonyl $(C_0-C_6)$alkyl, $(C_0-C_4)$alkylamino$(C_0-C_6)$alkyl, aryl$(C_0-C_{10})$alkylamino$(C_0-C_6)$alkyl, $(C_2-C_{10})$acylamino$(C_0-C_6)$alkyl, $(C_1-C_4)$carboalkoxy$(C_0-C_6)$alkyl or halogen atom; $R^2$ is chosen from hydrogen, halogen, hydroxy, $(C_1-C_6)$alkyloxy, aryl$(C_0-C_4)$alkyl, aryl$(C_0-C_6)$alkyloxy, $(C_1-C_6)$alkyl wherein the alkyl group is unsubstituted or substituted with one or more groups chosen from hydroxy, $(C_1-C_4)$alkyloxy, Amino$(C_1-C_{10})$alkylcarbonyl, aryl$(C_0-C_{10})$alkylcarbonyl, aryl$(C_0-C_{10})$alkylcabonylamino, $(C_1-C_6)$alkylsulfonyl, aryl $(C_0-C_6)$alkylsulfonyl, $(C_1-C_6)$alkylsulfonylamino, aryl$(C_0-C_{10})$alkylsulfonylamino, $(C_1-C_{10})$alkyloxycarbonylamino, aryl$(C_0-C_6)$alkylamino, aryl$(C_0-C_6)$alkylcarbonylamino, amino, carboxy, aryl, carbonyl-P-or $SO_2$—P wherein P is a single L or D amino acid or a sequence of 2-4 L or D amino acids connected by amide linkage; or $R^2$ represents carboxyl, $(C_1-C_6)$alkylcarbonyl, aryl$(C_1-C_{10})$alkylcarbonyl, $(C_1-C_6)$alkyloxycarbonylamino$(C_1-C_6)$alkyl, $(C_1-C_6)$alkylaminocarbonylamino$(C_1-C_6)$alkyl, aryl$(C_0-C_6)$alkylaminocarbonylamino$(C_1-C_6)$alkyl, aryl$(C_0-C_6)$alkyloxycarbonylamino$(C_1-C_6)$alkyl, $(C_1-C_6)$alkoxycarbonyl or aryl$(C_0-C_6)$alkyloxycarbonyl and provided that when there is more than one $R^2$ on the same carbon atom they may be the same or different; $R^3$ is hydrogen, $(C_1-C_6)$alkyl, aryl$(C_1-C_{10})$alkyl, Z is $NR^4R^5$ wherein $R^4$ and $R^5$ are independently hydrogen, $(C_1-C_6)$alkyl, aryl$(C_1-C_{10})$alkyl wherein said alkyl groups are unsubstituted or substituted with $(C_1-C_4)$ alkyloxy, carboxy $(C_0-C_6)$alkyl, hydroxy, halogen or Z represents a 4-9 membered mono or bicyclic ring system containing 1, 2 or 3 heteroatoms chosen from N, O or S and either unsubstituted or substituted with $R^4$ or $R^5$ br

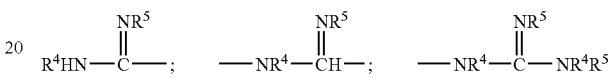

Y is $(C_1-C_{10})$alkyl either unsubstituted or unsubstituted with one or more groups selected from $R^4$ or $R^5$; or Y represents $(C_4-C_8)$cycloalkyl, aryl, $(C_0-C_3)$alkylaryl$(C_0-C_3)$alkyl, $(C_0-C_3)$alkylaryl$(C_0-C_3)$alkylcarbonyl, $(C_0-C_3)$alkylaryl$(C_0-C_3)$alkylcarboxamido, $(C_0-C_3)$alkylaryloxy$(C_0-C_3)$alkyl, $(C_0-C_3)$alkyloxy$(C_0-C_6)$alkyl,

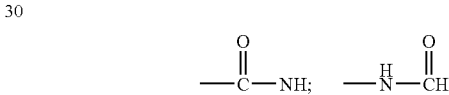

or —$(CH_2)_m$—Q—$(CH)_n$ where Q is a $C_2-C_8$ membered heterocyclic ring containing 1, 2 or 3 heteroatoms chosen from N, O or S and substituted or unsubstituted with oxo, thio, or $(C_1-C_6)$alkyl and m and n are chosen from the integers 0, 1, 2 or 3;

X is O, S, SO, $SO_2$, CO, —$NR^4CO$—, $CONR^4$—, —$CH_2$—, —CH=CH—, —C=C—, —$NR^4CS$—, —$CSNR^4$— or $SO_2NR^4$— or $NR^4SO_2$;

An example of these compounds is shown in formula (II j)

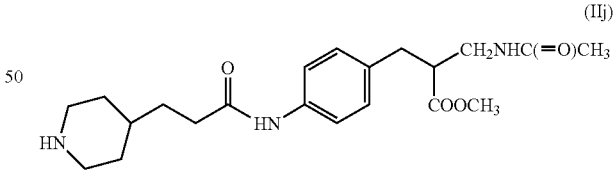

(IIj)

SUMMARY OF THE INVENTION

With an objective to develop novel compounds for lowering cholesterol and reducing body weight with beneficial effects in the treatment and/or prophylaxis of diseases related to increased levels of lipids, atherosclerosis, coronary artery diseases, Syndrome-X, impaired glucose tolerance, insulin resistance, insulin resistance leading to type 2 diabetes and diabetes complications thereof, for the treatment of diseases wherein insulin resistance is the pathophysiological mechanism and for the treatment of hypertension, with better efficacy, potency and lower toxicity, we focussed our research to develop new compounds effective in the treatment of the above mentioned diseases. Effort in this direction has led to compounds having general formula (I).

The main objective of the present invention is therefore, to provide novel β-aryl-α-oxysubstituted alkylcarboxylic acids, their derivatives, their analogs, their tautomeric forms, their stereoisomers, their polymorphs, their pharmaceutically acceptable salts, their pharmaceutically acceptable solvates and pharmaceutical compositions containing them, or their mixtures.

Another objective of the present invention is to provide novel β-aryl-α-oxysubstituted alkylcarboxylic acids, their derivatives, their analogs, their tautomeric forms, their stereoisomers, their polymorphs, their pharmaceutically acceptable salts, their pharmaceutically acceptable solvates and pharmaceutical compositions containing them or their mixtures which may have agonist activity against PPARα and/or PPARγ, and optionally inhibit HMG CoA reductase, in addition to having agonist activity against PPARα and/or PPARγ.

Another objective of the present invention is to provide novel β-aryl-α-oxysubstituted alkylcarboxylic acids, their derivatives, their analogs, their tautomeric forms, their stereoisomers, their polymorphs, their pharmaceutically acceptable salts, their pharmaceutically acceptable solvates and pharmaceutical compositions containing them or their mixtures having enhanced activities, without toxic effect or with reduced toxic effect.

Yet another objective of the present invention is a process for the preparation of novel β-aryl-α-oxysubstituted alkylcarboxylic acids of formula (I), their derivatives, their analogs, their tautomeric forms, their stereoisomers, their polymorphs, their pharmaceutically acceptable salts and their pharmaceutically acceptable solvates.

Still another objective of the present invention is to provide pharmaceutical compositions containing compounds of the general formula (I), their analogs, their derivatives, their tautomers, their stereoisomers, their polymorphs, their salts, solvates or their mixtures in combination with suitable carriers, solvents, diluents and other media normally employed in preparing such compositions.

Another objective of the present invention is to provide novel intermediates, a process for their preparation and use of the intermediates in processes for preparation of β-aryl-α-oxysubstituted alkyl carboxylic acids of formula (I), their derivatives, their analogs, their tautomers, their stereoisomers, their polymorphs, their salts and their pharmaceutically acceptable solvates.

DETAILED DESCRIPTION OF THE INVENTION

β-Aryl α-oxysubstituted propionic acids, their derivatives and their analogs of the present invention have the general formula (I)

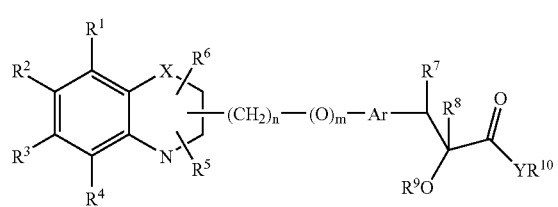

(I)

wherein the groups $R^1$, $R^2$, $R^3$, $R^4$ and the groups $R^5$ and $R^6$ when attached to carbon atom, may be same or different and represent hydrogen, halogen, hydroxy, nitro, cyano, formyl or unsubstituted or substituted groups selected from alkyl, cycloalkyl, alkoxy, cycloalkoxy, aryl, aryloxy, aralkyl, aralkoxy, heterocyclyl, heteroaryl, heteroaralkyl, heteroaryloxy, heteroaralkoxy, acyl, acyloxy, amino, acylamino, monoalkylamino, dialkylamino, arylamino, aralkylamino, alkoxycarbonyl, aryloxycarbonyl, aralkoxycarbonyl, alkylthio, alkoxycarbonylamino, aryloxycarbonylamino, aralkoxycarbonylamino, carboxylic acid or its derivatives, or sulfonic acid or its derivatives; one or both of $R^5$ and $R^6$ may also represent an oxo group when they are attached to carbon atom; $R^5$ and $R^6$ when attached to nitrogen atom represent hydrogen, hydroxy, formyl or unsubstituted or substituted groups selected from alkyl, cycloalkyl, alkoxy, cycloalkoxy, aryl, aralkyl, heterocyclyl, heteroaryl, heteroaralkyl, acyl, acyloxy, amino, acylamino, monoalkylamino, dialkylamino, arylamino, aralkylamino, aryloxy, aralkoxy, heteroaryloxy, heteroaralkoxy, alkoxycarbonyl, aryloxycarbonyl, aralkoxycarbonyl, alkylthio groups, carboxylic acid derivatives, or sulfonic acid derivatives; X represents a heteroatom selected from oxygen, sulfur or $NR^{11}$ where $R^{11}$ represents hydrogen or unsubstituted or substituted groups selected from alkyl, cycloalkyl, aryl, aralkyl, acyl, alkoxycarbonyl, aryloxycarbonyl or aralkoxycarbonyl groups; Ar represents an unsubstituted or substituted divalent single or fused aromatic or heterocyclic group; $R^7$ represents hydrogen atom, hydroxy, alkoxy, halogen, lower alkyl, unsubstituted or substituted aralkyl group or forms a bond together with the adjacent group $R^8$; $R^8$ represents hydrogen, hydroxy, alkoxy, halogen, lower alkyl group, acyl or unsubstituted or substituted aralkyl or $R^8$ forms a bond together with $R^7$; $R^9$ represents hydrogen or unsubstituted or substituted groups selected from alkyl, cycloalkyl, aryl, aralkyl, alkoxycarbonyl, aryloxycarbonyl, alkylaminocarbonyl, arylaminocarbonyl, acyl, heterocyclyl, heteroaryl or heteroaralkyl groups; $R^{10}$ represents hydrogen or unsubstituted or substituted groups selected from alkyl, cycloalkyl, aryl, aralkyl, heterocyclyl, heteroaryl or heteroaralkyl groups; Y represents oxygen or $NR^{12}$, where $R^{12}$ represents hydrogen, alkyl, aryl, hydroxyalkyl, aralkyl, heterocyclyl, heteroaryl or heteroaralkyl groups; $R^{10}$ and $R^{12}$ together may form a 5 or 6 membered cyclic structure containing carbon atoms, at least one nitrogen atom and which may optionally contain one or two additional heteroatoms selected from oxygen, sulfur or nitrogen; the linking group represented by $-(CH_2)_n-(O)_m-$ may be attached either through a nitrogen atom or a carbon atom; n is an integer ranging from 1-4 and m is an integer 0 or 1.

Suitable groups represented by $R^1$-$R^4$ and the groups $R^5$ and $R^6$ when-attached to carbon atom, may be selected from hydrogen, halogen atom such as fluorine, chlorine, bromine or iodine; hydroxy, cyano, nitro, formyl, substituted or unsubstituted $(C_1$-$C_{12})$alkyl group, especially, linear or branched $(C_1$-$C_{10})$alkyl group, such as methyl, ethyl, n-propyl, iso-propyl, n-butyl, iso-butyl, t-butyl, n-pentyl, iso-pentyl, hexyl, heptyl, octyl and the like; cyclo$(C_3$-$C_6)$alkyl group such as cyclopropyl, cyclobutyl, cyclopentyl, cyclohexyl and the like, the cycloalkyl group may be substituted; $(C_1$-$C_6)$alkoxy such as methoxy, ethoxy, propyloxy, butyloxy, iso-propyloxy and the like, which may be substituted; cyclo$(C_3$-$C_6)$alkoxy group such as cyclopropyloxy, cyclobutyloxy, cyclopentyloxy, cyclohexyloxy and the like, the cycloalkoxy group may be substituted; aryl group such as phenyl, naphthyl and the like, the aryl group may be substituted; aryloxy group such as phenoxy, naphthyloxy and the like, the aryloxy group may be substituted; aralkyl such as benzyl, phenethyl, $C_6H_5CH_2CH_2CH_2$, naphthylmethyl and the like, the aralkyl group may be substituted and the substituted aralkyl is a group such as $CH_3C_6H_4CH_2$, $Hal-C_6H_4CH_2$, $CH_3OC_6H_4CH_2$, $CH_3OC_6H_4CH_2CH_2$ and the like; aralkoxy group such as benzyloxy, phenethyloxy, naphthylmethyloxy, phenylpropyloxy and the like, the aralkoxy group may be substituted; heterocyclyl groups such as aziridinyl, pyrrolidinyl, morpholinyl, piperidinyl, piperazinyl and the like, the heterocyclyl group may be substituted; heteroaryl group such as pyridyl, thienyl, furyl, pyrrolyl, oxazolyl, thiazolyl, imidazolyl, oxadiazolyl, tetrazolyl, benzopyranyl, benzofuryl and the like, the heteroaryl group may be substituted; heteroaralkyl group such as furanmethyl, pyridinemethyl, oxazolemethyl, oxazolethyl and the like, the heteroaralkyl group may be substituted; heteroaryloxy and heteroaralkoxy, wherein heteroaryl and heteroaralkyl moieties are as defined earlier and may be substituted; acyl group such as acetyl, propionyl, benzoyl and the like, the acyl group may be substituted; acyloxy group such as OOCMe, OOCEt, OOCPh and the like, which may be substituted; acylamino groups such as $NHCOCH_3$, $NHCOC_2H_5$, $NHCOC_3H_7$, $NHCOC_6H_5$ and the like, which may be substituted; monoalkylamino group such as $NHCH_3$, $NHC_2H_5$, $NHC_3H_7$, $NHC_6H_{13}$, and the like, which may be substituted; dialkylamino group such as $N(CH_3)_2$, $NCH_3(C_2H_5)$, $N(C_2H_5)_2$ and the like, which may be substituted; arylamino group such as $HNC_6H_5$, $NCH_3(C_6H_5)$, $NHC_6H_4CH_3$, $NHC_6H_4$-Hal and the like, which may be substituted; aralkylamino group such as $C_6H_5CH_2NH$, $C_6H_5CH_2CH_2NH$, $C_6H_5CH_2NCH_3$ and the like, which may be substituted; amino group; alkoxycarbonyl such as methoxycarbonyl, ethoxycarbonyl and the like, which may be substituted; aryloxycarbonyl group such as phenoxycarbonyl, naphthyloxycarbonyl and the like, the aryloxycarbonyl group may be substituted; aralkoxycarbonyl group such as benzyloxycarbonyl, phenethyloxycarbonyl, naphthylmethoxycarbonyl and the like, which may be substituted; $(C_1-C_6)$alkylthio which may be substituted; alkoxycarbonylamino group such as $NHCOOC_2H_5$, $NHCOOCH_3$ and the like, which may be substituted; aryloxycarbonylamino group such as $NHCOOC_6H_5$, $NCH_3COOC_6H_5$, $NC_2H_5COOC_6H_5$, $NHCOOC_6H_4CH_3$, $NHCOOC_6HOCH_3$ and the like, which may be substituted; aralkoxycarbonylamino group such as $NHCOOCH_2C_6H_5$, $NHCOOCH_2CH_2C_6H_5$, $N(CH_3)COOCH_2C_6H_5$, $N(C_2H_5)COOCH_2C_6H_5$, $NHCOOCH_2C_6H_4—CH_3$, $NHCOOCH_2C_6H_4OCH_3$ and the like, which may be substituted, carboxylic acid or its derivatives such as amides, like $CONH_2$, CONHMe, $CONMe_2$, CONHEt, $CONEt_2$, CONHPh and the like, the carboxylic acid derivatives may be substituted; sulfonic acid or its derivatives such as $SO_2NH_2$, $SO_2NHMe$, $SO_2NMe_2$, $SO_2NHCF_3$ and the like, the sulfonic acid derivatives may be substituted. One or both of $R^5$ and $R^6$ may also represent an oxo group, when they are attached to carbon atom.

When the groups represented by $R^1-R^4$ and the groups $R^5$ and $R^6$ when attached to carbon atom are substituted, the substituents may be selected from halogen, hydroxy, nitro, thio or unsubstituted or substituted groups selected from alkyl, cycloalkyl, alkoxy, cycloalkoxy, aryl, aralkyl, aryloxy, aralkoxy, alkoxyalkyl, aryloxyalkyl, aralkoxyalkyl, heterocyclyl, heteroaryl, heteroaralkyl, acyl, acyloxy, hydroxyalkyl, amino, acylamino, arylamino, aminoalkyl, alkoxycarbonyl, alkylamino, alkylthio groups, carboxylic acid or its derivatives or sulfonic acid or its derivatives. These groups are as defined above.

It is preferred that the substituents on $R^1-R^6$ represent halogen atom such as fluorine, chlorine or bromine; alkyl group such as methyl, ethyl, iso-propyl, n-propyl, n-butyl; cycloalkyl group such as cyclopropyl; aryl group such as phenyl; aralkyl group such as benzyl; $(C_1-C_3)$alkoxy, benzyloxy, hydroxy group, acyl or acyloxy groups.

Suitable $R^5$ and $R^6$ when attached to nitrogen atom is selected from hydrogen, hydroxy, formyl; substituted or unsubstituted $(C_1-C_{12})$alkyl group, especially, linear or branched $(C_1-C_6)$alkyl group, such as methyl, ethyl, n-propyl, isopropyl, n-butyl, iso-butyl, t-butyl, n-pentyl, isopentyl, hexyl and the like; $(C_1-C_6)$alkoxy such as methoxy, ethoxy, propyloxy, butyloxy, iso-propyloxy and the like, which may be substituted, cyclo$(C_3-C_6)$alkyl group such as cyclopropyl, cyclobutyl, cyclopentyl, cyclohexyl and the like, the cycloalkyl group may be substituted; cyclo$(C_3-C_6)$alkoxy group such as cyclopropyloxy, cyclobutyloxy, cyclopentyloxy, cyclohexyloxy and the like, the cycloalkoxy group may be substituted; aryl group such as phenyl, naphthyl and the like, the aryl group may be substituted; aralkyl such as benzyl, phenethyl, $C_6H_5CH_2CH_2CH_2$, naphthylmethyl and the like, the aralkyl group may be substituted and the substituted aralkyl is a group such as $CH_3C_6H_4CH_2$, $Hal-C_6H_4CH_2$, $CH_3OC_6H_4CH_2$, $CH_3OC_6H_4CH_2CH_2$ and the like; aryloxy group such as phenoxy, naphthyloxy and the like, the aryloxy group may be substituted; aralkoxy group such as benzyloxy, phenethyloxy, naphthylmethyloxy, phenylpropyloxy and the like, the aralkoxy group may be substituted; heterocyclyl groups such as aziridinyl, pyrrolidinyl, morpholinyl, piperidinyl, piperazinyl and the like, the heterocyclyl group may be substituted; heteroaryl group such as pyridyl, thienyl, furyl, pyrrolyl, oxazolyl, thiazolyl, imidazolyl, oxadiazolyl, tetrazolyl, benzopyranyl, benzofuryl and the like, the heteroaryl group may be substituted; heteroaralkyl group such as furanmethyl, pyridinemethyl, oxazolemethyl, oxazolethyl and the like, the heteroaralkyl group may be substituted; heteroaryloxy and heteroaralkoxy, wherein heteroaryl and heteroaralkyl moieties are as defined earlier and may be substituted; acyl group such as acetyl, propionyl, benzoyl and the like, the acyl group may be substituted; acyloxy group such as OOCMe, OOCEt, OOCPh and the like, which may be substituted; monoalkylamino group such as $NHCH_3$, $NHC_2H_5$, $NHC_3H_7$, $NHC_6H_{13}$ and the like, which may be substituted; dialkylamino group such as $N(CH_3)_2$, $NCH_3(C_2H_5)$, $N(C_2H_5)_2$ and the like, which may be substituted; acylamino groups such as $NHCOCH_3$, $NHCOC_2H_5$, $NHCOC_3H_7$, $NHCOC_6H_5$ and the like, which may be substituted; arylamino group such as $HNC_6H_5$, $NCH_3(C_6H_5)$, $NHC_6H_4CH_3$, $NHC_6H_4$-Hal and the like, which may be substituted; amino group; aralkylamino group such as $C_6H_5CH_2NH$, $C_6H_5CH_2CH_2NH$, $C_6H_5CH_2NCH_3$ and the like, which may be substituted; alkoxycarbonyl group such as methoxycarbonyl, ethoxycarbonyl and the like, which may be substituted; aryloxycarbonyl group such as phenoxycarbonyl, naphthyloxycarbonyl and the like, which may be substituted; aralkoxycarbonyl group such as benzyloxycarbonyl, phenethyloxycarbonyl, naphthylmethoxycarbonyl and the like, which may be substituted; $(C_1-C_6)$alkylthio, which may be substituted; carboxylic acid derivatives such as amides, like $CONH_2$, CONHMe, $CONMe_2$, CONHEt, $CONEt_2$, CONHph and the like, the carboxylic acid derivatives may be substituted; sulfonic acid derivatives such as $SO_2NH_2$, $SO_2NHMe$, $SO_2NMe_2$, $SO_2NHCF_3$ and the like, the sulfonic acid derivatives may be substituted.

When the groups represented by $R^5$ and $R^6$ attached to nitrogen are substituted, preferred substituents may be selected from halogen such as fluorine or chlorine; hydroxy, acyl, acyloxy or amino groups. These groups are as defined above.

Suitable X includes oxygen, sulfur or a group $NR^{11}$, preferably oxygen and sulfur. Suitably $R^{11}$ represents hydrogen, $(C_1-C_6)$alkyl group such as methyl, ethyl, propyl and the like; $(C_3-C_6)$cycloalkyl group such as cyclopropyl, cyclobutyl, cyclopentyl, cyclohexyl and the like; aryl group such as phenyl, naphthyl and the like; aralkyl group such as benzyl, phenethyl and the like; acyl group such as acetyl, propanoyl, butanoyl, benzoyl and the like; $(C_1-C_6)$alkoxycarbonyl such as methoxycarbonyl, ethoxycarbonyl and the like; aryloxycarbonyl such as phenoxycarbonyl, $CH_3OC_6H_4OCO$, $Hal-C_6H_4OCO$, $CH_3C_6H_4OCO$, naphthyloxycarbonyl and the like; aralkoxycarbonyl such as benzyloxycarbonyl, phenethyloxycarbonyl and the like; the groups represented by $R^{11}$ may be substituted or unsubstituted. When the groups represented by $R^{11}$ are substituted, the substituents may be selected from halogen, optionally halogenated lower alkyl, hydroxy, and optionally halogenated $(C_1-C_3)$alkoxy groups. These groups are as defined above.

It is preferred that the group represented by Ar includes substituted or unsubstituted groups selected from divalent phenylene, naphthylene, pyridyl, quinolinyl, benzofuryl, dihydrobenzofuryl, benzopyranyl, dihydrobenzopyranyl, indolyl, indolinyl, azaindolyl, azaindolinyl, pyrazolyl, benzothiazolyl, benzoxazolyl and the like. The substituents on the group represented by Ar may be selected from linear or branched optionally halogenated $(C_1-C_6)$alkyl, optionally halogenated $(C_1-C_3)$alkoxy, halogen, acyl, amino, acylamino, thio or carboxylic or sulfonic acids and their derivatives. The substituents are defined as they are for $R^1$-$R^4$.

It is more preferred that Ar represent substituted or unsubstituted divalent, phenylene, naphthylene, benzofuryl, indolyl, indolinyl, quinolinyl, azaindolyl, azaindolinyl, benzothiazolyl or benzoxazolyl groups.

It is still more preferred that Ar is represented by divalent phenylene, naphthylene or benzofuryl, which may be unsubstituted or substituted by alkyl, haloalkyl, methoxy or haloalkoxy groups.

Suitable $R^7$ includes hydrogen, hydroxy, lower alkyl groups such as methyl, ethyl or propyl; $(C_1-C_3)$alkoxy group such as methoxy, ethoxy, propoxy and the like; halogen atom such as fluorine, chlorine, bromine or iodine; aralkyl such as benzyl, phenethyl and the like, which may be unsubstituted or substituted or $R^7$ together with $R^8$ represents a bond. The substituents are selected from halogen, hydroxy or alkyl groups.

Suitable $R^8$ may be hydrogen, hydroxy, lower alkyl groups such as methyl, ethyl or propyl; $(C_1-C_3)$alkoxy such as methoxy, ethoxy, propoxy and the like; halogen atom such as fluorine, chlorine, bromine or iodine; $(C_2-C_{10})$acyl group such as acetyl, propanoyl, butanoyl, pentanoyl, benzoyl and the like; aralkyl such as benzyl, phenethyl and the like, which may be unsubstituted or substituted or $R^8$ together with $R^7$ forms a bond. The substituents are selected from halogen, hydroxy or alkyl groups.

Suitable groups represented by $R^9$ may be selected from hydrogen, linear or branched $(C_1-C_{16})$alkyl, preferably $(C_1-C_{12})$alkyl group such as methyl, ethyl, n-propyl, iso-propyl, n-butyl, iso-butyl, pentyl, hexyl, octyl and the like, the alkyl group may be substituted; $(C_3-C_7)$cycloalkyl group such as cyclopropyl, cyclobutyl, cyclopentyl, cyclohexyl and the like, the cycloalkyl group may be substituted; aryl group such as phenyl, naphthyl and the like, the aryl group may be substituted; aralkyl group such as benzyl, phenethyl and the like, wherein the alkyl moiety may contain $(C_1-C_6)$ atoms, wherein the aryl moiety may be substituted; heteroaryl group such as pyridyl, thienyl, pyrrolyl, furyl and the like, the heteroaryl group may be substituted; heteroaralkyl group such as furanmethyl, pyridinemethyl, oxazolemethyl, oxazolethyl and the like, the heteroaralkyl group may be substituted; heterocyclyl group such as aziridinyl, pyrrolidinyl, piperidinyl and the like, the heterocyclyl group may be substituted; linear or branched $(C_2-C_{16})$acyl group such as acetyl, propanoyl, butanoyl, benzoyl, octanoyl, decanoyl and the like, which may be substituted; $(C_1-C_6)$alkoxycarbonyl group such as methoxycarbonyl, ethoxycarbonyl and the like, the alkoxycarbonyl group may be substituted; aryloxycarbonyl such as phenoxycarbonyl, naphthyloxycarbonyl and the like, the aryl group may be substituted; $(C_1-C_6)$alkylaminocarbonyl, the alkyl group may be substituted; arylaminocarbonyl such as PhNHCO, naphthylaminocarbonyl and the like, the aryl moiety may be substituted. The substituents may be selected from halogen, hydroxy, nitro or unsubstituted or substituted groups selected from alkyl, cycloalkyl, alkoxy, cycloalkoxy, aryl, aralkyl, aralkoxyalkyl, heterocyclyl, heteroaryl, heteroaralkyl, acyl, acyloxy, hydroxyalkyl, amino, acylamino, arylamino, aminoalkyl, aryloxy, aralkoxy, alkoxycarbonyl, alkylamino, alkoxyalkyl, aryloxyalkyl, alkylthio, thioalkyl groups, carboxylic acid or its derivatives or sulfonic acid or its derivatives. The substituents are as defined above.

Suitable groups represented by $R^{10}$ may be selected from hydrogen, linear or branched $(C_1-C_{16})$alkyl, preferably $(C_1-C_{12})$alkyl group such as methyl, ethyl, n-propyl, iso-propyl, n-butyl, iso-butyl, pentyl, hexyl, octyl and the like, the alkyl group may be substituted; $(C_3-C_7)$cycloalkyl such as cyclopropyl, cyclopentyl, cyclohexyl and the like, the cycloalkyl group may be substituted; aryl group such as phenyl, naphthyl and the like, the aryl group may be substituted; heteroaryl group such as pyridyl, thienyl, pyrrolyl, furyl and the like, the heteroaryl group may be substituted; heteroaralkyl group such as furanmethyl, pyridinemethyl, oxazolemethyl, oxazolethyl and the like, the heteroaralkyl group may be substituted; aralkyl group such as benzyl, phenethyl and the like, the aralkyl group may be substituted; heterocyclyl group such as aziridinyl, pyrrolidinyl, piperidinyl and the like, the heterocyclyl group may be substituted. The substituents on $R^{10}$ may be selected from halogen, hydroxy, nitro or unsubstituted or substituted groups selected from alkyl, cycloalkyl, alkoxy, cycloalkoxy, aryl, aralkyl, aralkoxyalkyl, heterocyclyl, heteroaryl, heteroaralkyl, acyl, acyloxy, hydroxyalkyl, amino, acylamino, arylamino, aminoalkyl, aryloxy, aralkoxy, alkoxycarbonyl, alkylamino, alkoxyalkyl, alkylthio, thioalkyl groups, carboxylic acid or its derivatives, or sulfonic acid or its derivatives. The substituents are as defined above.

Suitable groups represented by $R^{12}$ may be selected from hydrogen, linear or branched $(C_1-C_{16})$alkyl, preferably $(C_1-C_{12})$alkyl group such as methyl, ethyl, n-propyl, iso-propyl, n-butyl, iso-butyl, pentyl, hexyl, octyl and the like; hydroxy $(C_1-C_6)$alkyl; aryl group such as phenyl, naphthyl and the like; aralkyl group such as benzyl, phenethyl and the like; heterocyclyl group such as aziridinyl, pyrrolidinyl, piperidinyl and the like; heteroaryl group such as pyridyl, thienyl, pyrrolyl, furyl and the like; heteroaralkyl group such as furanmethyl, pyridinemethyl, oxazolemethyl, oxazolethyl and the like.

Suitable ring structures formed by $R^{10}$ and $R^{12}$ together may be selected from pyrrolidinyl, piperidinyl, morpholinyl, piperazinyl and the like.

Suitable m is an integer ranging from 0-1. It is preferred that when m=0, Ar represents substituted or unsubstituted benzofuryl, benzoxazolyl, benzothiazolyl, indolyl, indolinyl, dihydrobenzofuryl, or dihydrobenzopyranyl group and when m=1, Ar represents substituted or unsubstituted groups selected from divalent phenylene, naphthylene, pyridyl, quinolinyl, benzofuryl, dihydrobenzofuryl, benzopyranyl, dihydrobenzopyranyl, indolyl, indolinyl, azaindolyl, azaindolinyl, pyrazolyl, benzothiazolyl, benzoxazolyl and the like.

It is preferred that when m=0, Ar represents a divalent benzofuryl group, more preferably benzofuran-2,5-diyl group and when m=1, Ar represents a phenylene group. Suitable n is an integer ranging from 1 to 4, preferably n represents an integer 1 or 2.

It is preferred that when m=1, n represents 2.

It is also preferred that when m=0, n represents 1.

Pharmaceutically acceptable salts forming part of this invention include salts derived from inorganic bases such as Li, Na, K, Ca, M, Fe, Cu, Zn, Mn; salts of organic bases such as N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, benzylamine, phenylethylamine, dialkylamine, trialkylamine, thiamine, aminopyrimidine, aminopyridine, purine, spermidine, and the like; chiral bases like alkylphenylamine, glycinol, phenyl glycinol and the like, salts of natural amino acids such as glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids such as D-isomers or substituted amino acids; guanidine, substituted guanidine wherein the substituents are selected from nitro, amino, alkyl, alkenyl, alkynyl, ammonium or substituted ammonium salts and aluminum salts. Salts may include acid addition salts where appropriate which are, sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

Particularly useful compounds according to the present invention include:

Ethyl (E/Z)-3-[4-[2-(2,3-dihydro-1,4-benzoxazin-4-yl)ethoxy]phenyl]-2-ethoxypropenoate;
Ethyl (E)-3-[4-[2-2,3-dihydro-1,4-benzoxazin-4-yl)ethoxy]phenyl]-2-ethoxypropenoate;
Ethyl (Z)-3-[4-[2-(2,3-dihydro-1,4-benzoxazin-4-yl)ethoxy]phenyl]-2-ethoxypropenoate;
(±) Methyl 3-[4-[2-(2,3-dihydro-1,4-benzoxazin-4-yl)ethoxy]phenyl]-2-ethoxypropanoate;
(+) Methyl 3-[4-[2-(2,3-dihydro-1,4-benzoxazin-4-yl)ethoxy]phenyl]-2-ethoxypropanoate,
(−) Methyl 3-[4-[2-(2,3-dihydro-1,4-benzoxazin-4-yl)ethoxy]phenyl]-2-ethoxypropanoate;
Ethyl (E/Z)-3-[2-2,3-dihydro-1,4-benzoxazin-4-yl)methylbenzofuran-5-yl]-2-ethoxypropenoate;
Ethyl (E)-3-[2-2,3-dihydro-1,4-benzoxazin-4-yl)methylbenzofuran-5-yl]-2-ethoxypropenoate;
Ethyl (Z)-3-[2-(2,3-dihydro-1,4-benzoxazin-4-yl)methylbenzofuran-5-yl]-2-ethoxypropenoate;
Ethyl (E/Z)-3-[4-[2-(2,3-dihydro-1,4-benzothiazin-4-yl)ethoxy]phenyl]-2-ethoxypropenoate;
Ethyl (E)-3-[4-[2-(2,3-dihydro-1,4-benzothiazin-4-yl)ethoxy]phenyl]-2-ethoxypropenoate;
Ethyl (Z)-3-[4-[2-(2,3-dihydro-1,4-benzothiazin-4-yl)ethoxy]phenyl]-2-ethoxypropenoate,
(±) Methyl 3-[2-(2,3-dihydro-1,4-benzoxazin-4-yl)methylbenzofuran-5-yl]-2-ethoxypropanoate;
(+) Methyl 3-[2-(2,3-dihydro-1,4-benzoxazin-4-yl)methylbenzofuran-5-yl]-2-ethoxypropanoate;
(−) Methyl-3-[2-(2,3-dihydro-1,4-benzoxazin-4-yl)methylbenzofuran-5-yl]-2-ethoxypropanoate,
(±) Methyl-3-[4-[2-(2,3-dihydro-1,4-benzothiazin-4-yl)ethoxy]phenyl]-2-ethoxypropanoate;
(+) Methyl-3-[4-[2-(2,3-dihydro-1,4-benzothiazin-4-yl)ethoxy]phenyl]-2-ethoxypropanoate;
(−) Methyl-3-[4-[2-2,3-dihydro-1,4-benzothiazin-4-yl)ethoxy]phenyl]-2-ethoxypropanoate;
(±) Methyl 2-methyl-3-[4-[2-(2,3-dihydro-1,4-benzoxazin-4-yl)ethoxy]phenyl]-2-ethoxy propanoate;
(+) Methyl 2-methyl-3-[4-[2-(2,3-dihydro-1,4-benzoxazin-4-yl)ethoxy]phenyl]-2-ethoxy propanoate;
(−) Methyl 2-methyl-3-[4-[2-(2,3-dihydro-1,4-benzoxazin-4-yl)ethoxy]phenyl]-2-ethoxy propanoate;
(±) Methyl 2-(2-fluorobenzyl)-3-[4-[2-(2,3-dihydro-1,4-benzoxazin-4-yl)ethoxy]phenyl]-2-ethoxypropanoate;
(+) Methyl 2-(2-fluorobenzyl)-3-[4-[2-(2,3-dihydro-1,4-benzoxazin-4-yl)ethoxy]phenyl]-2-ethoxypropanoate;
(−) Methyl 2-(2-fluorobenzyl)-3-[4-[2-(2,3-dihydro-1,4-benzoxazin-4-yl)ethoxy]phenyl]-2-ethoxypropanoate;
Ethyl (E/Z)-3-[4-[2-(3-oxo-2H-1,4-benzoxazin-4-yl)ethoxy]phenyl]-2-ethoxypropenoate;
Ethyl (E)-3-[(4-[2-(3-oxo-2H-1,4-benzoxazin-4-yl)ethoxy]phenyl]-2-ethoxypropenoate;
Ethyl (Z)-3-[4-[2-(3-oxo-2H-1,4-benzoxazin-4-yl)ethoxy]phenyl]-2-ethoxypropenoate;
(±) Methyl 3-[4-[2-(3-oxo-2H-1,4-benzoxazin-4-yl)ethoxy]phenyl]-2-ethoxypropanoate;
(+) Methyl 3-[4-[2-<3-oxo-2H-1,4-benzoxazin-4-yl)ethoxy]phenyl]-2-ethoxypropanoate;
(−) Methyl 3-[4-[2-(3-oxo-2H-1,4-benzoxazin-4-yl)ethoxy]phenyl]-2-ethoxypropanoate;
Ethyl (E/Z)-3-[6-[2-(2,3-dihydro-1,4-benzothiazin-4-yl)ethoxy]naphthyl]-2-ethoxypropenoate;
Ethyl (E)-3-[6-[2-(2,3-dihydro-1,4-benzothiazin-4-yl)ethoxy]naphthyl]-2-ethoxypropenoate;
Ethyl (Z)-3-[6-[2-(2,3-dihydro-1,4-benzothiazin-4-yl)ethoxy]naphthyl]-2-ethoxypropenoate;
(±) Methyl 3-[6-[2-(2,3-dihydro-1,4-benzothiazin-4-yl)ethoxy]naphthyl]-2-ethoxypropanoate,
(+) Methyl 3-[6-[2-(2,3-dihydro-1,4-benzothiazin-4-yl)ethoxy]naphthyl]-2-ethoxypropanoate;
(−) Methyl 3-[6-[2-(2,3-dihydro-1,4-benzothiazin-4-yl)ethoxy]naphthyl]-2-ethoxypropanoate;
(±) Ethyl 3-[4-[2-(2,3-dihydro-1,4-benzoxazin-4-yl)ethoxy]phenyl]-2-hydroxypropanoate;
(+) Ethyl 3-[4-[2-(2,3-dihydro-1,4-benzoxazin-4-yl)ethoxy]phenyl]-2-hydroxypropanoate;
(−) Ethyl 3-[4-[2-(2,3-dihydro-1,4-benzoxazin-4-yl)ethoxy]phenyl]-2-hydroxypropanoate;
(±) Ethyl 3-[4-[2-(2,3-dihydro-1,4-benzothiazin-4-yl)ethoxy]phenyl]-2-hydroxypropanoate;
(+) Ethyl 3-[4-[2-(2,3-dihydro-1,4-benzothiazin-4-yl)ethoxy]phenyl]-2-hydroxypropanoate;

(−) Ethyl 3-[4-[2-(2,3-dihydro-1,4-benzothiazin-4-yl)ethoxy]phenyl]-2-hydroxypropanoate;
(±) Ethyl 3-[4-[2-(2,3-dihydro-1,4-benzoxazin-4-yl)ethoxy]phenyl]-2-benzyloxypropanoate;
(+) Ethyl 3-[4-[2-(2,3-dihydro-1,4-benzoxazin-4-yl)ethoxy]phenyl]-2-benzyloxypropanoate;
(−) Ethyl 3-[4-[2-(2,3-dihydro-1,4-benzoxazin-4-yl)ethoxy]phenyl]-2-benzyloxypropanoate;
(±) Ethyl 3-[4-[2-(2,3-dihydro-1,4-benzoxazin-4-yl)ethoxy]phenyl]-2-butoxypropanoate;
(+) Ethyl 3-[4-[2-(2,3-dihydro-1,4-benzoxazin-4-yl)ethoxy]phenyl]-2-butoxypropanoate;
(−) Ethyl 3-[4-[2-(2,3-dihydro-1,4-benzoxazin-4-yl)ethoxy]phenyl]-2-butoxypropanoate;
(±) Ethyl 3-[4-[2-(2,3-dihydro-1,4-benzoxazin-4-yl)ethoxy]phenyl]-2-hexyloxypropanoate;
(+) Ethyl 3-[4-[2-(2,3-dihydro-1,4-benzoxazin-4-yl)ethoxy]phenyl]-2-hexyloxypropanoate;
(−) Ethyl 3-[4-[2-(2,3-dihydro-1,4-benzoxazin-4-yl)ethoxy]phenyl]-2-hexyloxypropanoate;
Ethyl (E/Z)-3-[4-[2,3-dihydro-1,4-benzoxazin-4-yl)ethoxy]phenyl]-2-phenoxypropenoate;
Ethyl (E)-3-[4-[2-(2,3-dihydro-1,4-benzoxazin-4-yl)ethoxy]phenyl]-2-phenoxypropenoate;
Ethyl (Z)-3-[4-[2-(2,3-dihydro-1,4-benzoxazin-4-yl)ethoxy]phenyl]-2-phenoxypropenoate;
(±) Methyl 3-[4-[2-(2,3-dihydro-1,4-benzoxazin-4-yl)ethoxy]phenyl]-2-phenoxypropanoate;
(+) Methyl 3-[4-[2-(2,3-dihydro-1,4-benzoxazin-4-yl)ethoxy]phenyl]-2-phenoxypropanoate;
(−) Methyl 3-[4-[2-(2,3-dihydro-1,4-benzoxazin-4-yl)ethoxy]phenyl]-2-phenoxypropanoate;
Ethyl (E/Z)-3-[4-[2-(2,3-dihydro-1,4-benzothiazin-4-yl)ethoxy]phenyl]-2-phenoxypropenoate;
Ethyl (E)-3-[4-[2-2,3-dihydro-1,4-benzothiazin-4-yl)ethoxy]phenyl]-2-phenoxypropenoate;
Ethyl (Z)-3-[4-[2-2,3-dihydro-1,4-benzothiazin-4-yl)ethoxy]phenyl]-2-phenoxypropenoate;
(±) Methyl 3-[4-[2-(2,3-dihydro-1,4-benzothiazin-4-yl)ethoxy]phenyl]-2-phenoxypropanoate;
(+) Methyl 3-[4-[2-(2,3-dihydro-1,4-benzothiazin-4-yl)ethoxy]phenyl]-2-phenoxypropanoate;
(−) Methyl 3-[4-[2-(2,3-dihydro-1,4-benzothiazin-4-yl)ethoxy]phenyl]-2-phenoxypropanoate;
Ethyl (E/Z)-3-[4-(4-methyl-3,4-dihydro-1,4-benzoxazin-2-yl)methoxyphenyl]-2-ethoxy propenoate;
Ethyl (E)-3-[4-(4-methyl-3,4-dihydro-1,4-benzoxazin-2-yl)methoxyphenyl]-2-ethoxy propenoate;
Ethyl (Z)-3-[4-(4-methyl-3,4-dihydro-1,4-benzoxazin-2-yl)methoxyphenyl]-2-ethoxy propenoate;
(±) Methyl 3-[4-(4-methyl-3,4-dihydro-1,4-benzoxazin-2-yl)methoxyphenyl]-2-ethoxypropanoate;
(+) Methyl 3-[4-(4-methyl-3,4-dihydro-1,4-benzoxazin-2-yl)methoxyphenyl]-2-ethoxypropanoate;
(−) Methyl 3-[4-(4-methyl-3,4-dihydro-1,4-benzoxazin-2-yl)methoxyphenyl]-2-ethoxy propanoate;
Ethyl (E/Z)-3-[4-(4-benzyl-3,4-dihydro-1,4-benzoxazin-2-yl)methoxyphenyl]-2-ethoxy propenoate;
Ethyl (E)-3-[4-(4-benzyl-3,4-dihydro-1,4-benzoxazin-2-yl)methoxyphenyl]-2-ethoxy propenoate;
Ethyl (Z)-3-[4-(4-benzyl-3,4-dihydro-1,4-benzoxazin-2-yl)methoxyphenyl]-2-ethoxy propenoate;
(±) Methyl 3-[4-(4-benzyl-3,4-dihydro-1,4-benzoxazin-2-yl)methoxyphenyl]-2-ethoxy propanoate;
(+) Methyl 3-[4-(4-benzyl-3,4-dihydro-1,4-benzoxazin-2-yl)methoxyphenyl]-2-ethoxy propanoate;
(−) Methyl 3-[4-(4-benzyl-3,4-dihydro-1,4-benzoxazin-2-yl)methoxyphenyl]-2-ethoxy propanoate;
(±) 3-[4-[2-(2,3-Dihydro-1,4-benzoxazin-4-yl)ethoxy]phenyl]-2-ethoxypropanoic acid and its salts;
(+) 3-[4-[2-(2,3-Dihydro-1,4-benzoxazin-4-yl)ethoxy]phenyl]-2-ethoxypropanoic acid and its salts;
(−) 3-[4-[2-(2,3-Dihydro-1,4-benzoxazin-4-yl)ethoxy]phenyl]-2-ethoxypropanoic acid and its salts;
(±) 3-[2-(2,3-Dihydro-1,4-benzoxazin-4-yl)methylbenzofuran-5-yl]-2-ethoxypropanoic acid and its salts;
(+) 3-[2-(2,3-Dihydro-1,4-benzoxazin-4-yl)methylbenzofuran-5-yl]-2-ethoxypropanoic acid and its salts;
(−) 3-[2-(2,3-Dihydro-1,4-benzoxazin-4-yl)methylbenzofuran-5-yl]-2-ethoxypropanoic acid and its salts;
(±) 3-[2-(2,3-Dihydro-1,4-benzothiazin-4-yl)methylbenzofuran-5-yl]-2-ethoxypropanoic acid and its salts;
(+) 3-[2-(2,3-Dihydro-1,4-benzothiazin-4-yl)methylbenzofuran-5-yl]-2-ethoxypropanoic acid and its salts;
(−) 3-[2-(2,3-Dihydro-1,4-benzothiazin-4-yl)methylbenzofuran-5-yl]-2-ethoxypropanoic acid and its salts;
(±) 3-[4-[2-(2,3-Dihydro-1,4-benzothiazin-4-yl)ethoxy]phenyl]-2-ethoxypropanoic acid and its salts;
(+) 3-[4-[2-(2,3-Dihydro-1,4-benzothiazin-4-yl)ethoxy]phenyl]-2-ethoxypropanoic acid and its salts;
(−) 3-[4-[2-(2,3-Dihydro-1,4-benzothiazin-4-yl)ethoxy]phenyl]-2-ethoxypropanoic acid and its salts;
(±) 3-[4-[2-(2,3-Dihydro-1,4-benzothiazin-4-yl)ethoxy]phenyl]-2-ethoxypropanamide;
(+) 3-[4-[2-(2,3-Dihydro-1,4-benzothiazin-4-yl)ethoxy]phenyl]-2-ethoxypropanamide;
(−) 3-[4-[2-(2,3-Dihydro-1,4-benzothiazin-4-yl)ethoxy]phenyl]-2-ethoxypropanamide
(±) N-Methyl-3-[4-[2-(2,3-dihydro-1,4-benzothiazin-4-yl)ethoxy]phenyl]-2-ethoxypropanamide;
(+) N-Methyl-3-[4-[2-(2,3-dihydro-1,4-benzothiazin-4-yl)ethoxy]phenyl]-2-ethoxypropanamide;
(−) N-Methyl-3-[4-[2-(2,3-dihydro-1,4-benzothiazin-4-yl)ethoxy]phenyl]-2-ethoxypropanamide;
(±) 3-[4-[2-(2,3-Dihydro-1,4-benzoxazin-4-yl)ethoxy]phenyl]-2-ethoxypropanamide
(+) 3-[4-[2-(2,3-Dihydro-1,4-benzoxazin-4-yl)ethoxy]phenyl]-2-ethoxypropanamide,
(−) 3-[4-[2-(2,3-Dihydro-1,4-benzoxazin-4-yl)ethoxy]phenyl]-2-ethoxypropanamide;
(±) N-Methyl-3-[4-[2-(2,3-dihydro-1,4-benzoxazin-4-yl)ethoxy]phenyl]-2-ethoxypropanamide;
(+) N-Methyl-3-[4-[2-(2,3-dihydro-1,4-benzoxazin-4-yl)ethoxy]phenyl]-2-ethoxypropanamide;
(−) N-Methyl-3-[4-[2-(2,3-dihydro-1,4-benzoxazin-4-yl)ethoxy]phenyl]-2-ethoxypropanamide;
(±) N-Benzyl-3-[4-[2-(2,3-dihydro-1,4-benzoxazin-4-yl)ethoxy]phenyl]-2-ethoxypropanamide;
(+) N-Benzyl-3-[4-[2-2,3-dihydro-1,4-benzoxazin-4-yl)ethoxy]phenyl]-2-ethoxypropanamide,
(−) N-Benzyl-3-[4-[2-(2,3-dihydro-1,4-benzoxazin-4-yl)ethoxy]phenyl]-2-ethoxypropanamide;
(±) N-Benzyl-3-[4-[2-(2,3-dihydro-1,4-benzothiazin-4-yl)ethoxy]phenyl]-2-ethoxypropanamide;
(+) N-Benzyl-3-[4-[2-(2,3-dihydro-1,4-benzothiazin-4-yl)ethoxy]phenyl]-2-ethoxypropanamide;
(−) N-Benzyl-3-[4-[2-(2,3-dihydro-1,4-benzothiazin-4-yl)ethoxy]phenyl]-2-ethoxypropanamide;
(±) 2-Methyl-3-[4-[2-(2,3-dihydro-1,4-benzoxazin-4-yl)ethoxy]phenyl]-2-ethoxypropanoic acid and its salts;
(+) 2-Methyl-3-[4-[2-(2,3-dihydro-1,4-benzoxazin-4-yl)ethoxy]phenyl]-2-ethoxypropanoic acid and its salts;

(−) 2-Methyl-3-[4-[2-(2,3-dihydro-1,4-benzoxazin-4-yl)ethoxy]phenyl]-2-ethoxypropanoic acid and its salts;

(±) 2-(2-Fluorobenzyl)-3-[4-[2-(2,3-dihydro-1,4-benzoxazin-4-yl)ethoxy]phenyl]-2-ethoxypropanoic acid and its salts;

(+) 2-(2-Fluorobenzyl)-3-[4-[2-(2,3-dihydro-1,4-benzoxazin-4-yl)ethoxy]phenyl]-2-ethoxypropanoic acid and its salts;

(−) 2-(2-Fluorobenzyl)-3-[4-[2-(2,3-dihydro-1,4-benzoxazin-4-yl)ethoxy]phenyl]-2-ethoxypropanoic acid and its salts;

(±) 3-[4-[2-(3-Oxo-2H-1,4-benzoxazin-4-yl)ethoxy]phenyl]-2-ethoxypropanoic acid and its salts;

(+) 3-[4-[2-(3-Oxo-2H-1,4-benzoxazin-4-yl)ethoxy]phenyl]-2-ethoxypropanoic acid and its salts;

(−) 3-[4-[2-3-Oxo-2H-1,4-benzoxazin-4-yl)ethoxy]phenyl]-2-ethoxypropanoic acid and its salts;

(±) 3-[4-[2-(3-Oxo-2H-1,4-benzothiazin-4-yl)ethoxy]phenyl]-2-ethoxypropanoic acid and its salts;

(+) 3-[4-[2-(3-Oxo-2H-1,4-benzothiazin-4-yl)ethoxy]phenyl]-2-ethoxypropanoic acid and its salts;

(−) 3-[4-[2-(3-Oxo-2H-1,4-benzothiazin-4-yl)ethoxy]phenyl]-2-ethoxypropanoic acid and its salts;

(±) 3-[6-[2-(2,3-Dihydro-1,4-benzoxazin-4-yl)ethoxy]naphthyl]-2-ethoxypropanoic acid and its salts;

(+) 3-[6-[2-(2,3-Dihydro-1,4-benzoxazin-4-yl)ethoxy]naphthyl]-2-ethoxypropanoic acid and its salts;

(−) 3-[6-[2-(2,3-Dihydro-1,4-benzoxazin-4-yl)ethoxy]naphthyl]-2-ethoxypropanoic, acid and its salts;

(±) 3-[4-[2-(2-(3-Dihydro-1,4-benzothiazin-4-yl)ethoxy]naphthyl]-2-ethoxypropanoic acid and its salts;

(+) 3-[6-[2-(2,3-Dihydro-1,4-benzothiazin-4-yl)ethoxy]naphthyl]-2-ethoxypropanoic acid and its salts;

(−) 3-[6-[2-(2,3-Dihydro-1,4-benzothiazin-4-yl)ethoxy]naphthyl]-2-ethoxypropanoic acid and its salts;

(±) 3-[4-[2-(2,3-Dihydro-1,4-benzoxazin-4-yl)ethoxy]phenyl]-2-hydroxypropanoic acid and its salts;

(+) 3-[4-[2-(2,3-Dihydro-1,4-benzoxazin-4-yl)ethoxy]phenyl]-2-hydroxypropanoic acid and its salts;

(−) 3-[4-[2-2,3-Dihydro-1,4-benzoxazin-4-yl)ethoxy]phenyl]-2-hydroxypropanoic acid and its salts;

(±) 3-[4-[2-(2,3-Dihydro-1,4-benzothiazin-4-yl)ethoxy]phenyl]-2-hydroxypropanoic acid and its salts;

(+) 3-[4-[2-2,3-Dihydro-1,4-benzothiazin-4-yl)ethoxy]phenyl]-2-hydroxypropanoic acid and its salts;

(−) 3-[4-[2-(2,3-Dihydro-1,4-benzothiazin-4-yl)ethoxy]phenyl]-2-hydroxypropanoic acid and its salts;

(±) 3-[4-[2-(2,3-Dihydro-1,4-benzoxazin-4-yl)ethoxy]phenyl]-2-benzyloxypropanoic acid and its salts;

(+) 3-[4-[2-(2,3-Dihydro-1,4-benzoxazin-4-yl)ethoxy]phenyl]-2-benzyloxypropanoic acid and its salts;

(−) 3-[4-[2-(2,3-Dihydro-1,4-benzoxazin-4-yl)ethoxy]phenyl]-2-benzyloxypropanoic acid and its salts;

(±) 3-[4-[2-(2,3-Dihydro-1,4-benzoxazin-4-yl)ethoxy]phenyl]-2-butoxypropanoic acid and its salts;

(+) 3-[4-[2-(2,3-Dihydro-1,4-benzoxazin-4-yl)ethoxy]phenyl]-2-butoxypropanoic acid and its salts;

(−) 3-[4-[2-(2,3-Dihydro-1,4-benzoxazin-4-yl)ethoxy]phenyl]-2-butoxypropanoic acid and its salts;

(±) 3-[4-[2-(2,3-Dihydro-1,4-benzoxazin-4-yl)ethoxy]phenyl]-2-hexyloxypropanoic acid and its salts;

(+) 3-[4-[2-2,3-Dihydro-1,4-benzoxazin-4-yl)ethoxy]phenyl]-2-hexyloxypropanoic acid and its salts;

(−) 3-[4-[2-(2,3-Dihydro-1,4-benzoxazin-4-yl)ethoxy]phenyl]-2-hexyloxypropanoic acid and its salts;

(±) 3-[4-[2-(2,3-Dihydro-1,4-benzoxazin-4-yl)ethoxy]phenyl]-2-phenoxypropanoic acid and its salts;

(+) 3-[4-[2-(2,3-Dihydro-1,4-benzoxazin-4-yl)ethoxy]phenyl]-2-phenoxypropanoic acid and its salts;

(−) 3-[4-[2-(2,3-Dihydro-1,4-benzoxazin-4-yl)ethoxy]phenyl]-2-phenoxypropanoic acid and its salts;

(±) 3-[4-[2-(2,3-Dihydro-1,4-benzothiazin-4-yl)ethoxy]phenyl]-2-phenoxypropanoic acid and its salts;

(+) 3-[4-[2-(2,3-Dihydro-1,4-benzothiazin-4-yl)ethoxy]phenyl]-2-phenoxypropanoic acid and its salts;

(−) 3-[4-[2-(2,3-Dihydro-1,4-benzothiazin-4-yl)ethoxy]phenyl]-2-phenoxypropanoic acid and its salts;

(±) Methyl 2-methyl-3-[4-[2-(2,3-dihydro-1,4-benzoxazin-4-yl)ethoxy]phenyl]-2-phenoxy propanoate;

(+) Methyl 2-methyl-3-[4-[2-(2,3-dihydro-1,4-benzoxazin-4-yl)ethoxy]phenyl]-2-phenoxy propanoate;

(−) Methyl 2-methyl-3-[4-[2-(2,3-dihydro-1,4-benzoxazin-4-yl)ethoxy]phenyl]-2-phenoxy propanoate;

(±) 2-Methyl-3-[4-[2-(2,3-dihydro-1,4-benzoxazin-4-yl)ethoxy]phenyl]-2-phenoxypropanoic acid and its salts;

(+) 2-Methyl-3'-[4-[2-(2,3-dihydro-1,4-benzoxazin-4-yl)ethoxy]phenyl]-2-phenoxypropanoic acid and its salts;

(−) 2-Methyl-3-[4-[2-(2,3-dihydro-1,4-benzoxazin-4-yl)ethoxy]phenyl]-2-phenoxypropanoic acid and its salts;

(±) Methyl 2-methyl-3-[4-[2-(2,3-dihydro-1,4-benzothiazin-4-yl)ethoxy]phenyl]-2-phenoxy propanoate;

(+) Methyl 2-methyl-3-[4-[2-(2,3-dihydro-1,4-benzothiazin-4-yl)ethoxy]phenyl]-2-phenoxy propanoate;

(−) Methyl 2-methyl-3-[4-[2-(2,3-dihydro-1,4-benzothiazin-4-yl)ethoxy]phenyl]-2-phenoxy propanoate;

(±) 2-Methyl-3-[4-[2-(2,3-dihydro-1,4-benzothiazin-4-yl)ethoxy]phenyl]-2-phenoxypropanoic acid and its salts;

(+) 2-Methyl-3-[4-[2-(2,3-dihydro-1,4-benzothiazin-4-yl)ethoxy]phenyl]-2-phenoxypropanoic acid and its salts;

(−) 2-Methyl-3-[4-[2-(2,3-dihydro-1,4-benzothiazin-4-yl)ethoxy]phenyl]-2-phenoxypropanoic acid and its salts;

(±) 4-Nitrophenyl 3-[4-[2-(2,3-dihydro-1,4-benzothiazin-4-yl)ethoxy]phenyl]-2-ethoxy propanoate;

(+) 4-Nitrophenyl 3-[4-[2-(2,3-dihydro-1,4-benzothiazin-4-yl)ethoxy]phenyl]-2-ethoxy propanoate;

(−) 4-Nitrophenyl 3-[4-[2-(2,3-dihydro-1,4-benzothiazin-4-yl)ethoxy]phenyl]-2-ethoxy propanoate;

(±) 3-[4-(4-Benzyl-3,4-dihydro-1,4-benzoxazin-2-yl)methoxyphenyl]-2-ethoxypropanoic acid and its salts;

(+) 3-[4-(4-Benzyl-3,4-dihydro-1,4-benzoxazin-2-yl)methoxyphenyl]-2-ethoxypropanoic acid and its salts;

(−) 3-[4-(4-Benzyl-3,4-dihydro-1,4-benzoxazin-2-yl)methoxyphenyl]-2-ethoxypropanoic acid and its salts;

(±) 4-Nitrophenyl-3-[4-(4-benzyl-3,4-dihydro-1,4-benzoxazin-2-yl)methoxyphenyl]-2-ethoxypropanoate;

(+) 4-Nitrophenyl-3-[4-(4-benzyl-3,4-dihydro-1,4-benzoxazin-2-yl)methoxyphenyl]-2-ethoxypropanoate; and (−) 4-Nitrophenyl-3-[4-(4-benzyl-3,4-dihydro-1,4-benzoxazin-2-yl)methoxyphenyl]-2-ethoxypropanoate.

According to a feature of the present invention, the compound of general formula (I) where $R^7$ and $R^5$ together represent a bond, Y represents oxygen atom, $R^1$, $R^2$, $R^3$, $R^4$, $R^5$, $R^6$, $R^9$, $R^{10}$, X, n, m and Ar are as defined earlier, can be prepared by any of the following routes shown in Scheme I.

Scheme-I

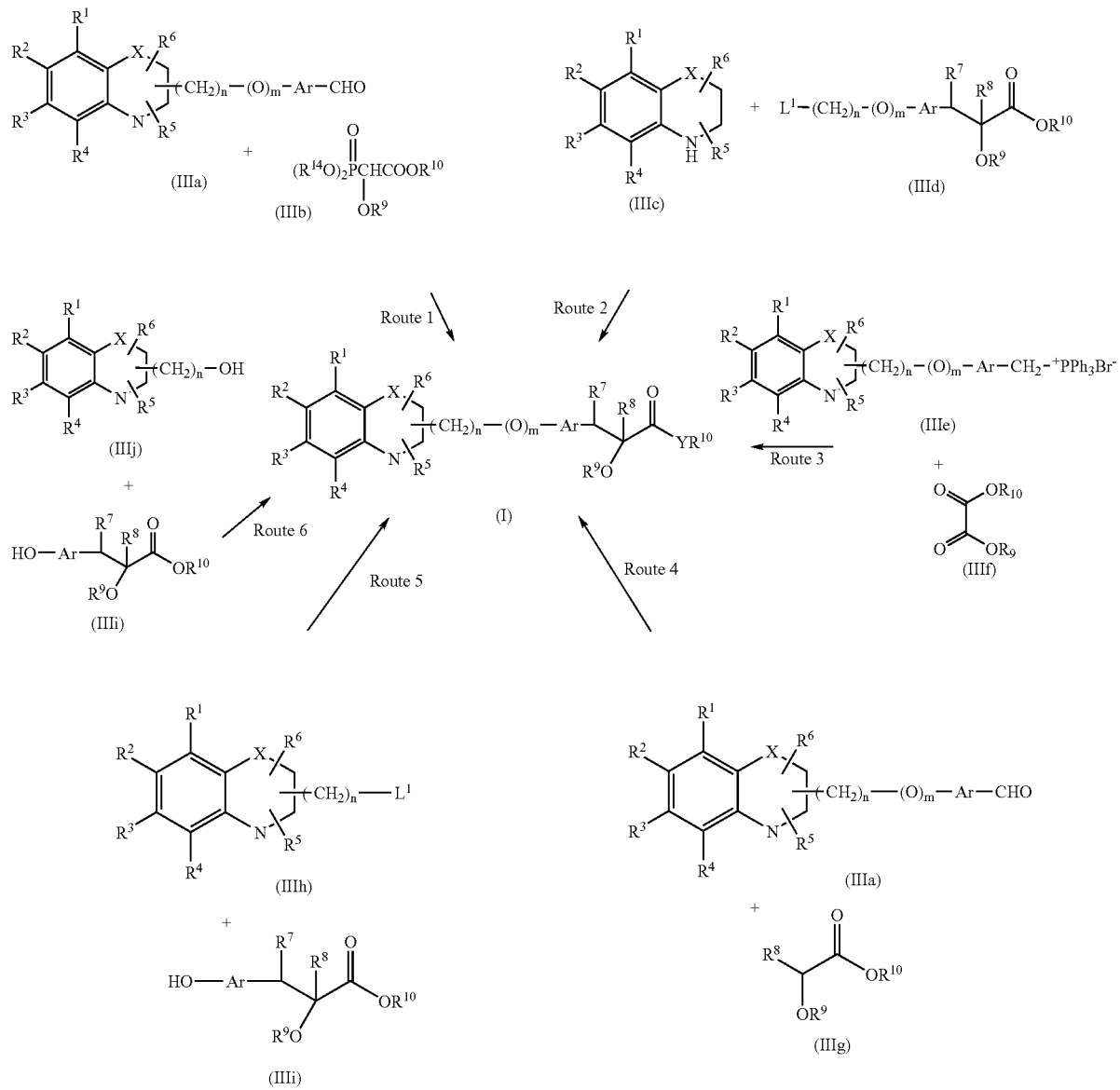

Route (1): The reaction of a compound of the general formula (IIIa) where all symbols are as defined earlier with a compound of formula (IIIb) where $R^9$, $R^{10}$ are as defined earlier excluding hydrogen and $R^{14}$ represents $(C_1-C_6)$alkyl, to yield compound of general formula (I) where $R^7$, $R^5$ together represent a bond and Y represents an oxygen atom may be carried out neat in the presence of a base such as alkali metal hydrides like NaH or KH; organolithiums like $CH_3Li$, BuLi and the like; alkoxides such as NaOMe, NaOEt, $K^+BuO^-$ and the like or mixtures thereof. The reaction may be carried out in the presence of solvents such as THF, dioxane, DMF, DMSO, DME and the like or mixtures thereof. HMPA may be used as cosolvent. The reaction temperature may range from −78° C. to 50° C., preferably at a temperature in the range of −10° C. to 30° C. The reaction is more effective under anhydrous conditions. The compound of general formula (IIIb) may be prepared according to the procedure described in the literature (Annalen. Chemie, (1996) 53, 699).

Alternatively the compound of formula (I) may be prepared by reacting the compound of formula (IIIa) where all symbols are as defined earlier with Wittig reagents such as $Hal^-PPh_3^-CH-(OR^9)CO_2R^{10}$, where $R^9$ and $R^{10}$ are as defined earlier under similar reaction conditions as described above.

Route (2): The reaction of a compound of general formula (Mc) where all symbols are as defined earlier with a compound of general formula (IIId) where $R^7$, $R^9$ together represent a bond, $L^1$ is a leaving group such as halogen atom, p-toluenesulfonate, methanesulfonate, trifluoromethanesulfonate and the like, preferably a halogen atom and all other symbols are as defined earlier to produce a compound of general formula (I) defined above may be carried out in the presence of solvents such as DMSO, DMF, DME, THF, dioxane, ether and the like or a mixture thereof. The reaction may be carried out in an inert atmosphere which may be maintained by using inert gases such as $N_2$, Ar or He. The reaction may be effected in the presence of a base such as alkalis like sodium hydroxide or potassium hydroxide, alkali metal carbonates like sodium carbonate or potassium carbonate; alkali metal hydrides such as sodium hydride or potassium hydride; organometallic bases like n-butyl lithium; alkali metal amides like sodamide or mixtures thereof. The amount of base may range from 1 to 5 equivalents, based on the amount of the compound of formula (IIIc), preferably the amount of base ranges from 1 to 3 equivalents. Phase transfer catalysts such as tetraalkylammonium halide or hydroxide may be added. The reaction may be carried out at a temperature in the range of 0° C. to 150° C., preferably at a temperature in the range of 15° C. to 100° C. The duration of the reaction may range from 0.25 to 48 hours, preferably from 0.25 to 12 hours.

Route (3): The reaction of a compound of formula (IIIe) where all symbols are as defined earlier with a compound of formula (IIIf) where $R^9=R^{10}$ and are as defined earlier excluding hydrogen, to produce a compound of the formula (I) where $R^7$ and $R^8$ together represent a bond and all other symbols are as defined earlier may be carried out neat in the presence of a base such as alkali metal hydrides like NaH or KH; organolithiums like $CH_3Li$, BuLi and the like; alkoxides such as NaOMe, NaOEt, $K^+BuO^-$ and the like or mixtures thereof. The reaction may be carried out in the presence of aprotic solvents such as THF, dioxane, DMF, DMSO, DME and the like or mixtures thereof HMPA may be used as cosolvent. The reaction temperature may range from −78° C. to 100° C., preferably at a temperature in the range of −10° C. to 50° C.

Route (4): The reaction of a compound of the general formula (IIIa) where all symbols are as defined earlier, with a compound of formula (IIIg) where $R^8$ represents hydrogen atom, $R^9$ and $R^{10}$ are as defined earlier may be carried out in the presence of a base. The nature of the base is not critical. Any base normally employed for aldol condensation reaction may be employed; bases like metal hydride such as NaH or KH, metal alkoxides such as NaOMe, $K^+$ BuO$^-$ or NaOEt and the like; metal amides such as $LiNH_2$ or $LiN(iPr)_2$ may be used. Aprotic solvent such as THF, ether, or dioxane may be used. The reaction may be carried out in an inert atmosphere which may be maintained by using inert gases such as $N_2$, Ar, or He and the reaction is more effective under anhydrous conditions. Temperature in the range of −80° C. to 35° C. may be used. The β-hydroxy product initially produced may be dehydrated under conventional dehydration conditions such as treating with p-TSA in solvents such as benzene or toluene. The nature of solvent and dehydrating agent is not critical. Temperature in the range of 20° C. to reflux temperature of the solvent used may be employed, preferably at reflux temperature of the solvent by continuous removal of water using a Dean Stark water separator.

Route (5): The reaction of compound of formula (IIIh) where all symbols are as defined earlier and $L^1$ represents a leaving group such as halogen atom, p-toluenesulfonate, methanesulfonate, trifluoromethanesulfonate and the like with a compound of formula (IIIi) where $R^7$ and $R^8$ together represent a bond and $R^9$, $R^{10}$ and Ar are as defined earlier to produce a compound of the formula (I) where m=1 and all other symbols are as defined above may be carried out in the presence of aprotic solvents such as THF, DMF, DMSO, DME and the like or mixtures thereof. The reaction may be carried out in an inert atmosphere which may be maintained by using inert gases such as $N_2$, Ar or He. The reaction may be effected in the presence of a base such as $K_2CO_3$, $Na_2CO_3$ or NaH or mixtures thereof. Acetone may be used as solvent when $Na_2CO_3$ or $K_2CO_3$ is used as a base. The reaction temperature may range from 0° C.-120° C., preferably at a temperature in the range of 30° C.-100° C. The duration of the reaction may range from 1 to 24 hours, preferably from 2 to 12 hours. The compound of formula (IIIi) can be prepared according to known procedures by a Wittig Horner reaction between the hydroxy protected aryl aldehyde such as benzyloxyaryl aldehyde and compound of formula (IIIb), followed by deprotection.

Route (6): The reaction of compound of general formula (IIIj) where all symbols are as defined earlier with a compound of general formula (IIIi) where $R^7$ and $R^5$ together represent a bond and $R^9$, $R^{10}$ and Ar are as defined earlier to produce a compound of the formula (I) where m=1 and all other symbols are as defined above may be carried out using suitable coupling agents such as dicyclohexyl urea, triarylphosphine/dialkylazadicarboxylate such as $PPh_3$/DEAD and the like. The reaction may be carried out in the presence of solvents such as THF, DME, $CH_2Cl_2$, $CHCl_3$, toluene, acetonitrile, $CCl_4$ and the like. The inert atmosphere may be maintained by using inert gases such as $N_2$, Ar or He. The reaction may be effected in the presence of DMAP, HOBT and they may be used in the range of 0.05 to 2 equivalents, preferably 0.25 to 1 equivalents. The reaction temperature may be in the range of 0° C. to 100° C., preferably at a temperature in the range of 20° C. to 80° C. The duration of the reaction may range from 0.5 to 24 hours, preferably from 6 to 12 hours.

In another embodiment of the present invention, the compound of the general formula (I) where $R^1$, $R^2$, $R^3$, $R^4$, $R^5$, $R^6$, $R^9$, $R^{10}$, X n, m, and Ar are as defined earlier, $R^7$ represents hydrogen atom, hydroxy, alkoxy, halogen, lower alkyl, unsubstituted or substituted aralkyl group, $R^8$ represents hydrogen, hydroxy, alkoxy, halogen, lower alkyl group, acyl or unsubstituted or substituted aralkyl and Y represents oxygen can be prepared by one or more of the processes shown in Scheme-II:

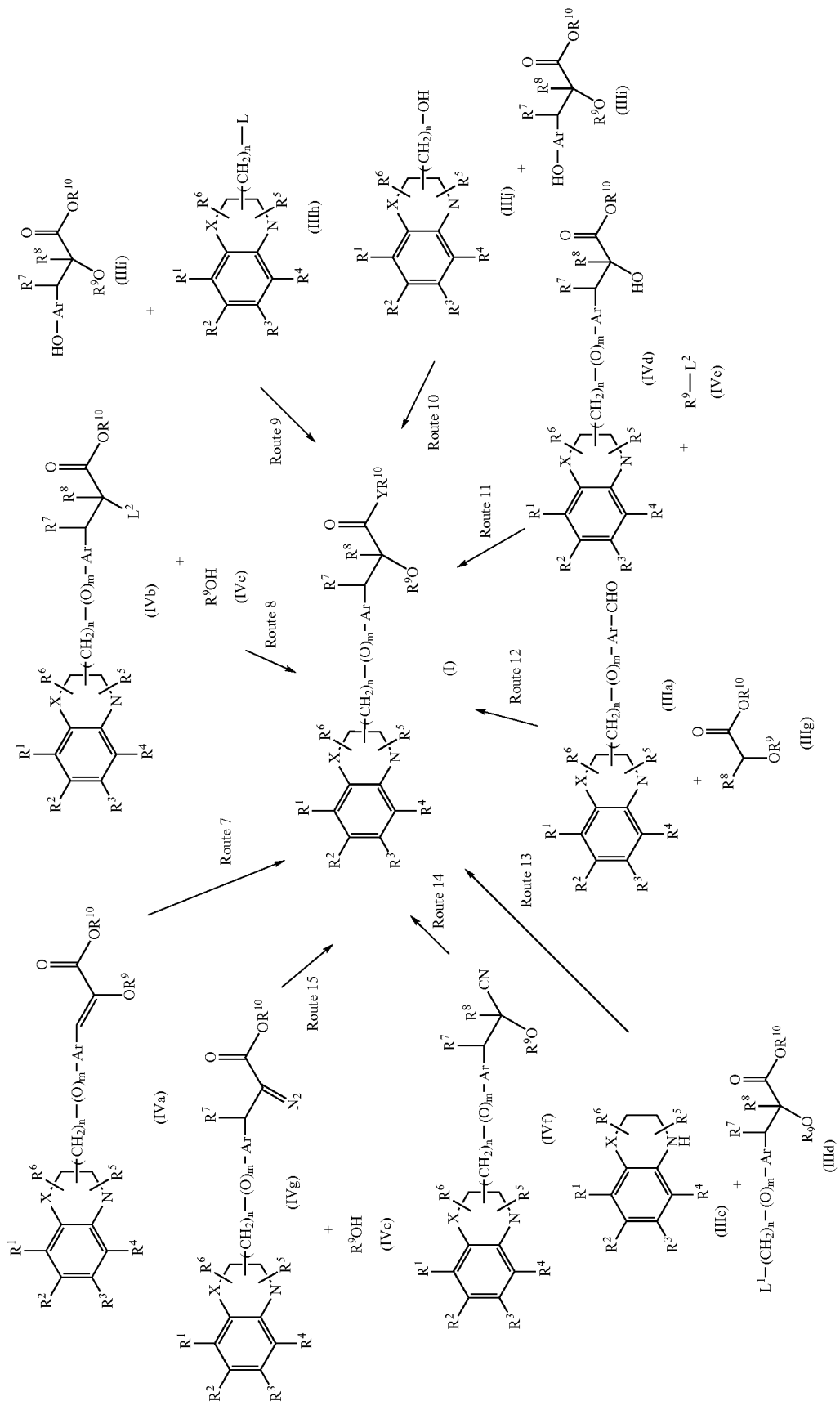

Route 7: The reduction of compound of the formula (IVa) which represents a compound of formula (I) where $R^7$ and $R^8$ together represent a bond and Y represents an oxygen atom and all other symbols are as defined earlier, obtained as described earlier (Scheme-I), to yield a compound of the general formula (I) where $R^7$ and $R^8$ each represent a hydrogen atom and all symbols are as defined earlier, may be carried out in the presence of gaseous hydrogen and a catalyst such as Pd/C, Rh/C, Pt/C, and the like. Mixtures of catalysts may be used. The reaction may also be conducted in the presence of solvents such as dioxane, acetic acid, ethyl acetate and the like. A pressure between atmospheric pressure and 80 psi may be employed. High pressures may be used to reduce the time. The catalyst may be preferably 5-10% Pd/C and the amount of catalyst used may range from 1-50% w/w. The reaction may also be carried out by employing metal solvent reduction such as magnesium in alcohol or sodium amalgam in alcohol preferably methanol. The hydrogenation may be carried out in the presence of metal catalysts containing chiral ligands to obtain a compound of formula (I) in optically active form. The metal catalyst may contain rhodium, ruthenium, indium and the like. The chiral ligands may preferably be chiral phosphines such as (2S,3S)-bis(diphenylphosphino)butane, 1,2-bis (diphenylphosphino)ethane, 1,2-bis(2-methoxyphenylphe- nylphosphino)ethane, (−)-2,3-isopropylidene-2,3-dihy- droxy-1,4-bis(diphenylphosphino)butane and the like. Any suitable chiral catalyst may be employed which would give required optical purity of the product (I) (Ref: Principles of Asymmetric Synthesis, Tet. Org. Chem. Series Vol 14, pp 311-316, Ed. Baldwin J. E.).

Route 8: The reaction of compound of formula (IVb) where $R^{10}$ is as defined earlier excluding hydrogen, $L^2$ is a leaving group such as halogen atom and all other symbols are as defined earlier with an alcohol of general formula (IVc), where $R^9$ is as defined earlier excluding hydrogen to produce a compound of the formula (I) defined earlier may be carried out in the presence of solvents such as THF, DMF, DMSO, DME and the like or mixtures thereof. The reaction may be carried out in an inert atmosphere which may be maintained by using inert gases such as $N_2$, Ar or He. The reaction may be effected in the presence of a base such as KOH, NaOH, NaOMe, NaOEt, $K^+BuO^-$ or NaH or mixtures thereof. Phase transfer catalysts such as tetraalkylammo- nium halides or hydroxides may be employed. The reaction temperature may range from 20° C.-120° C., preferably at a temperature in the range of 30° C.-100° C. The duration of the reaction may range from 1 to 12 hours, preferably from 2 to 6 hours. The compound of general formula (IVb) and its preparation has been disclosed in our International publica- tion No. WO 98/52946.

Route 9: The reaction of compound of formula (IIIh) defined earlier with compound of formula (IIIi) where all symbols are as defined earlier to produce a compound of the formula (I) where m=1 and all other symbols are as defined above, may be carried out in the presence of solvents such as THF, DMF, DMSO, DME and the like or mixtures thereof. The reaction may be carried out in an inert atmo- sphere which is maintained by using inert gases such as $N_2$, Ar or He. The reaction may be effected in the presence of a base such as $K_2CO_3$, $Na_2CO_3$, NaH and the like or mixtures thereof. Acetone may be used as a solvent when $K_2CO_3$ or $Na_2CO_3$ is used as a base. The reaction temperature may range from 20° C.-120° C., preferably at a temperature in the range of 30° C.-80° C. The duration of the reaction may range from: 1 to 24 hours, preferably from 2 to 12 hours. The compound of formula (IIIi) may be prepared by Wittig Horner reaction between the protected hydroxyaryl alde- hyde and compound of formula (IIIb) followed by reduction of the double bond and deprotection. Alternatively, the compound of formula (IIIi) may be prepared by following a procedure disclosed in WO 94/01420.

Route 10: The reaction of compound of general formula (mj) defined earlier with a compound of general formula (IIIi) where all symbols are as defined earlier to produce a compound of the formula (I) where m=1 and all other symbols are as defined above may be carried out using suitable coupling agents such as dicyclohexyl urea, tri- arylphosphine/dialkylazadicarboxylate such as $PPh_3$/DEAD and the like. The reaction may be carried out in the presence of solvents such as THF, DME, $CH_2Cl_2$, $CHCl_3$, toluene, acetonitrile, carbon tetrachloride and the like. The reaction may be carried out in an inert atmosphere which may be maintained by using inert gases such as $N_2$, Ar or He. The reaction may be effected in the presence of DMAP, HOBT and they may be used in the range of 0.05 to 2 equivalents, preferably 0.25 to 1 equivalents. The reaction temperature may be in the range of 0° C. to 100° C., preferably at a temperature in the range of 20° C. to 80° C. The duration of the reaction may range from 0.5 to 24 hours, preferably from 6 to 12 hours.

Route 11: The reaction of compound of formula (IVd) which represents a compound of formula (I) where $R^9$ represents hydrogen atom and all other symbols are as defined earlier with a compound of formula (IVe) where $R^9$ is as defined earlier excluding hydrogen and $L^2$ is a leaving group such as a halogen atom, may be carried out in the presence of solvents such as TH, DMF, DMSO, DME and the like. The reaction may carried out in an inert atmosphere which may be maintained by using inert gases such as $N_2$, Ar or He. The reaction may be effected in the presence of a base such as KOH, NaOH, NaOMe, $K^+BuO^-$, NaH and the like. Phase transfer catalyst such as tetraalkylammonium halides or hydroxides may be employed. The reaction tem- perature may range from 20° C. to 150° C., preferably at a temperature in the range of 30° C. to 100° C. The duration of the reaction may range from 1 to 24 hours, preferably from 2 to 6 hours.

Route 12: The reaction of a compound of the general formula (IIIa) as defined above with a compound of formula (IIIg) where $R^8$ is hydrogen, $R^9$, and $R^{10}$ are as defined earlier may be carried out under conventional conditions. The base is not critical. Any base normally employed for aldol condensation reaction may be employed, metal hydride such as NaH or KH; metal alkoxides such as NaOMe, $K^tBuO^-$ or NaOEt; metal amides such as $LiNH_2$, or $LiN(iPr)_2$. Aprotic solvent such as THF may be used. Inert atmosphere may be employed such as argon and the reaction is more effective under anhydrous conditions. Temperature in the range of −80° C. to 25° C. may be used. The β-hydroxy aldol product may be dehydroxylated using con- ventional methods, conveniently by ionic hydrogenation technique such as by treating with a trialkyl silane in the presence of an acid such as trifluoroacetic acid. Solvent such as $CH_2Cl_2$ may be used. Favorably, the reaction proceeds at 25° C. A higher temperature may be employed if the reaction is slow.

Route 13: The reaction of a compound of general formula (IIIc) where all symbols are as defined earlier with a compound of general formula (IIId) where $L^1$ is a leaving group such as halogen atom, p-toluenesulfonate, methane- sulfonate, trifluoromethane-sulfonate and the like, prefer- ably $L^1$ is a halogen atom, and all other symbols are as defined earlier to produce a compound of general formula (I) may be carried out in the presence of solvents such as DMSO, DMF, DME, THF, dioxane, ether and the like or mixtures thereof. The reaction may be carried out in an inert atmosphere which may be maintained by using inert gases such as $N_2$, Ar or He. The reaction may be effected in the presence of a base such as alkalis like sodium hydroxide, potassium hydroxide and the like; alkali metal carbonates like sodium carbonate, potassium carbonate and the like; alkali metal hydrides such as sodium hydride or potassium hydride; organometallic bases like n-butyl lithium; alkali metal amides like sodamide or mixtures thereof. The amount of base may range from 1 to 5 equivalents, based on the amount of the compound of formula (IIIc), preferably the amount of base ranges from 1 to 3 equivalents. The reaction may be carried out at a temperature in the range of 0° C. to 150° C., preferably at a temperature in the range of 15° C. to 100° C. The duration of the reaction may range from 0.25 to 24 hours, preferably from 0.25 to 12 hours.

Route 14: The conversion of compound of formula (IVf) where all symbols are as defined earlier to a compound of formula (I) where all symbols are as defined earlier may be carried out either in the presence of base or acid and the selection of base or acid is not critical. Any base normally used for hydrolysis of nitrile to acid may be employed, such as metal hydroxides such as NaOH or KOH in an aqueous solvent or any acid normally used for hydrolysis of nitrile to ester may be employed such as dry HCl in excess of alcohol such as methanol, ethanol, propanol and the like. The reaction may be carried out at a temperature in the range of 0° C. to reflux temperature of the solvent used, preferably at a temperature in the range of 25° C. to reflux temperature of the solvent used. The duration of the reaction may range from 0.25 to 48 hrs.

Route 15: The reaction of a compound of formula (IVg) where $R^{10}$ is as defined earlier excluding hydrogen and all other symbols are as defined earlier with a compound of formula (IVc) where $R^9$ is as defined earlier excluding hydrogen to produce a compound of formula (I) (by a rhodium carbenoid mediated insertion reaction) may be carried out in the presence of rhodium (II) salts such as rhodium (II) acetate. The reaction may be carried out in the presence of solvents such as benzene, toluene, dioxane, ether, THF and the like or mixtures thereof or when practicable in the presence of $R^9OH$ as solvent at any temperature providing a convenient rate of formation of the required product, generally at an elevated temperature, such as reflux temperature of the solvent. The inert atmosphere may be maintained by using inert gases such as $N_2$, Ar or He. The duration of the reaction may range from 0.5 to 24 h, preferably from 0.5 to 6 h.

The compound of formula (I) where $R^{10}$ represents hydrogen atom may be prepared by hydrolysing, using conventional methods, a compound of formula (I) where $R^{10}$ represents all groups defined earlier excluding hydrogen. The hydrolysis may be carried out in the presence of a base such as $Na_2CO_3$ and a suitable solvent such as methanol, ethanol and the like or mixtures thereof. The reaction may be carried out at a temperature in the range of 20° C.-40° C., preferably at 25° C.-30° C. The reaction time may range from 2 to 12 h, preferably from 4 to 8 h.

The compound of general formula (I) where Y represents oxygen and $R^{10}$ represents hydrogen or lower alkyl group may be converted to compound of formula (I), where Y represents $NR^{12}$ by reaction with appropriate amines of the formula $NHR^{10}R^{12}$, where $R^{10}$ and $R^{12}$ are as defined earlier to yield a compound of formula (I) where Y represents $NR^{12}$ and all other symbols are as defined earlier. Alternatively, the compound of formula (I) where $YR^{10}$ represents OH may be converted to acid halide, preferably $YR^{10}$=Cl, by reacting with appropriate reagents such as oxalyl chloride, thionyl chloride and the like, followed by treatment with amines of the formula $NHR^{10}R^{12}$ where $R^{11}$ and $R^{12}$ are as defined earlier. Alternatively, mixed anhydrides may be prepared from compound of formula (I) where $YR^{10}$ represents OH and all other symbols are as defined earlier by treating with acid halides such acetyl chloride, acetyl bromide, pivaloyl chloride, dichlorobenzoyl chloride and the like. The reaction may be carried out in the presence of suitable base such as pyridine, triethylamine, diisopropyl ethylamine and the like. Solvents such as halogenated hydrocarbons like $CHCl_3$ or $CH_2Cl_2$; hydrocarbons such as benzene, toluene, xylene and the like may be used. The reaction may be carried out at a temperature in the range of 40° C. to 40° C., preferably at a temperature in the range of 0° C. to 20° C. The acid halide or mixed anhydride thus prepared may further be treated with appropriate amines of the formula $NHR^{10}R^{12}$ where $R^{10}$ and $R^{12}$ are as defined earlier to yield a compound of formula (I) where Y represents $NR^{12}$ and all other symbols are as defined earlier.

The process for the preparation of compounds of formula (IIIa) have been described in our International publication No. WO 98/52946.

In another embodiment of the present invention the novel intermediate of formula (IVf)

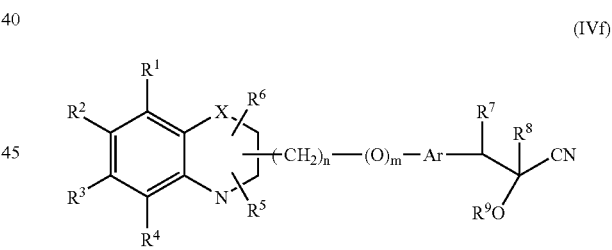

(IVf)

wherein the groups $R^1$, $R^2$, $R^3$, $R^4$ and the groups $R^5$ and $R^6$ when attached to carbon atom, may be same or different and represent hydrogen, halogen, hydroxy, nitro, cyano, formyl or unsubstituted or substituted groups selected from alkyl, cycloalkyl, alkoxy, cycloalkoxy, aryl, aryloxy, aralkyl, aralkoxy, heterocyclyl, heteroaryl, heteroaralkyl, heteroaryloxy, heteroaralkoxy, acyl, acyloxy, amino, acylamino, monoalkylamino, dialkylamino, arylamino, aralkylamino, alkoxycarbonyl, aryloxycarbonyl, aralkoxycarbonyl, alkylthio, alkoxycarbonylamino, aryloxycarbonylamino, aralkoxycarbonylamino, carboxylic acid or its derivatives, or sulfonic acid or its derivatives; one or both of $R^5$ and $R^6$ may also represent an oxo group when they are attached to carbon atom; $R^5$ and $R^6$ when attached to nitrogen atom represent hydrogen, hydroxy, formyl or unsubstituted or substituted groups selected from alkyl, cycloalkyl, alkoxy, cycloalkoxy, aryl, aralkyl, heterocyclyl, heteroaryl, heteroaralkyl, acyl, acyloxy, amino, acylamino, monoalkylamino, dialkylamino, arylamino, aralkylamino, aryloxy, aralkoxy, heteroaryloxy, heteroaralkoxy, alkoxycarbonyl, aryloxycarbonyl, aralkoxycarbonyl, alkylthio groups, carboxylic acid derivatives, or sulfonic acid derivatives; X represents a heteroatom selected from oxygen, sulfur or $NR^{11}$ where $R^{11}$ represents hydrogen or unsubstituted or substituted groups selected from alkyl, cycloalkyl, aryl, aralkyl, acyl, alkoxycarbonyl, aryloxycarbonyl or aralkoxycarbonyl groups; Ar represents an unsubstituted or substituted divalent single or fused aromatic or heterocyclic group; $R^7$ represents hydrogen atom, hydroxy, alkoxy, halogen, lower alkyl, unsubstituted or substituted aralkyl group or forms a bond together with the adjacent group $R^8$; $R^8$ represents hydrogen, hydroxy, alkoxy, halogen, lower alkyl group, acyl or unsubstituted or substituted aralkyl or $R^8$ forms a bond together with $R^7$; $R^9$ represents hydrogen or unsubstituted or substituted groups selected from alkyl, cycloalkyl, aryl, aralkyl, alkoxycarbonyl, aryloxycarbonyl, alkylaminocarbonyl, arylaminocarbonyl, acyl, heterocyclyl, heteroaryl or heteroaralkyl groups; the linking group represented by —$(CH_2)_n$—$(O)_m$— may be attached either through nitrogen atom or carbon atom; n is an integer ranging from 1-4 and m is an integer 0 or 1 and a process for its preparation and its use in the preparation of β-aryl-α-oxysubstituted alkylcarboxylic acids is provided.

The compound of formula (IVf) where $R^7$ and $R^8$ each represent hydrogen atoms and all other symbols are as defined earlier is prepared by a process outlined in Scheme-III.

such as THF, DMSO, dioxane, DME and the like may be used. Mixture of solvents may be used. HMPA may be used as a cosolvent. Inert atmosphere may be employed which may be maintained by using inert gases such as argon and the reaction is more effective under anhydrous conditions. Temperature in the range of –80° C. to 100° C. may be used.

The compound of (IVi) where all symbols are as defined earlier and $R^9$ is as defined earlier excluding hydrogen may be converted to a compound of formula (IVj) where $R^7$ and $R^9$ represent hydrogen atoms and all other symbols are as defined earlier, by treating with an alcohol of formula $R^9OH$ where $R^9$ is as defined earlier excluding hydrogen under anhydrous conditions in the presence of a strong anhydrous acid such as p-toluenesulfonic acid.

The compound of formula (IVj) defined above upon treatment with trialkylsilyl cyanide such as trimethylsilyl cyanide produces a compound of formula (IVf) where $R^7$ and $R^8$ represent hydrogen atoms, $R^9$ is as defined earlier excluding hydrogen and all other symbols are as defined earlier.

In still another embodiment of the present invention the novel intermediate of formula (IVg)

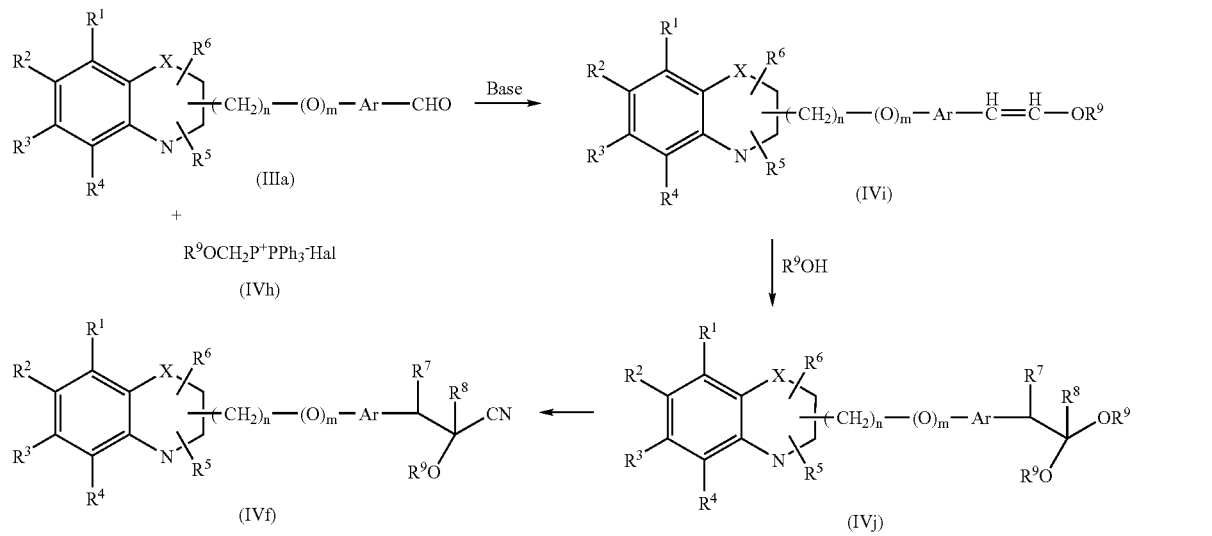

The reaction of a compound of formula (IIIa) where all symbols are as defined earlier with a compound of formula (IVh) where $R^9$ is as defined earlier excluding hydrogen and Hal represents a halogen atom such as Cl, Br or I to produce a compound of formula (IVi) may be carried out under conventional conditions in the presence of a base. The base is not critical. Any base normally employed for Wittig reaction may be employed, metal hydride such as NaH or KH; metal alkoxides such as NaOMe, K′BuO⁻, or NaOEt or metal amides such as $LiNH_2$ or $LiN(iPr)_2$. Aprotic solvent

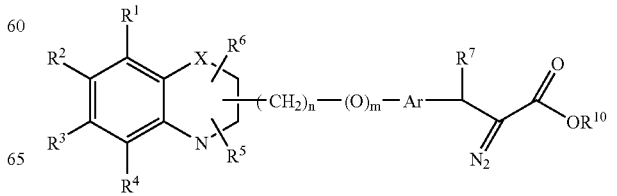

wherein the groups $R^1$, $R^2$, $R^3$, $R^4$ and the groups $R^5$ and $R^6$ when attached to carbon atom, may be same or different and represent hydrogen, halogen, hydroxy, nitro, cyano, formyl or unsubstituted or substituted groups selected from alkyl, cycloalkyl, alkoxy, cycloalkoxy, aryl, aryloxy, aralkyl, aralkoxy, heterocyclyl, heteroaryl, heteroaralkyl, heteroaryloxy, heteroaralkoxy, acyl, acyloxy, amino, acylamino, monoalkylamino, dialkylamino, arylamino, aralkylamino, alkoxycarbonyl, aryloxycarbonyl, aralkoxycarbonyl, alkylthio, alkoxycarbonylamino, aryloxycarbonylamino, aralkoxycarbonylamino, carboxylic acid or its derivatives, or sulfonic acid or its derivatives; one or both of $R^5$ and $R^6$ may also represent an oxo group when they are attached to carbon atom; $R^5$ and $R^6$ when attached to nitrogen atom represent hydrogen, hydroxy, formyl or unsubstituted or substituted groups selected from alkyl, cycloalkyl, alkoxy, cycloalkoxy, aryl, aralkyl, heterocyclyl, heteroaryl, heteroaralkyl, acyl, acyloxy, amino, acylamino, monoalkylamino, dialkylamino, arylamino, aralkylamino, aryloxy, aralkoxy, heteroaryloxy, heteroaralkoxy, alkoxycarbonyl, aryloxycarbonyl, aralkoxycarbonyl, alkylthio groups, carboxylic acid derivatives, or sulfonic acid derivatives; X represents a heteroatom selected from oxygen, sulfur or $NR^{11}$ where $R^{11}$ represents hydrogen or unsubstituted or substituted groups selected from alkyl, cycloalkyl, aryl, aralkyl, acyl, alkoxycarbonyl, aryloxycarbonyl or aralkoxycarbonyl groups; Ar represents an unsubstituted or substituted divalent single or fused aromatic or heterocyclic group; $R^7$ represents hydrogen atom, hydroxy, alkoxy, halogen, lower alkyl, unsubstituted or substituted aralkyl group; $R^{10}$ represents hydrogen or unsubstituted or substituted groups selected from alkyl, cycloalkyl, aryl, aralkyl, heterocyclyl, heteroaryl or heteroaralkyl groups; the linking group represented by $-(CH_2)_n-(O)_m-$ may be attached either through nitrogen atom or carbon atom; n is an integer ranging from 1-4 and m is an integer 0 or 1 and a process for its preparation and its use in the preparation of β-aryl-α-oxysubstituted alkylcarboxylic acids is provided.

The compound of formula (IVg) where all other symbols are as defined earlier may be prepared by reacting a compound of formula (IVk)

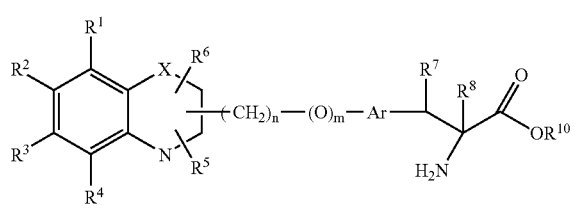

(IVk)

where $R^5$ is a hydrogen atom and all symbols are as defined earlier, with an appropriate diazotizing agent.

The diazotization reaction may be carried out under conventional conditions. A suitable diazotizing agent is an alkyl nitrile, such as iso-amyl nitrile. The reaction may be carried out in presence of solvents such as THF, dioxane, ether, benzene and the like or a mixture thereof. Temperature in the range of −50° C. to 80° C. may be used. The reaction may be carried out in an inert atmosphere which may be maintained by using inert gases such as $N_2$, Ar or He. The duration of the reaction may range from 1 to 24 h, preferably, 1 to 12 h.

The compound of formula (IVk) may also be prepared by a reaction between (IIIh) where all symbols are as defined earlier and a compound of formula (IVl)

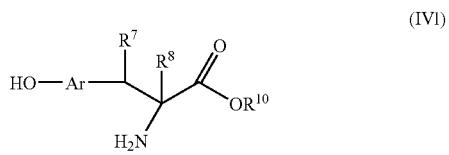

(IVl)

where $R^5$ is a hydrogen atom and all other symbols are as defined earlier.

The reaction of compound of formula (IIIh) where all symbols are as defined earlier and a compound of formula (IVl) where all symbols are as defined earlier may be carried out in the presence of solvents such as THF, DMF, DMSO, DME and the like or mixtures thereof. The reaction may be carried out in an inert atmosphere which is maintained by using inert gases such as $N_2$, Ar or He. The reaction may be effected in the presence of a base such as $K_2CO_3$, $Na_2CO_3$ or NaH or mixtures thereof. Acetone may be used as a solvent when $K_2CO_3$ or $Na_2CO_3$ is used as a base. The reaction temperature may range from 20° C.-120° C., preferably at a temperature in the range of 30° C.-80° C. The duration of the reaction may range from 1 to 24 hours, preferably from 2 to 12 hours.

As used in this application the term neat means the reaction is carried out without the use of solvent.

It is appreciated that in any of the above mentioned reactions, any reactive group in the substrate molecule may be protected according to conventional chemical practice. Suitable protecting groups in any of the above mentioned reactions are those used conventionally in the art. The methods of formation and removal of such protecting groups are those conventional methods appropriate to the molecule being protected.

The pharmaceutically acceptable salts are prepared by reacting the compound of formula (I) with 1 to 4 equivalents of a base such as sodium hydroxide, sodium methoxide, sodium hydride, potassium hydroxide, potassium t-butoxide, calcium hydroxide, magnesium hydroxide and the like, in solvents like ether, THF, methanol, t-butanol, dioxane, isopropanol, ethanol etc. Mixtures of solvents may be used. Organic bases like lysine, arginine, diethanolamine, choline, guanidine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid, salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixtures of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, and the like wherever applicable or chiral bases such as brucine, cinchona alkaloids and their derivatives and the like. Commonly used methods are compiled by Jaques et al in "Enantiomers, Racemates and Resolution" (Wiley Interscience, 1981). More specifically the compound of formula (I) where $YR^{10}$ represents OH may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula (I) may be prepared by hydrolyzing the pure diastereomeric amide.

Various polymorphs of a compound of general formula (I) forming part of this invention may be prepared by crystallization of compound of formula I) under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffraction or such other techniques.

The present invention provides a pharmaceutical composition, containing the compounds of the general formula (I) as defined above, their derivatives, their analogs, their tautomeric forms, their stereoisomers, their polymorphs, their pharmaceutically acceptable salts or their pharmaceutically acceptable solvates in combination with the usual pharmaceutically employed carriers, diluents and the like, useful for the treatment and/or prophylaxis of diseases such as hypertension, coronary heart disease, atherosclerosis, stroke, peripheral vascular diseases and related disorders. These compounds are useful for the treatment of familial hypercholesterolemia, hypertriglyceridemia, lowering of atherogenic lipoproteins, VLDL and LDL. The compounds of the present invention can be used for the treatment of certain renal diseases including glomerulonephritis, glomerulosclerosis, nephrotic syndrome, hypertensive nephrosclerosis, nephropathy. The compounds of general formula (I) are also useful for the treatment/prophylaxis of insulin resistance (type II diabetes), leptin resistance, impaired glucose tolerance, dyslipidemia, disorders related to syndrome X such as hypertension, obesity, insulin resistance, coronary heart disease, and other cardiovascular disorders. These compounds may also be useful as aldose reductase inhibitors, for improving cognitive functions in dementia, as inflammatory agents, treating diabetic complications, disorders related to endothelial cell activation, psoriasis, polycystic ovarian syndrome (PCOS), inflammatory bowel diseases, osteoporosis, myotonic dystrophy, pancreatitis, retinopathy, arteriosclerosis, xanthoma and for the treatment of cancer. The compounds of the present invention are useful in the treatment and/or prophylaxis of the above said diseases in combination/concomitant; with one or more HMG CoA reductase inhibitors, hypolipidemic/hypolipoproteinemic agents such as fibric acid derivatives, nicotinic acid, cholestyramine, colestipol, probucol or their combination. The compounds of the present invention in combination with HMG CoA reductase inhibitors, hypolipidemic/hypolipoproteinemic agents can be administered together or within such a period to act synergistically. The HMG CoA reductase inhibitors may be selected from those used for the treatment or prevention of hyperlipidemia such as lovastatin, provastatin, simvastatin, fluvastatin, atorvastatin, cerivastatin and their analogs thereof. Suitable fibric acid derivative may be gemfibrozil, clofibrate, fenofibrate, ciprofibrate, benzafibrate and their analogs thereof.

The present invention also provides a pharmaceutical composition, containing the compounds of the general formula (I) as defined above, their derivatives, their analogs, their tautomeric forms, their stereoisomers, their polymorphs, their pharmaceutically acceptable salts or their pharmaceutically acceptable solvates and one or more HMG CoA reductase inhibitors, hypolipidemic/hypolipoproteinemic agents such as fibric acid derivatives, nicotinic acid, cholestyramine, colestipol, probucol in combination with the usual pharmaceutically employed carriers, diluents and the like.

The pharmaceutical composition may be in the forms normally employed, such as tablets, capsules, powders, syrups, solutions, suspensions and the like, may contain flavorants, sweeteners etc. in suitable solid or liquid carriers or diluents, or in suitable sterile media to form injectable solutions or suspensions. Such compositions typically contain from 1 to 20%, preferably 1 to 10% by weight of active compound, the remainder of the composition being pharmaceutically acceptable carriers, diluents or solvents.

Suitable pharmaceutically acceptable carriers include solid fillers or diluents and sterile aqueous or organic solutions. The active ingredient will be present in such pharmaceutical compositions in the amounts sufficient to provide the desired dosage in the range as described above. Thus, for oral administration, the polymorphic form can be combined with a suitable solid or liquid carrier or diluent to form capsules, tablets, powders, syrups, solutions, suspensions and the like. The pharmaceutical compositions, may, if desired, contain additional components such as flavourants, sweeteners, excipients and the like. For parenteral administration, the polymorphic form can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or salts with base of the compounds. Aqueous solutions with the active ingredient dissolved in polyhydroxylated castor oil may also be used for injectable solutions. The injectable solutions prepared in this manner can then be administered intravenously, intraperitoneally, subcutaneously, or intramuscularly, with intramuscular administration being preferred in humans.

For nasal administration, the preparation may contain the polymorphic forms of the present invention dissolved or suspended in a liquid carrier, in particular an aqueous carrier, for aerosol application. The carrier may contain additives such as solubilizing agents, such as propylene glycol, surfactants, absorption enhancers such as lecithin (phosphatidylcholine) or cyclodextrin or preservatives such as parabenes.

Tablets, dragees or capsules having talc and/or a carbohydrate carried binder or the like are particularly suitable for any oral application. Preferably, carriers for tablets, dragees or capsules include lactose, corn starch and/or potato starch. A syrup or elixir can be used in cases where a sweetened vehicle can be employed.

A typical tablet production method is exemplified below:

Tablet Production Example:

| a) | | | |
|---|---|---|---|
| | 1) | Active ingredient | 30 g |
| | 2) | Lactose | 95 g |
| | 3) | Corn starch | 30 g |
| | 4) | Carboxymethyl cellulose | 44 g |
| | 5) | Magnesium stearate | 1 g |
| | | | 200 g for 1000 tablets |

The ingredients 1 to 3 are uniformly blended with water and granulated after drying under reduced pressure. The ingredient 4 and 5 are mixed well with the granules and compressed by a tabletting machine to prepare 1000 tablets each containing 30 mg of active ingredient.

| b) | | | |
|---|---|---|---|
| | 1) Active ingredient | 30 g | |
| | 2) Calcium phosphate | 90 g | |
| | 3) Lactose | 40 g | |
| | 4) Corn starch | 35 g | |
| | 5) Polyvinyl pyrrolidone | 3.5 g | |
| | 6) Magnesium stearate | 1.5 g | |
| | | 200 g for 1000 tablets | |

The ingredients 1-4 are uniformly moistened with an aqueous solution of 5 and granulated after drying under reduced pressure. Ingredient 6 is added and granules are compressed by a tabletting machine to prepare 1000 tablets containing 30 mg of ingredient 1.

The compound of the formula (I) as defined above are clinically administered to mammals, including man, via either oral, nasal, pulmonary, transdermal or parenteral, rectal, depot, subcutaneous, intravenous, intraurethral, intramuscular, intranasal, ophthalmic solution or an ointment. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.01 to about 100 mg/kg body weight of the subject per day or preferably about 0.01 to about 30 mg 1 kg body weight per day administered singly or as a divided dose. However, the optimum dosage for the individual subject being treated will be determined by the person responsible for treatment, generally smaller doses being administered initially and thereafter increments made to determine the most suitable dosage.

The invention is explained in detail in the examples given below which are provided by way of illustration only and therefore should not be construed to limit the scope of the invention.

Preparation 1

(±) 4-[2-(3-Oxo-2H-1,4-benzoxazin-4-yl)ethoxy]benzaldehyde

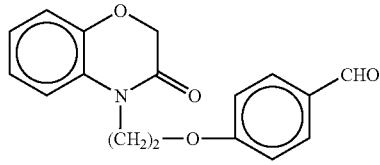

A mixture of 2H-1,4-benzoxazin-3-(4H)-one (1.6 g, 10.7 mmol), 4-(2-bromoethoxy)benzaldehyde (2.95 g, 12.8 mmol) and potassium carbonate (5.93 g, 42.97 mmol) in dry dimethyl formamide (30 mL) was stirred at 80° C. for 10 h. Water (100 mL) was added and extracted with ethyl acetate (2×75 mL). The combined organic layers were washed with water (50 mL), brine (50 mL), dried (Na$_2$SO$_4$) and the solvent was evaporated. The residue was chromatographed over silica gel using a mixture of ethyl acetate and pet ether (2:8) to afford the title compound (2.9 g, 91%) as a colorless solid. mp: 75-78° C.

$^1$H NMR (CDCl$_3$, 200 MHz): δ 4.37 (s, 4H), 4.62 (s, 2H), 6.96-7.26 (complex, 6H), 7.82 (d, J=8.40 Hz, 2H), 9.89 (s, 1H).

Preparation 2

(±) 6-[2-(2,3-Dihydro-1,4-benzothiazin-4-yl)ethoxy]cyanonaphthalene

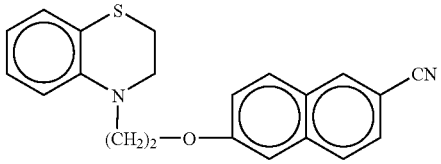

A mixture of 2-(2,3-dihydro-1,4-benzothiazin-4-yl)ethyl methanesulfonate (0.49 g, 1.82 mmol), 2-hydroxy-6-cyanonaphthalene (0.28 g, 1.65 mmol) and potassium carbonate (1.15 g, 8.28 mmol) in dry dimethyl formamide (15 mL) was stirred at 80° C. for 12 h. Water (50 mL) was added and extracted with ethyl acetate (2×25 mL). The combined ethyl acetate layers were washed with water (25 mL), brine (20 mL), dried (Na$_2$SO$_4$), filtered and the solvent was evaporated under reduced pressure. The residue was chromatographed over silica gel using a mixture of ethyl acetate and pet. ether to afford the title compound (0.41 g, 72%) as a pale yellow solid. mp: 94-96° C.

$^1$H NMR (CDCl$_3$, 200 MHz): δ 3.05 (t, J=5.21 Hz, 2H), 3.79-3.85 (complex, 4H), 4.31 (t, J=5.82 Hz, 2H), 6.64-6.78 (complex, 2H), 6.97-7.25 (complex, 4H), 7.53-7.80 (complex, 3H), 8.13 (s, 1H).

Preparation 3

(±) 6-[2-(2,3-Dihydro-1,4-benzothiazin-4-yl)ethoxy]naphthaldehyde

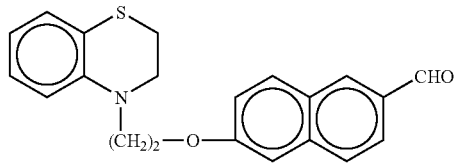

To a solution of (±) 6-[2-2,3-dihydro-1,4-benzothiazin-4-yl)ethoxy]cyanonaphthalene (8 g, 22.9 mmol) obtained in preparation 2 in dry tetrahydrofuran (15 mL) was added diisobutyl aluminum hydride (93 mL, 20% in toluene) at −70° C. over a period of 1 h. After complete addition, the reaction mixture was stirred at 25° C. for 16 h. At the end of this time, ethyl formate (20 mL) was added and stirred for 1 h at 25° C. Saturated ammonium chloride solution (15 mL) was added. The reaction mixture was acidified with 10% sulphuric acid and extracted with ethyl acetate (2×75 mL). The combined ethyl acetate layers were washed with water (2×50 mL), brine (50 mL), dried (Na$_2$SO$_4$), filtered and the solvent was evaporated under reduced pressure. The residue was chromatographed over silica gel using a mixture of ethyl acetate and pet. ether (10:90) to afford the title compound (4.5 g, 56%) as a pale yellow solid. mp: 100-102° C.

$^1$H NMR (CDCl$_3$, 200 MHz): δ 3.06 (t, J=5.20 Hz, 2H), 3.72-3.86 (complex, 4H), 4.33 (t, J=5.67 Hz, 2H), 6.60-6.79 (complex, 2H), 6.97-7.25 (complex, 4H), 7.74-7.93 (complex, 3H), 8.25 (s, 1H), 10.09 (s, 1H).

Preparation 4

(±)4-[4-Methyl-3,4-dihydro-1,4-benzoxazin-2-yl]methoxybenzaldehyde

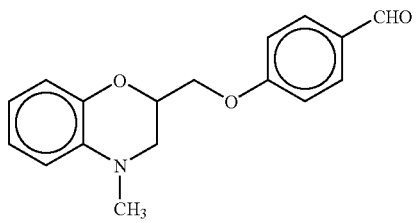

To a solution of 4-methyl-3,4-dihydro-1,4-benzoxazin-2-methanol (6.0 g, 33.51 mmol) in dichloromethane (20 mL) was added triethylamine (10.15 g, 100.5 mmol) under nitrogen atmosphere at 25° C. Methanesulfonyl chloride (5.75 g, 50.25 mmol) was added to the above reaction mixture at 0° C. and stirred for 10 h at 25° C. Water (50 mL) was added and extracted with chloroform (2×25 mL). The combined organic extracts were washed with water (50 mL), dried ($Na_2SO_4$), filtered and the solvent was evaporated under reduced pressure. The residue was chromatographed over silica gel using a mixture of ethyl acetate and hexane (2:8) to yield (4-methyl-3,4-dihydro-2H-1,4-benzoxazin-2-yl)methyl methanesulfonate (3.7 g, 43%) as a syrup.

$^1$H NMR (CDCl$_3$, 200 MHz): δ 2.88 (s, 3H), 3.07 (s, 3H), 3.13-3.31 (complex, 2H), 4.41 (d, J=5.20 Hz, 2H), 4.53-4.55 (complex, 1H), 6.81-6.89 (complex, 4H). A mixture of (4-methyl-3,4-dihydro-1,4-benzoxazin-2-yl)methyl methanesulfonate (3.7 g, 14.39 mmol), 4-hydroxy benzaldehyde (2.6 g, 21.29 mmol) and potassium carbonate (5.9 g, 42.7 mmol) in dry dimethyl formamide (30 mL) was stirred at 80° C. for 10 h. Water (100 mL) was added and extracted with ethyl acetate (2×70 mL). The combined organic layers were washed with water (50 mL), brine (50 mL) and dried ($Na_2SO_4$), filtered and the solvent was evaporated under reduced pressure. The residue was chromatographed over silica gel using a mixture of ethyl acetate and pet. ether (2:8) to afford the title compound (1.3 g, 32%) as a thick liquid.

$^1$H NMR (CDCl$_3$, 200 MHz): 2.93 (s, 3H), 3.24-3.46 (complex, 2H), 4.14-4.37 (complex, 2H), 4.68-4.71 (complex, 1H), 6.72-7.10 (complex, 6H), 7.86 (d, J=8.80 Hz, 2H), 9.92 (s, 1H).

Preparation 5

(±) 4-[4-Benzyl-3,4-dihydro-1,4-benzoxazin-2-yl]methoxybenzaldehyde

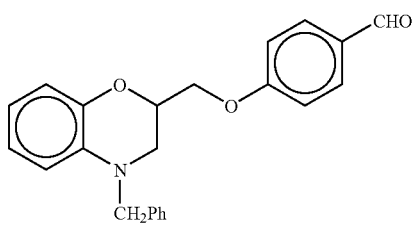

The title compound (3.2 g, 80%) was prepared as a pale yellow solid from 4-benzyl-3,4-dihydro-1,4-benzoxazin-2-methanol (4.0 g, 15.68 mmol) by a procedure similar to that described for preparation 4. mp: 92-94° C.

$^1$H NMR (CDCl$_3$, 200 MHz): δ 3.38-3.43 (complex, 2H), 4.14-4.32 (complex, 2H), 4.46 (d, J=7.80 Hz, 2H), 4.60-4.65 (complex, 1H), 6.65-6.89 (complex, 4H), 7.00 (d, J=8.80 Hz, 2H), 7.32 (s, 5H), 7.83 (d, J=8.80 Hz, 2H), 9.90 (s, 1H).

EXAMPLE 1

Ethyl (E/Z)-3-[4-[2-(2,3-dihydro-1,4-benzoxazin-4-yl)ethoxy]phenyl]-2-ethoxy propenoate

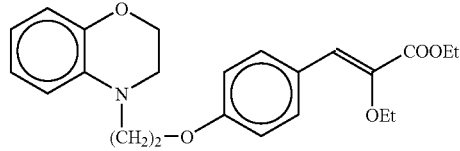

A solution of triethyl 2-ethoxyphosphonoacetate (W. Greli and H. Machleidt, *Annalen Chemie*, 1960, 699, 53). (7.8 g, 29.1 mmol) in dry tetrahydrofuran (15 mL) was added slowly to a stirred, ice-cooled suspension of sodium hydride (60% dispersion in oil) (1.39 g, 29.1 mmol) in dry tetrahydrofuran (5 mL) under nitrogen atmosphere. The mixture was stirred at 0° C. for 30 minutes followed by the addition of a solution of 4-[2-(2,3-dihydro-1,4-benzoxazin-4-yl)ethoxy]benzaldehyde (7.5 g, 26.5 mmol) which is prepared according to the process described in Preparation 1 disclosed in our International publication No. WO 98/52946, in dry tetrahydrofuran (20 mL). The mixture was allowed to warm to 25° C. and stirred further for 20 h. The solvent was evaporated and the residue was suspended in water (100 mL) and extracted with ethyl acetate (2×75 mL). The combined ethyl acetate layers were washed with water (75 mL), brine (50 mL), dried ($Na_2SO_4$), filtered and the solvent was evaporated under reduced pressure. The residue was chromatographed over silica gel using a mixture of ethyl acetate and petroleum ether (2:8) as eluent to afford the title compound (8.0 g, 75%) as a gum (65:35 Z:E mixture of geometric isomers) (R. A. Aitken and G. L. Thom, *Synthesis*, 1989, 958).

$^1$H NMR (CDCl$_3$, 200 MHz) δ: 1.18 and 1.36 (combined 6H, isomeric OEt, triplet signals), 3.51 (t, J=4.48 Hz, 2H), 3.71 (t, J=5.39 Hz, 2H), 3.89-4.03 (complex, 2H), 4.10-4.34 (complex, 6H), 6.07 (s, 0.35H, E olefinic proton), 6.63-7.14 (complex, 6.65H), 7.73 (d, J=8.72 Hz, 2H).

EXAMPLE 2

(±) Methyl 3-[4-[2-(2,3-dihydro-1,4-benzoxazin-4-yl)ethoxy]phenyl]-2-ethoxypropanoate

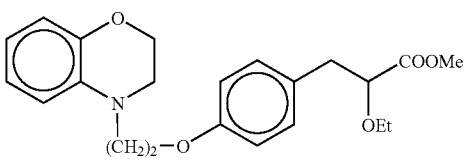

A mixture of ethyl (E/Z)-3-[4-[2-(2,3-dihydro-1,4-benzoxazin-4-yl)ethoxy]phenyl]-2-ethoxypropenoate (8.0 g, 20.0 mmol) obtained in example 1 and magnesium turnings (9.64 g, 396.7 mmol) in dry methanol (50 mL) was stirred at 25° C. for 20 h. At the end of this time, water (50 mL) was added and pH was adjusted to ca 7.0 using 10% aqueous hydrochloric acid and the solution was extracted with ethyl acetate (2×10 mL). The combined organic extracts were washed with water (75 mL), brine (75 mL), dried ($Na_2SO_4$), filtered and the solvent was removed under reduced pressure. The residue was chromatographed over silica gel using a mixture of ethyl acetate and pet. ether (2:8) as an eluent to afford the title compound (5.0 g, 64%) as a gummy liquid.

$^1$H NMR ($CDCl_3$, 200 MHz): δ 1.15 (t, J=7.00 Hz, 3H), 2.93 (d, J=6.64 Hz, 2H), 3.23-3.38 (complex, 1H), 3.43-3.72 (complex, 8H), 3.97 (t, J=6.90 Hz, 1H), 4.14 (t, J=5.81 Hz, 2H), 4.19 (t, J=4.20 Hz, 2H), 6.55-6.83 (complex, 6H), 7.13 (d, J=8.39 Hz, 2H).

EXAMPLE 3

Ethyl (E/Z)-3-[2-(2,3-dihydro-1,4-benzoxazin-4-yl) methylbenzofuran-5-yl]-2-ethoxy propenoate

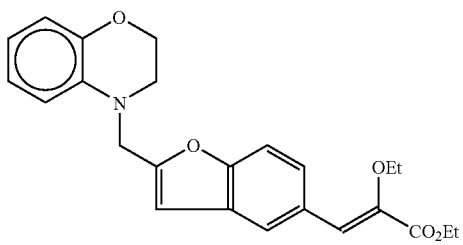

The title compound (0.8 g, 58%) was prepared as a gummy material from 5-formyl-2-(2,3-dihydro-1,4-benzoxazin-4-yl)methyl benzofuran (1.0 g, 3.41 mmol) by a procedure analogous to that described in example 1.

$^1$H NMR ($CDCl_3$, 200 MHz): δ 1.06 and 1.38 (6H, $OCH_2CH_3$ and $OCH_2CH_3$, triplet signals), 3.48 (t, J=4.98 Hz, 2H), 3.89-4.18 (complex, 2H), 4.28-4.40 (complex, 4H), 4.54 and 4.56 (combined, 2H, —$NCH_2$-signals), 6.20 (0.5H E isomer of olefinic proton), 6.52 and 6.59 (combined, 1H), 6.65-6.83 (complex, 2.5H), 7.08-7.11 (complex, 1H), 7.32-7.44 (complex, 2H), 7.69 (d, J=8.30 Hz, 1H), 7.99 (s, 1H).

EXAMPLE 4

Ethyl (E/Z-3-[4-[2-(2,3-dihydro-1,4-benzothiazin-4-yl)ethoxy]phenyl]-2-ethoxy propenoate

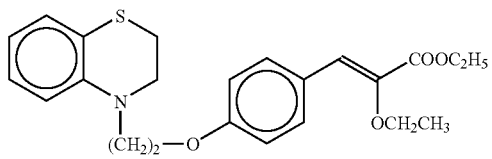

The title compound was prepared as a 38:62 ratio of geometric isomers (as measured by $^1$H NMR) (3.2 g, 71%) as a gummy material, from 4-[2-(2,3-dihydro-1,4 benzothiazin-4-yl)ethoxy]benzaldehyde (3.3 g, 11.03 mmol) prepared according to the process described in preparation 2 disclosed in our International publication No. WO 98/52946 by a method analogous to that described in example 1.

$^1$H NMR ($CDCl_3$, 200 MHz): δ 1.14 and 1.35 (combined, 6H, isomeric —$OCH_2CH_3$ triplet signals), 3.02 (t, J=4.90 Hz, 2H), 3.69-3.88 (complex, 4H), 3.92-4.03 (complex, 2H), 4.12-4.33 (complex, 4H), 6.06 (s, 0.38H, E olefinic proton), 6.61-7.14 (complex, 6.62H), 7.73 (d, J=8.81 Hz, 2H).

EXAMPLE 5

(±) Methyl 3-[2-(2,3-dihydro-1,4-benzoxazin-4-yl) methylbenzofuran-5-yl]-2-ethoxy propanoate

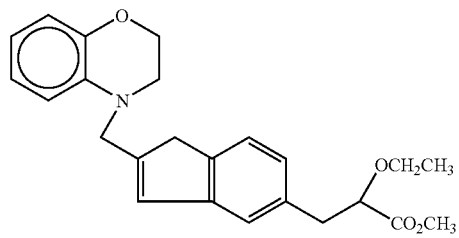

The title compound (0.6 g, 78%) was prepared as a gum from ethyl (E/Z)-3-[2-(2,3-dihydro-1,4-benzoxazin-4-yl) methylbenzofuran-5-yl]-2-ethoxypropenoate (0.8 g, 1.96 mmol) obtained in example 3 by a procedure analogous to that described for example 2.

$^1$H NMR ($CDCl_3$, 200 MHz): δ 1.5 (t, J=7.00 Hz, 3H), 3.07 (d, J=5.80 Hz 2H), 3.28-3.67 (complex, 4H), 3.70 (s, 3H), 4.03 (t, J=6.00 Hz, 1H), 4.28 (t, J=4.47 Hz, 2H), 4.54 (s, 2H), 6.52 (s, 1H), 6.62-6.89 (complex, 4H), 7.10 (d, J=7.05 Hz, 1H), 7.35 (complex, 2H).

EXAMPLE 6

(±) Methyl-3-[4-[2-(2,3-dihydro-1,4-benzothiazin-4-yl)ethoxy]phenyl]-2-ethoxy propanoate

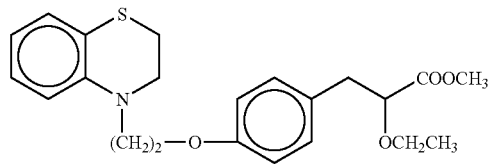

The title compound (2.3 g, 76%) was prepared as a gummy liquid from ethyl (E/Z)-3-[4-[2-(2,3-dihydro-1,4-benzothiazin-4-yl)ethoxy]phenyl]-2-ethoxypropenoate (3.1 g, 7.50 mmol) obtained in example 4 by an analogous procedure to that described in example 2.

$^1$H NMR ($CDCl_3$, 200 MHz): δ 1.15 (t, J=7.01 Hz, 3H), 2.93 (d, J=6.65 Hz, 2H), 3.03 (t, J=5.21 Hz, 2H), 3.23-3.41 (complex, 1H), 3.52-3.80 (complex, 8H), 3.97 (t, J=7.01 Hz, 1H), 4.14 (t, J=5.81 Hz, 2H), 6.61-6.82 (complex, 4H), 6.92-7.05 (complex, 2H), 7.13 (d, J=8.53 Hz, 2H).

EXAMPLE 7

(±) Methyl 2-methyl-3-[4-[2-(2,3-dihydro-1,4-benzoxazin-4-yl)ethoxy]phenyl]-2-ethoxypropanoate

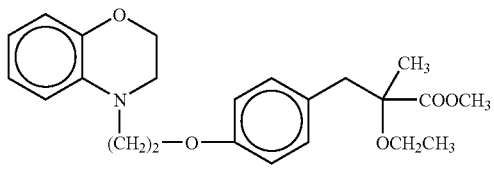

To a solution of (±) methyl 3-[4-[2-(2,3-dihydro-1,4-benzoxazin-4-yl)ethoxy]phenyl]-2-ethoxypropanoate (0.6 g, 1.5 mmol) obtained in example 2 in dry tetrahydrofuran (5 mL) was added lithium diisopropyl amide (5.25 μL, 0.5 mL solution in THF/hexane) at −78° C. After stirring for 1 h at −78° C., methyl iodide (0.75 mL) was added and the reaction mixture was allowed to warm to room temperature (ca 25° C.) and stirred for further 20 h at the same temperature. Water (20 mL) was added, acidified with 1 N hydrochloric acid and extracted with ethyl acetate (2×25 mL). The combined ethyl acetate layer was washed with water (25 mL), brine (25 mL), dried ($Na_2SO_4$), filtered and the solvent was evaporated under reduced pressure to afford the title compound (0.5 g, 80%) as an oil.

$^1$H NMR ($CDCl_3$, 200 MHz): δ1.21 (t, J=6.97 Hz, 3H), 1.31 (s, 3H), 2.95 (s, 2H), 3.32-3.58 (complex, 4H), 3.62-3.84 (complex, 5H), 4.14 (t, J=5.81 Hz, 2H), 4.22 (t, J=4.25 Hz, 2H), 6.55-6.88 (complex, 6H), 7.08 (d, J=8.63 Hz, 2H).

EXAMPLE 8

(±) Methyl 2-2-fluorobenzyl)-3-[4-[2-(2,3-dihydro-1,4-benzoxazin-4-yl)ethoxy]phenyl]-2-ethoxypropanoate

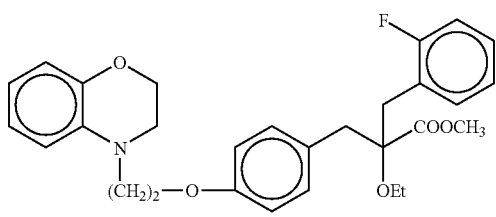

The title compound (0.6 g, 78%) was prepared as a brown liquid from (±) methyl 3-[4-[2-(2,3-dihydro-1,4-benzoxazin-4-yl)ethoxy]phenyl]-2-ethoxypropanoate (0.6 g, 1.5 mmol) obtained in example 2 by an analogous procedure to that described in example 7.

$^1$H NMR ($CDCl_3$, 200 MHz): δ 1.22 (t, J=6.96 Hz, 3H), 3.03-3.18 (complex, 4H), 3.51 (t, J=4.20 Hz, 2H), 3.59-3.71 (complex, 7H), 4.14 (t, J=5.81 Hz, 2H), 4.22 (t, J=4.24 Hz, 2H), 6.42-6.85 (complex, 6H), 6.90-7.32 (complex 6H).

EXAMPLE 9

Ethyl (E/Z)-3-[4-[2-(3-oxo-2H-1,4-benzoxazin-4-yl)ethoxy]phenyl]-2-ethoxy propenoate

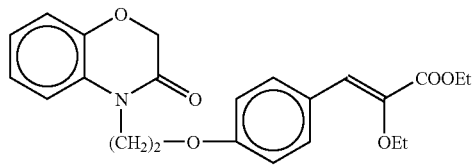

The title compound (3.9 g, 97%) was obtained in 32:68 ratio of E:Z isomers as a white solid from 4-[2-(3-oxo-2H-1,4-benzoxazin-4-yl)ethoxy]benzaldehyde (2.9 g, 9.7 mmol) obtained in preparation 1 by an analogous procedure to that described in example 1. mp: 92-95° C.

$^1$H NMR ($CDCl_3$, 200 MHz): δ 1.13-1.43 (complex, 6H), 3.88-4.02 (complex, 2H), 4.07-4.40 (complex, 6H), 4.60 (s, 2H), 6.05 (s, 0.32H, E olefinic proton), 6.76-7.32 (complex, 6.68H), 7.71 (d, J=8.72 Hz, 2H).

EXAMPLE 10

(±) Methyl 3-[4-[2-(3-oxo-2H-1,4-benzoxazin-4-yl) ethoxy]phenyl]-2-ethoxypropanoate

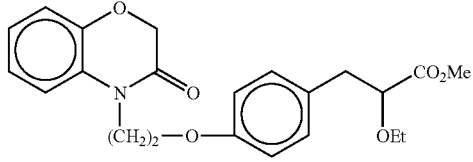

The title compound (1.0 g, 51%) was prepared as a colorless syrup from ethyl (E/Z)-3-[4-[2-(3-oxo-2H-1,4-benzoxazin-4-yl)ethoxy]phenyl]-2-ethoxypropenoate (2.0 g, 4.8 mmol) obtained in example 9 by a procedure analogous to that described in example 2.

$^1$H NMR ($CDCl_3$, 200 MHz): δ 1.14 (t, J=7.00 Hz, 3H), 2.92 (d, J=6.60 Hz, 2H), 3.25-3.41 (complex, 1H), 3.53-3.61 (complex, 1H), 3.68 (s, 3H), 3.96 (t, J=7.00 Hz, 1H), 4.21-4.32 (complex, 4H), 4.68 (s, 2H), 6.77 (d, J=8.63 Hz, 2H), 6.98-7.33 (complex, 6H).

EXAMPLE 11

Ethyl (E/Z)-3-[6-[2-(2,3-dihydro-1,4-benzothiazin-4-yl)ethoxyl]naphthyl]-2-ethoxy propenoate

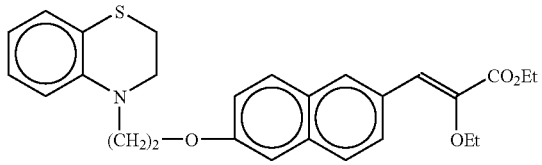

The title compound as a 1:1 mixture of E/Z isomers (1.74 g, 87%) was prepared as a brown syrup from 6-[2-(2,3-dihydro-1,4-benzothiazin-4-yl)ethoxy]naphthaldehyde (1.5 g, 4.29 mmol) obtained in preparation 3 by a procedure analogous to that described in example 1.

$^1$H NMR ($CDCl_3$, 200 MHz): δ 0.99-1.47 (complex, 6H), 3.06 (t, J=4.98 Hz, 2H), 3.79-3.95 (complex, 4H), 3.99-4.18 (complex, 2H), 4.25-4.37 (complex, 4H), 6.23 (s, 0.5H, E olefinic proton), 6.59-6.79 (complex, 2H), 6.97-7.29 (complex, 4.5H), 7.57-7.95 (complex, 3H), 8.14 (s, 1H).

EXAMPLE 12

(±) Methyl 3-[6-[2-(2,3-dihydro-1,4-benzothiazin-4-yl)ethoxy]naphthyl]-2-ethoxy propanoate

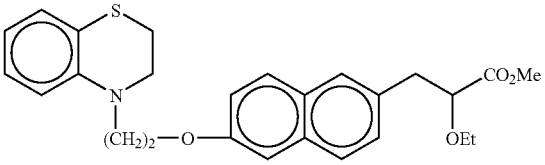

The title compound (1.25 g, 75%) was prepared as a colorless syrup from ethyl (E/Z)-3-[6-[2-(2,3-dihydro-1,4-benzothiazin-4-yl)ethoxy]naphthyl]-2-ethoxypropenoate (1.7 g, 3.67 mmol) obtained in example 11 by an analogous procedure to that described in example 2.

$^1$H NMR ($CDCl_3$, 200 MHz): δ 1.14 (t, J=7.06 Hz, 3H), 3.06 (t, J=5.21 Hz, 2H), 3.13 (d, J=7.15 Hz, 2H), 3.29-3.37

(complex, 1H), 3.57-3.64 (complex, 1H), 3.70 (s, 3H), 3.77-3.83 (complex, 4H), 4.09 (t, J=7.20 Hz, 1H), 4.25 (t, J=5.81 Hz, 2H), 6.62-6.79 (complex, 2H), 6.96-7.36 (complex, 5H), 7.60-7.70 (complex, 3H).

EXAMPLE 13

(±) Ethyl 3-[4-[2-(2,3-dihydro-1,4-benzoxazin-4-yl)ethoxy]phenyl]-2-hydroxypropanoate

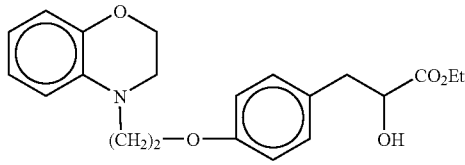

The title compound (0.14 g, 32%) was prepared as a gummy liquid from 2-(2,3-dihydro-1,4-benzoxazin-4-yl) ethyl methanesulfonate (0.36 g, 1.42 mmol), potassium carbonate (0.80 g, 5.8 mmol) and ethyl 2-hydroxy-3-(4-hydroxyphenyl)propanoate (0.3 g, 1.42 mmol) using conditions analogous to that described in preparation 2.

$^1$H NMR (CDCl$_3$, 200 MHz): δ 1.24 (t, J=7.15 Hz, 3H), 2.71 (d, J=6.23 Hz, 1H, D$_2$O exchangeable), 2.84-3.10 (complex, 2H), 3.50 (t, J=4.47 Hz, 2H), 3.67 (t, J=5.48 Hz, 2H), 4.11-4.26 (complex, 6H), 4.37-4.39 (complex, 1H), 6.61-6.86 (complex, 6H), 7.11 (d, J=8.62 Hz, 2H).

EXAMPLE 14

(±) Ethyl 3-[4-[2-2,3-dihydro-1,4-benzothiazin-4-yl)ethoxy]phenyl]-2-hydroxy propanoate

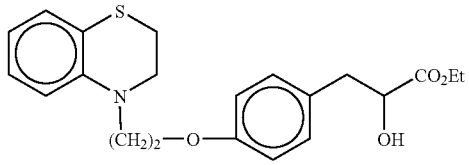

The title compound (1.9 g, 17%) was prepared as a gummy liquid from 2-(2,3-dihydro-1,4-benzothiazin-4-yl) ethyl methanesulfonate (8.2 g, 30.0 mmol), potassium carbonate (20.7 g, 150 mmol) and ethyl 2-hydroxy-3-(4-hydroxyphenyl)propanoate (6.3 μg, 30.0 mmol) using conditions analogous to that described in preparation 2.

$^1$H NMR (CDCl$_3$, 200 MHz): δ 1.29 (t, J=7.11 Hz, 3H), 2.70-2.80 (bs, 1H, D$_2$O exchangeable), 2.82-3.15 (complex, 4H), 3.65-3.82 (complex, 4H), 4.10-4.30 (complex, 4H), 4.28-4.40 (complex, 1H), 6.62-6.89 (complex, 4H), 6.92-7.18 (complex, 4H).

EXAMPLE 15

(±) Ethyl 3-[4-[2-(2,3-dihydro-1,4-benzoxazin-4-yl)ethoxy]phenyl]-2-benzyloxy propanoate

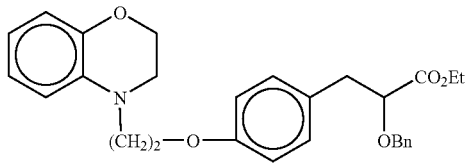

A solution of (±) ethyl 3-[4-[2-(2,3-dihydro-1,4-benzoxazin-4-yl)ethoxy]phenyl]-2-hydroxypropanoate (0.5 g, 1.34 mmol) obtained in example 13 in dry dimethyl formamide (5 mL) was added to a stirred ice cooled suspension of sodium hydride (60% dispersion in oil) (0.08 g, 1.66 mmol) in dry dimethyl formamide (3 mL) under nitrogen atmosphere. The reaction mixture was stirred at 0° C. for 30 minutes followed by the addition of benzyl bromide (0.46 g, 2.69 mmol). The mixture was allowed to warm to 25° C. and stirring was continued for further 18 h. Water (25 mL) was added and extracted with ethyl acetate (2×50 mL). The combined organic layer was washed with water (50 mL), brine (50 mL), dried (Na$_2$SO$_4$) and filtered. The solvent was evaporated under reduced pressure and the residue was chromatographed over silica gel using a mixture of ethyl acetate and pet. ether (2:8) as eluent to afford the title compound (0.3 g) along with benzyl 3-[4-[2-(2,3-dihydro-1,4-benzoxazin-4-yl)ethoxy]phenyl]-2-benzyloxypropanoate. This mixture (1:1) is used in example 47 without any separation.

$^1$H NMR (CDCl$_3$, 200 MHz): δ 1.23 (t, J=7.05 Hz, 1.55H), 2.99 (d, J=7.06 Hz, 4H), 3.00-3.72 (complex, 8H), 4.05-4.30 (complex, 12H), 4.32-4.71 (complex, 4H), 5.13 (s, 2H), 6.55-6.89 (complex, 12H), 7.05-7.36 (complex, 19H).

EXAMPLE 16

(±) Ethyl 3-[4-[2-(2,3-dihydro-1,4-benzoxazin-4-yl)ethoxy]phenyl]-2-butoxypropanoate

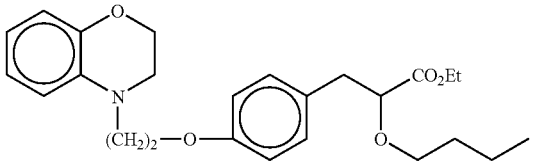

The title compound (0.4 g, 52%) was prepared as a gummy liquid from 2-(2,3-dihydro-1,4-benzoxazin-4-yl) ethyl methanesulfonate (0.46 g, 1.78 mmol), potassium carbonate (0.98 g, 7.12 mmol) and ethyl 2-butoxy-3-(4-hydroxyphenyl)propanoate (0.47 g, 1.78 mmol) using conditions analogous to that described in preparation 2.

$^1$H NMR (CDCl$_3$, 200 MHz): δ0.84 (t, J=7.53 Hz, 3H), 1.19-1.34 (complex, 5H), 1.43-1.55 (complex, 2H), 2.92 (d, J=6.32 Hz, 2H), 3.22-3.36 (complex, 1H), 3.48-3.59 (complex, 3H), 3.68 (t, J=5.82 Hz, 2H), 3.93 (t, J=6.20 Hz, 1H), 4.11-4.24 (complex, 6H), 6.61-6.86 (complex, 6H), 7.13 (d, J=8.30 Hz, 2H).

EXAMPLE 17

(±) Ethyl 3-[4-[2-2,3-dihydro-1,4-benzoxazin-4-yl)ethoxy]phenyl]-2-hexyloxy propanoate

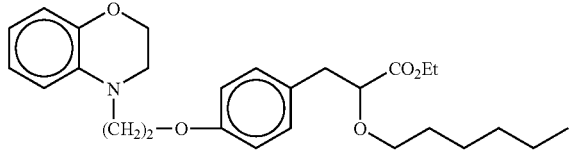

The title compound (0.31 g, 50%) was prepared as a colorless syrup from 2-(2,3-dihydro-1,4-benzoxazin-4-yl) ethyl methanesulfonate (0.35 g, 1.3 mmol), potassium carbonate (0.75 g, 5.4 mmol) and ethyl 2-hexyloxy-3-(4-hydroxyphenyl)propanoate (0.4 g, 1.3 mmol) using conditions analogous to that described in preparation 2.

$^1$H NMR (CDCl$_3$, 200 MHz): δ 0.85 (t, J=5.72 Hz, 3H), 1.20-1.34 (complex, 7H), 1.40-1.66 (complex, 4H); 2.93 (d, J=6.00 Hz, 2H), 3.21-3.31 (complex, 1H), 3.49-3.60 (complex, 3H), 3.68 (t, J=5.72 Hz, 2H), 3.93 (t, J=5.81 Hz, 1H), 4.11-4.24 (complex, 6H), 6.62-6.81 (complex, 5H), 7.09-7.16 (complex, 3H).

EXAMPLE 18

Ethyl (E/Z)-3-[4-[2-(2,3-dihydro-1,4-benzoxazin-4-yl)ethoxy]phenyl]-2-phenoxy propenoate

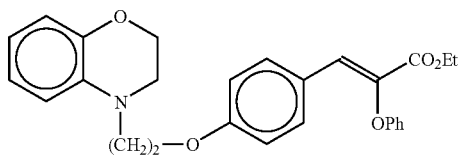

The title compound (0.92 g, 58%) was prepared as a mixture of E:Z isomers (40:60) as a syrupy liquid from 4-[2-(2,3-dihydro-1,4-benzoxazin-4-yl)ethoxy]benzaldehyde (1.0 g, 3.0 mmol) and triethyl 2-phenoxyphosphonoacetate (A. G. Schultz, et. al. J. Org. Chem., 1983, 48, 3408) (1.3 g, 4.0 mmol) by an analogous procedure to that described in example 1.

$^1$H NMR (CDCl$_3$, 200 MHz): δ 1.06 and 1.18 (combined 3H, isomeric OCH$_2$CH$_3$, triplet signals), 3.43-3.57 (complex, 2H), 3.64-3.75 (complex, 2H), 4.06-4.28 (complex, 6H), 6.60-6.90 (complex, 8H), 6.94-7.12 (complex, 2H), 7.22-7.45 (complex, 3H), 7.64 (d, J=8.72 Hz, 1H).

EXAMPLE 19

(±) Methyl 3-[4-[2-(2,3-dihydro-1,4-benzoxazin-4-yl)ethoxy]phenyl]-2-phenoxy propanoate

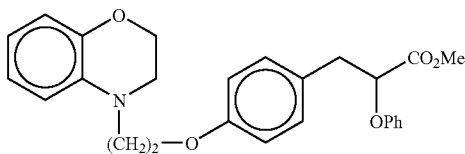

The title compound (0.49 g, 57%) was prepared as a gummy material from ethyl (E/Z)-3-[4-[2-(2,3-dihydro-1,4-benzoxazin-4-yl)ethoxy]phenyl]-2-phenoxypropenoate (0.9 g, 2.0 mmol) obtained in example 18 by an analogous procedure to that described for example 2.

$^1$HNMR (CDCl$_3$, 200 MHz): δ 3.17 (d, J=6.20 Hz, 2H), 3.50 (t, J=4.30 Hz, 2H), 3.65-3.70 (complex, 5H), 4.14 (t, J=5.76 Hz, 2H), 4.21 (t, J=4.15 Hz, 2H), 4.75 (t, J=6.40 Hz, 1H), 6.61-6.98 (complex, 9H), 7.17-7.27 (complex, 4H).

EXAMPLE 20

Ethyl (E/Z)-3-[4-[2-(2,3-dihydro-1,4-benzothiazin-4-yl)ethoxy]phenyl]-2-phenoxy propenoate

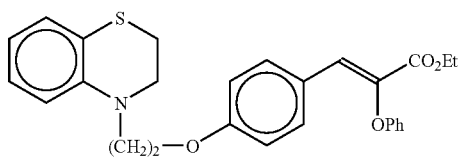

The title compound (3.7 g, 60%) was prepared as a mixture of E:Z isomers (35:65) as a gummy material from 4-[2-(2,3-dihydro-1,4-benzothiazin-4-yl)ethoxy]benzaldehyde (4.0 g, 13.0 mmol) and triethyl 2-phenoxyphosphonoacetate (A. G. Schultz, et. al. J. Org. Chem. 1983, 48, 3408), (5.07 g, 16.0 mmol) by an analogous procedure to that described in example 1.

$^1$H NMR (CDCl$_3$, 200 MHz): δ 1.05-1.36 (complex, 3H), 3.00-3.11 (complex, 2H), 3.64-3.85 (complex, 4H), 4.09-4.30 (complex, 4H), 6.58-7.13 (complex, 8H), 7.20-7.46 (complex, 4H), 7.65 (d, J=8.70 Hz, 2H).

EXAMPLE 21

(±) Methyl 3-[4-[2-(2,3-dihydro-1,4-benzothiazin-4-yl)ethoxy]phenyl]-2-phenoxy propanoate

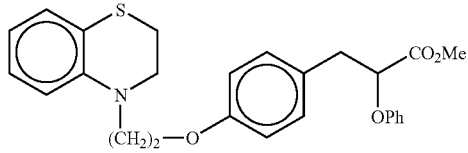

The title compound (2.3 g, 64%) was prepared as a gummy material from ethyl (E/Z-3-[4-[2-(2,3-dihydro-1,4-benzothiazin-4-yl)ethoxy]phenyl]-2-phenoxypropenoate (3.7 g, 8.0 mmol) obtained in example 20 by an analogous procedure to that described for example 2.

$^1$H NMR (CDCl$_3$, 200 MHz): δ 2.99 (t, J=5.43 Hz, 2H), 3.15 (d, J=5.99 Hz, 2H), 3.60-3.78 (complex, 7H), 4.13 (t, J=5.40 Hz, 2H), 4.74 (t, J=6.23 Hz, 1H), 6.58-6.89 (complex, 6H), 6.90-7.06 (complex, 2H), 7.11-7.30 (complex, 5H).

EXAMPLE 22

Ethyl (E/Z)-3-[4-(4-methyl-3,4-dihydro-1,4-benzoxazin-2-yl)methoxyphenyl]-2-ethoxy propenoate

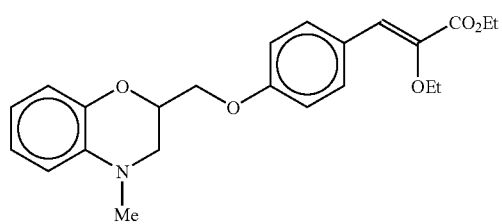

The title compound (0.4 g, 25%) was prepared as a mixture of E:Z isomers (1:1) as a brown liquid from 4-(4-methyl-3,4-dihydro-1,4-benzoxazin-2-yl)methoxybenzaldehyde (1.2 g, 4.24 mmol) obtained in preparation 4 by an analogous procedure to that described in example 1.

$^1$H NMR (CDCl$_3$, 200 MHz): δ 1.36 (t, J=7.10 Hz, 6H), 2.90 (s, 3H), 3.26-3.45 (complex, 2H), 3.99 (q, J=7.20 Hz, 2H), 4.10-4.38 (complex, 4H), 4.50-4.60 (complex, 1H), 6.70 (d, J=7.47 Hz, 2H), 6.81-6.90 (complex, 5H), 7.75 (d, J=8.80 Hz, 2H).

EXAMPLE 23

(±) Methyl 3-[4-(4-methyl-3,4-dihydro-1,4-benzoxazin-2-yl)methoxyphenyl]-2-ethoxypropanoate

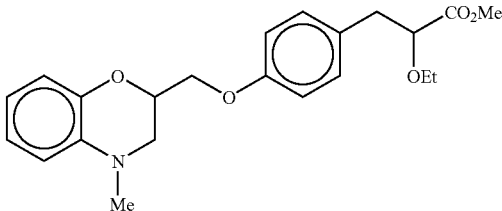

The title compound (0.25 g, 65%) was prepared as a thick liquid from ethyl (E/Z)-3-[4-(4-methyl-3,4-dihydro-1,4-benzoxazin-2-yl)methoxyphenyl]-2-ethoxypropenoate (0.4 g, 1.0 mmol) obtained in example 22 by an analogous procedure to that described in example 2.

$^1$H NMR (CDCl$_3$, 200 MHz): δ 1.16 (t, J=7.00 Hz, 3H), 2.89 (s, 3H), 2.95 (d, J=6.20 Hz, 2H), 3.19-3.41 (complex, 3H), 3.55-3.66 (complex, 1H), 3.70 (s, 3H), 3.95-4.24 (complex, 3H), 4.60-4.64 (complex, 1H), 6.64-7.08 (complex, 6H), 7.15 (d, J=8.40 Hz, 2H).

EXAMPLE 24

Ethyl (E/Z)-3-[4-(4-benzyl-3,4-dihydro-1,4-benzoxazin-2-yl)methoxyphenyl]-2-ethoxypropenoate

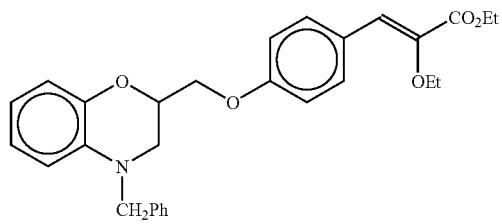

The title compound (3.0 g, 76%) was prepared as E:Z isomers (1:1), as a syrupy liquid from 4-[4-benzyl-3,4-dihydro-1,4-benzoxazin-2-yl)methoxybenzaldehyde (3.0 g, 8.35 mmol) obtained in preparation 5 by a procedure analogous to that described for example 1.

$^1$H NMR (CDCl$_3$, 200 MHz): δ 1.33-1.40 (complex, 6H), 3.39-3.44 (complex, 2H), 3.99 (q, J=7.00 Hz, 2H), 4.11-4.38 (complex, 4H), 4.46 (d, J=5.00 Hz, 2H), 4.52-4.66 (complex, 1H), 6.60-6.97 (complex, 7H), 7.28 (s, 5H), 7.75 (d, J=8.80 Hz, 2H).

EXAMPLE 25

(±) Methyl 3-[4(4-benzyl-3,4-dihydro-1,4-benzoxazin-2-yl)methoxyphenyl]-2-ethoxypropanoate

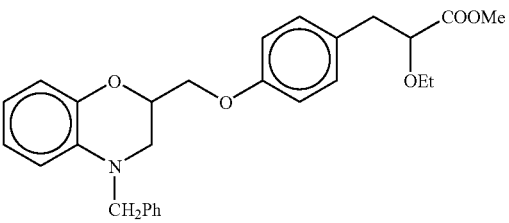

The title compound (1.5 g, 100%) was prepared from ethyl (E/Z)-3-[4-(4-benzyl-3,4-dihydro-1,4-benzoxazin-2-yl)methoxyphenyl]-2-ethoxypropenoate (1.5 g, 3.17 mmol) obtained in example 24 by an analogous procedure to that described in example 2.

$^1$H NMR (CDCl$_3$, 200 MHz): δ 1.17 (t, J=7.00 Hz, 3H), 2.96 (d, J=6.60 Hz 2H), 3.31-3.57 (complex, 3H), 3.60-3.70 (complex, 1H), 3.71 (s, 3H), 3.97-4.26 (complex, 3H), 4.47 (d, J=4.00 Hz, 2H), 4.56-4.61 (complex, 1H), 6.68-6.90 (complex, 6H), 7.15 (d, J=8.50 Hz, 2H), 7.29 (s, 5H).

EXAMPLE 26

(±) 3-[4-[2-(2,3-Dihydro-1,4-benzoxazin-4-yl)ethoxy]phenyl]-2-ethoxypropanoic acid

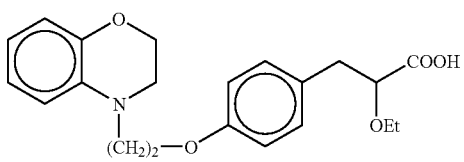

To a solution of (±) methyl 3-[4-[2-(2,3-dihydro-1,4-benzoxazin-4-yl)ethoxy]phenyl]-2-ethoxy propanoate (4.7 g, 12.2 mmol) obtained in example 2 in methanol (50 mL) was added aqueous 10% sodium hydroxide (28 mL). The mixture was stirred at 25° C. for 3 h. The solvent was removed under reduced pressure and the residue was acidified with 2N hydrochloric acid and extracted with ethyl acetate (2×100 mL). The combined ethyl acetate layers were washed with water (75 mL), brine (50 mL), dried (Na$_2$SO$_4$), filtered and the solvent was evaporated under reduced pressure. The residue was chromatographed over silica gel using ethyl acetate to afford the title compound (3.0 g, 66%) as a syrupy liquid.

$^1$H NMR (CDCl$_3$, 200 MHz): δ 1.17 (t, J=6.96 Hz, 3H), 2.85-3.12 (complex, 2H), 3.40-3.61 (complex, 4H), 3.69 (t, J=5.72 Hz, 2H), 4.04 (dd, J=7.38 and 4.27 Hz, 1H), 4.10-4.28 (complex, 4H), 6.52-6.85 (complex, 6H), 7.14 (d, J=8.60 Hz, 2H), COOH proton is too broad to observe.

EXAMPLE 27

(±) 3-[4-[2-Dihydro-1,4-benzoxazin-4-yl)ethoxy]phenyl]-2-ethoxypropanoic acid, sodium salt

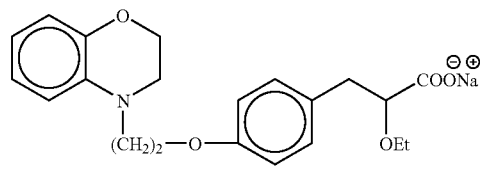

A mixture of (±) 3-[4-[2-(2,3-dihydro-1,4-benzoxazin-4-yl)ethoxy]phenyl]-2-ethoxypropanoic acid (0.15 g, 0.4 mmol) obtained in example 26 and sodium methoxide (23.4 mg) in methanol (5 mL) was stirred at 25° C. for 2 h. The solvent was removed and the residue was triturated with dry ether (3×10 mL). The precipitated solid was filtered, washed with dry ether (2×5 mL) and dried over P$_2$O$_5$ under vacuum to afford the title compound (0.12 g, 75%) as a colorless hygroscopic solid.

$^1$H NMR (DMSO-d$_6$, 200 MHz): δ 0.98 (t, J=6.83 Hz, 3H), 2.60-2.69 (complex, 1H), 2.78-2.92 (complex, 1H), 3.05-3.21 (complex, 2H), 3.41-3.75 (complex, 5H), 4.08-4.21 (complex, 4H), 6.49-6.85 (complex, 6H), 7.12 (d, J=8.30 Hz, 2H).

EXAMPLE 28

(±) 3-[2-(2,3-Dihydro-1,4-benzoxazin-4-yl)methyl-benzofuran-5-yl]-2-ethoxypropanoic acid

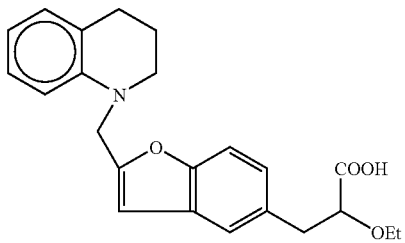

The title compound (0.5 g, 87%) was prepared as a gummy material from (±) methyl 3-[2-(2,3-dihydro-1,4-benzoxazin-4-yl)methylbenzofuran-5-yl]-2-ethoxypropanoate (0.6 g, 1.51 mmol) obtained in example 5 by a procedure analogous to that described for example 26.

$^1$H NMR (CDCl$_3$, 200 MHz): δ 1.26 (t, J=7.06 Hz, 3H), 3.05-3.28 (complex, 2H), 3.40-3.68 (complex, 4H), 4.09 (dd, J=7.47 and 4.24 Hz, 1H), 4.28 (t, J=4.15 Hz, 2H), 4.53 (s, 2H), 6.52 (s, 1H), 6.60-6.90 (complex, 4H), 7.13 (d, J=8.70 Hz, 1H), 7.32-7.36 (complex, 2H), COOH proton is too broad to observe.

EXAMPLE 29

(±) 3-[4-[2-(2,3-Dihydro-1,4-benzothiazin-4-yl)ethoxy]phenyl]-2-ethoxypropanoic acid

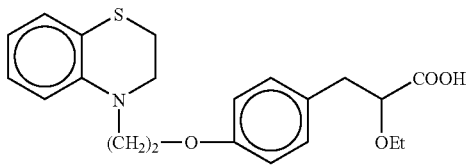

The title compound (1.4 g, 63%) was prepared as a gummy material from (±) methyl-3-[4-[2-(2,3-dihydro-1,4-benzothiazin-4-yl)ethoxy]phenyl]-2-ethoxypropanoate (2.3 g, 5.73 mmol) obtained in example 6 by a procedure analogous to that described for example 26.

$^1$H NMR (CDCl$_3$, 200 MHz): δ 1.18 (t, J=7.00 Hz, 3H), 2.82-3.15 (complex, 4H), 3.40-3.68 (complex, 2H), 3.70-3.81 (complex, 4H), 4.05 (dd, J=7.29 and 4.33 Hz 1H), 4.16 (t, J=5.72 Hz, 2H), 6.68-6.74 (complex, 2H), 6.81 (d, J=8.50 Hz, 2H), 6.94-7.06 (complex, 2H), 7.14 (d, J=8.50 Hz, 2H), COOH proton is too broad to observe.

EXAMPLE 30

(±) 3-[4-[2(2,3-Dihydro-1,4-benzothiazin-4-yl)ethoxy]phenyl]-2-ethoxypropanoic acid, sodium salt

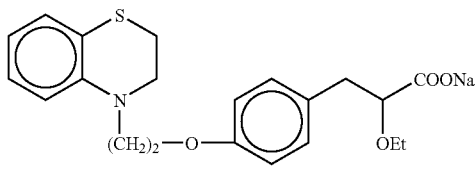

The title compound (0.42 g, 81%) was prepared as a colorless solid from (±) 3-[4-[2-2,3-dihydro-1,4-benzothiazin-4-yl)ethoxy]phenyl]-2-ethoxypropanoic acid (0.5 g, 1.30 mmol) obtained in example 29 by an analogous procedure to that described for example 27.

$^1$H NMR (CDCl$_3$, 200 MHz): δ 0.98 (t, J=7.00 Hz, 3H), 2.72-3.25 (complex, 5H), 3.30-3.51 (complex, 1H), 3.61-3.73 (complex, 4H), 3.82-3.91 (complex, 1H), 4.04 (t. J=5.72 Hz, 2H), 6.52-6.19 (complex, 4H), 6.91-7.03 (complex, 2H), 7.10 (d. J=8.40 Hz, 2H).

EXAMPLE 31

(±) 3-[4-[2-(2,3-Dihydro-1,4-benzothiazin-4-yl)ethoxy]phenyl]-2-ethoxypropanamide

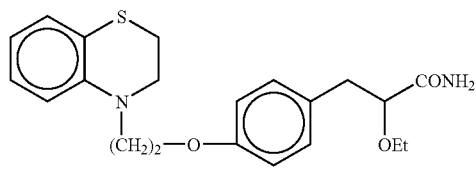

A solution of oxalyl chloride (0.28 mL, 3.1 mmol) and (±) 3-[4-[2-(2,3-dihydro-1,4-benzothiazin-4-yl)ethoxy]phenyl]-2-ethoxypropanoic acid (0.6 g, 1.55 mmol) obtained in example 29 in dry dichloromethane (10 mL) was refluxed for 2 h. The solvent and excess oxalyl chloride were removed under reduced pressure. The residue was dissolved in dichloromethane and stirred with aqueous ammonia (5 mL) for 30 min. The reaction mixture was extracted with chloroform (2×25 mL). The combined chloroform layers were washed with water (25 mL), dried (Na$_2$SO$_4$), filtered, and the solvent was evaporated under reduced pressure. The residue was chromatographed over silica gel using a mixture of ethyl acetate and pet. ether (7:3) as an eluent to afford the title compound (0.32 g, 54%) as a white solid. mp: 120-122° C.

$^1$H NMR (CDCl$_3$, 200 MHz): δ 1.15 (t, J=6.96 Hz, 3H), 2.81-3.20 (complex, 4H), 3.38-3.58 (complex, 2H), 3.71-3.90 (complex, 4H), 3.91 (dd, J=7.38 and 3.73 Hz, 1H), 4.16 (t, J=5.58 Hz, 2H), 5.54 (bs, D$_2$O exchangeable, 1H), 6.44 (bs, D$_2$O exchangeable, 1H), 6.59-6.84 (complex, 4H), 6.92-7.19 (complex, 4H).

EXAMPLE 32

(±) N-Methyl-3-[4-[2-2,3-dihydro-1,4-benzothiazin-4-yl)ethoxy]phenyl]-2-ethoxy propanamide

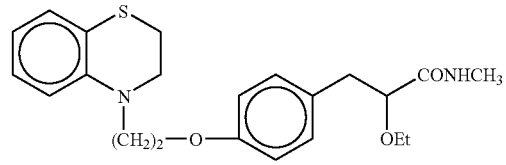

To an ice cooled solution of (±) 3-[4-[2-(2,3-dihydro-1,4-benzothiazin-4-yl)ethoxy]phenyl]-2-ethoxypropanoic acid (0.3 g, 0.78 mmol) obtained in example 29 and triethylamine (0.162 g, 1.6 mmol) in dry chloromethane (10 mL) was added pivaloyl chloride (0.10 g, 0.86 mmol) and stirred for 30 min at 0° C. To the above reaction mixture, methylamine (40% solution) (0.124 mL) was added at 25° C. and stirring was continued for 1 h at 25° C. Water (20 mL) was added and extracted with ethyl acetate (2×20 mL). The combined organic extracts were washed with water (10 mL), brine (10 mL), dried (Na$_2$SO$_4$), filtered and the solvent was evaporated under reduced pressure. The residue was chromatographed over silica gel using a mixture of ethyl acetate and pet. ether (1:1) to afford the title compound as a colorless solid. mp: 80-82° C.

$^1$H NMR (CDCl$_3$, 200 MHz): δ 1.11 (t, J=7.00 Hz, 3H), 2.76 (d, J=4.89 Hz, 3H), 2.81-2.88 (complex, 1H), 3.01-3.12 (complex, 3H), 3.39-3.52 (complex, 2H), 3.70-3.81 (complex, 4H), 3.86-3.91 (complex, 1H), 4.14 (t, J=5.81 Hz, 2H), 6.48 (bs, 1H), 6.61-6.81 (complex, 4H), 6.94-7.14 (complex, 4H).

EXAMPLE 33

(±) 3-[4-[2-2,3-Dihydro-1,4-benzoxazin-4-yl) ethoxy]phenyl]-2-ethoxypropanamide

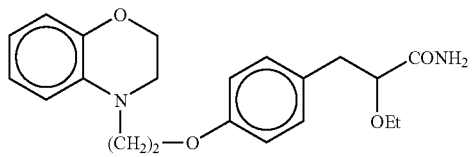

The title compound (0.2 g, 80%) was prepared as a white solid from (±) 3-[4-[2-(2,3-dihydro-1,4-benzoxazin-4-yl) ethoxy]phenyl]-2-ethoxypropanoic acid (0.25 g, 0.67 mmol) obtained in example 26 and aqueous ammonia (4 mL) by an analogous procedure to that described in example 31. mp: 107-109° C.

$^1$H NMR (CDCl$_3$, 200 MHz): δ 1.13 (t, J=6.96 Hz, 3H), 2.81-2.93 (complex, 1H), 3.03-3.19 (complex, 1H), 3.34-3.59 (complex, 4H), 3.69 (t, J=5.53 Hz, 2H), 3.88 (dd, J=7.43 and 3.70 Hz, 1H), 4.15 (t, J=5.58 Hz, 2H), 4.28 (t, J=4.24 Hz, 2H), 5.49 (bs, 1H, D$_2$O exchangeable), 6.43 (bs, 1H, D$_2$O exchangeable), 6.68-6.87 (complex, 6H), 7.15 (d, J=8.49 Hz, 2H).

EXAMPLE 34

(±) N-Methyl-3-[4-[2-(2,3-dihydro-1,4-benzoxazin-4-yl)ethoxy]phenyl]-2-ethoxy propanamide

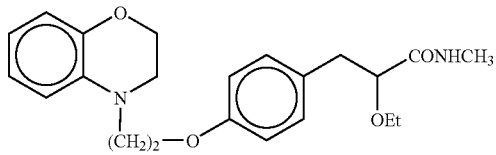

The title compound (0.23 g, 74%) was prepared as a white solid from (±) 3-[4-[2-(2,3-dihydro-1,4-benzoxazin-4-yl) ethoxy]phenyl]-2-ethoxypropanoic acid (0.3 g, 0.8 mmol) obtained in example 26 and methylamine (40% solution) (2 mL) by an analogous procedure to that described in example 32. mp: 97-99° C.

$^1$H NMR (CDCl$_3$, 200 MHz): δ 1.14 (t, J=7.00 Hz, 3H), 2.76 (d, J=4.98 Hz, 3H), 3.02-3.14 (complex, 1H), 3.35-3.45 (complex, 2H), 3.52 (t, J=4.57 Hz, 2H), 3.68 (t, J=5.81 Hz, 2H), 4.14 (t, J=5.72 Hz, 2H), 4.22 (t, J=4.15 Hz, 2H), 4.80-4.90 (complex, 1H), 6.50 (bs, 1H), 6.55-6.89 (complex, 6H), 7.11 (d, J=8.3 Hz, 2H), 7.88 (dd, J=7.06 and 3.74 Hz, 1H).

EXAMPLE 35

(±) N-Benzyl-3-[4-[2-(2,3-dihydro-1,4-benzoxazin-4-yl)ethoxy]phenyl]-2-ethoxy propanamide

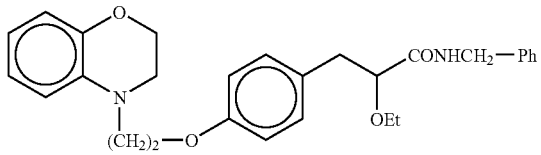

The title compound (0.25 g, 67%) was prepared as a white solid from (±) 3-[4-[2-(2,3-dihydro-1,4-benzoxazin-4-yl) ethoxy]phenyl]-2-ethoxypropanoic acid (0.3 g, 0.8 mmol) obtained in example 26 and benzyl amine (0.095 g, 0.88 mmol) by a procedure analogous to that described in example 32. mp: 94-96° C.

$^1$H NMR (CDCl$_3$, 200 MHz): δ 1.11 (t, J=7.00 Hz, 3H), 2.82-3.18 (complex, 2H), 3.40-3.55 (complex, 4H), 3.70 (t, J=5.49 Hz, 2H), 3.94-3.98 (complex, 1H), 4.14 (t, J=5.72 Hz, 2H), 4.23 (t, J=4.24 Hz, 2H), 4.28-4.52 (complex, 2H), 6.60-6.87 (complex, 6H), 7.06-7.32 (complex, 7H), CONH proton is too broad to observe.

EXAMPLE 36

(±) N-Benzyl-3-[4-[2-(2,3-dihydro-1,4-benzothiazin-4-yl)ethoxy]phenyl]-2-ethoxy propanamide

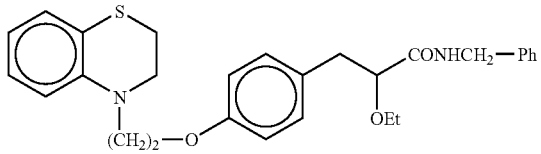

The title compound (0.22 g, 74%) was prepared as a white solid from (±) 3-[4-[2-(2,3-dihydro-1,4-benzothiazin-4-yl) ethoxy]phenyl]-2-ethoxypropanoic acid (0.25 g, 0.65 mmol) obtained in example 29 and benzylamine (0.076 g, 0.71 mmol) by an analogous procedure to that described in example 32. mp: 92-93° C.

$^1$H NMR (CDCl$_3$, 200 MHz): δ 1.15 (t, J=7.00 Hz, 3H), 2.88-3.20 (complex, 4H), 3.42-3.60 (complex, 2H), 3.73-3.87 (complex, 4H), 3.98-4.06 (complex, 1H), 4.18 (t, J=5.72 Hz, 2H), 4.30-4.56 (complex, 2H), 6.61-6.90 (complex, 4H), 7.00-7.43 (complex, 9H), CONH proton is too broad to observe.

EXAMPLE 37

(±) 2-Methyl-3-[4-[2-(2,3-dihydro-1,4-benzoxazin-4-yl)ethoxy]phenyl]-2-ethoxy propanoic acid

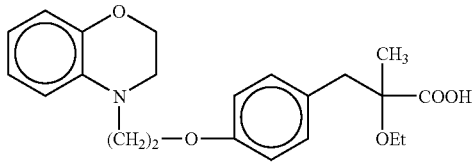

The title compound (0.3 g, 62%) was prepared as a gummy liquid from (±) methyl 2-methyl-3-[4-[2-(2,3-dihydro-1,4-benzoxazin-4-yl)ethoxy]phenyl]-2-ethoxypropanoate (0.5 g, 1.2 mmol) obtained in example 7 by an analogous procedure to that described in example 26.

$^1$H NMR (CDCl$_3$, 200 MHz): δ 1.24 (complex, 6H), 2.98, 3.04 (1H each, 2d. J=14.1 Hz each), 3.51 (t, J=4.25 Hz, 2H), 3.49-3.71 (complex, 4H), 4.15 (t, J=5.63 Hz, 2H), 4.22 (t, J=4.48 Hz, 2H), 6.60-6.87 (complex, 6H), 7.07 (d, J=8.67 Hz, 2H), COOH proton is too broad to observe.

EXAMPLE 38

(±) 2-Methyl-3-[4-[2-(2,3-dihydro-1,4-benzoxazin-4-yl)ethoxy]phenyl]-2-ethoxy propanoic acid, sodium salt

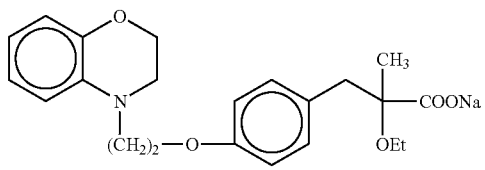

The title compound (0.12 g, 51%) was prepared as a white solid from (±) 2-methyl-3-[4-[2-(2,3-dihydro-1,4-benzoxazin-1-yl)ethoxy]phenyl]-2-ethoxypropanoic acid (0.22 g, 0.57 mmol) obtained in example 37 by an analogous procedure to that described in example 27.

$^1$H NMR (DMSO-d$_6$, 200 MHz): δ 0.96-1.08 (complex, 6H), 2.79 (s, 2H), 3.28-3.52 (complex, 4H), 3.64 (t, J=5.30 Hz, 2H), 4.05-4.19 (complex, 4H), 6.48-6.59 (complex, 1H), 6.62-6.86 (complex, 4H), 7.03-7.28 (complex, 3H).

EXAMPLE 39

(±) 2-(2-Fluorobenzyl)-3-[4-[2-(2,3-dihydro-1,4-benzoxazin-4-yl)ethoxy]phenyl]-2-ethoxypropanoic acid

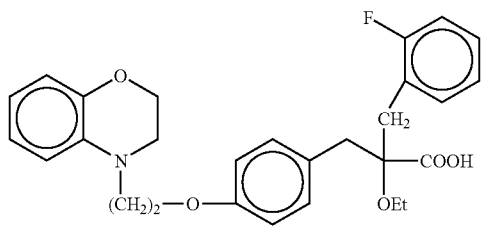

The title compound (0.25 g, 42%) was prepared as a gummy liquid from (±) methyl 2-(2-fluorobenzyl)-3-[4-[2-(2,3-dihydro-1,4-benzoxazin-4-yl)ethoxy]phenyl]-2-ethoxypropanoate (0.6 g, 1.2 mmol) obtained in example 8 by an analogous procedure to that described in example 26.

$^1$H NMR (CDCl$_3$, 200 MHz): δ 1.12 (t, J=6.82 Hz, 3H), 1.65 (bs, 1H, D$_2$O exchangeable), 3.11-3.42 (complex, 4H), 3.50 (t, J=4.34 Hz, 2H), 3.68 (t, J=5.67 Hz, 2H), 3.70-3.89 (complex, 2H), 4.14 (t, J=5.67 Hz, 2H), 4.21 (t, J=4.15 Hz, 2H), 6.62-6.86 (complex, 6H), 7.03-7.12 (complex, 4H), 7.18-7.30 (complex, 2H).

EXAMPLE 40

(±) 2-(2-Fluorobenzyl)-3-[4-[2-(2,3-dihydro-1,4-benzoxazin-4-yl)ethoxy]phenyl]-2-ethoxypropanoic acid, sodium salt

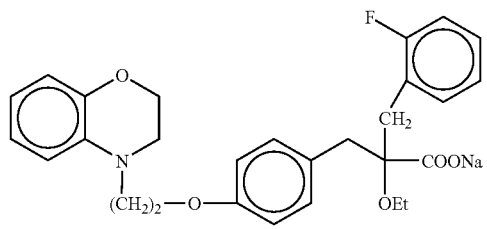

The title compound (0.11 g, 48%) was prepared as a white solid from (±) 2-(2-fluorobenzyl)-3-[4-[2-(2,3-dihydro-1,4-benzoxazin-4-yl)ethoxy]phenyl]-2-ethoxy propanoic acid (0.22 g, 0.45 mmol) obtained in example 39 by an analogous procedure to that described in example 27.

$^1$H NMR (CDCl$_3$, 200 MHz): δ 1.02 (t, J=6.65 Hz, 3H), 2.75-2.92 (complex, 4H), 3.39-3.58 (complex, 4H), 3.62 (bs, 2H), 4.04-4.20 (complex, 4H), 6.49-6.82 (complex, 5H), 6.90-7.28 (complex, 6H), 7.49-7.13 (complex, 1H).

EXAMPLE 41

(±) 3-[4-[2-(3-Oxo-2H-1,4-benzoxazin-4-yl)ethoxy]phenyl]-2-ethoxypropanoic acid

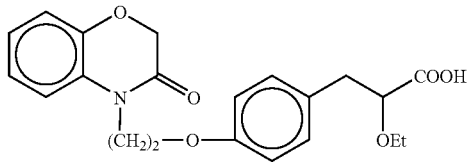

The title compound (0.75 g, 77%) was prepared as a white solid from (±) methyl 3-[4-[2-3-oxo-2H-1,4-benzoxazin-4-yl)ethoxy]phenyl]-2-ethoxypropanoate (1.0 g, 2.5 mmol) obtained in example 10 by a procedure analogous to that described in example 26. mp: 90-93° C.

$^1$H NMR (CDCl$_3$, 200 MHz): δ 1.18 (t, J=6.96 Hz, 3H), 2.88-3.13 (complex, 2H), 3.41-3.63 (complex, 2H), 4.06 (dd, J=7.43 and 4.33 Hz, 1H), 4.25-4.52 (complex, 4H), 4.61 (s, 2H), 6.80 (d, J=8.62 Hz, 2H), 7.00-7.34 (complex, 6H), COOH proton is too broad to observe.

EXAMPLE 42

(±) 3-[4-[2-(3-Oxo-2H-1,4-benzoxazin-4-yl)ethoxy]phenyl]-2-ethoxypropanoic acid, sodium salt

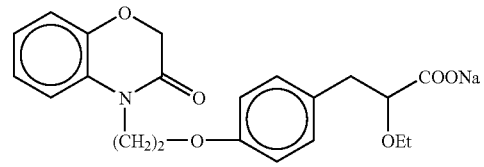

The title compound (0.12 g, 56%) was prepared as a white solid from (O) 3-[4-[2-(3-oxo-2H-1,4-benzoxazin-4-yl)ethoxy]phenyl]-2-ethoxypropanoic acid (0.2 g, 0.51 mmol) obtained in example 41 by an analogous procedure to that described in example 27.

$^1$H NMR (CDCl$_3$, 200 MHz): δ 0.99 (t, J=6.97 Hz, 3H), 2.61-2.80 (complex, 2H), 3.32-3.57 (complex, 1H), 3.60-3.72 (complex, 1H), 3.65-3.70 (complex, 1H), 4.18 (bs, 2H), 4.30 (bs, 2H), 4.68 (s, 2H), 6.78 (d, J=8.4 Hz, 2H), 7.03-7.14 (complex, 5H), 7.42 (d, J=7.06 Hz, 1H).

EXAMPLE 43

(±) 3-[6-[2-(2,3-Dihydro-1,4-benzothiazin-4-yl)ethoxy]naphthyl]-2-ethoxypropanoic acid

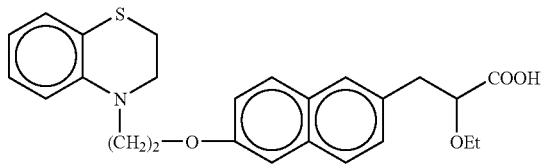

The title compound (0.8 g, 69%) was prepared as a white solid from (±) methyl 3-[6-[2-(2,3-dihydro-1,4-benzothiazin-4-yl)ethoxy]naphthyl]-2-ethoxypropanoate (1.2 g, 2.66 mmol) obtained in example 12 by an analogous procedure to that described in example 26. mp: 102-104° C.

$^1$H NMR (CDCl$_3$, 200 MHz): δ 1.15 (t, J=7.01 Hz, 3H), 3.06 (t, J=4.98 Hz, 2H), 3.08-3.63 (complex, 4H), 3.77-3.83 (complex, 4H), 4.15 (dd, J=4.15 and 4.18 Hz, 1H), 4.28 (t, J=5.95 Hz, 2H), 6.59-6.79 (complex, 2H), 6.96-7.36 (complex, 5H), 7.61-7.79 (complex, 3H), COOH proton is too broad to observe.

EXAMPLE 44

(±) 3-[6-[2-(2,3-Dihydro-1,4-benzothiazin-4-yl)ethoxy]naphthyl]-2-ethoxypropanoic acid, sodium salt

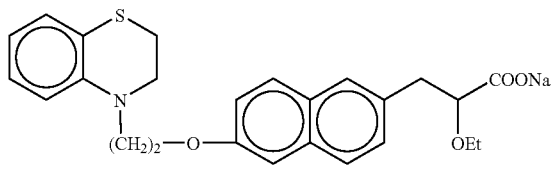

The title compound (0.16 g, 76%) was prepared as a white solid from (±) 3-[6-[2-(2,3-dihydro-1,4-benzothiazin-4-yl)ethoxy]naphthyl]-2-ethoxypropanoic acid (0.2 g, 0.457 mmol) obtained in example 43 by an analogous procedure to that described in example 27. mp: 138-140° C.

$^1$H NMR (DMSO-d$_6$, 200 MHz): δ 0.98 (t, J=7.06 Hz, 3H), 2.72-2.90 (complex, 1H), 2.92-3.21 (complex, 3H), 3.32-3.54 (complex, 2H), 3.61-3.91 (complex, 5H), 4.28 (bs, 2H), 6.56 (t, J=7.00 Hz, 1H), 6.73-7.00 (complex, 3H), 7.05-7.30 (complex, 2H), 7.38 (d, J=8.30 Hz, 1H), 7.60-7.82 (complex, 3H).

EXAMPLE 45

(±) 3-[4-[2-(2,3-Dihydro-1,4-benzoxazin-4-yl)ethoxy]phenyl]-2-hydroxypropanoic acid

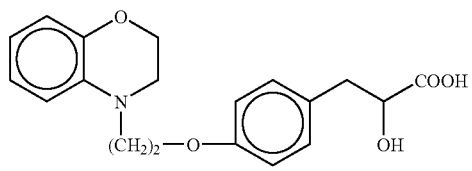

The title compound (0.06 g, 43%) was prepared as a brown syrupy liquid from (±) ethyl 3-[4-[2-(2,3-dihydro-1,4-benzoxazin-4-yl)ethoxy]phenyl]-2-hydroxypropanoate (0.15 g, 0.40 mmol) obtained in example 13 by an analogous procedure to that described in example 26.

$^1$H NMR (CDCl$_3$, 200 MHz): δ2.85-3.19 (complex, 2H), 3.43 (t, J=4.15 Hz, 2H), 3.61 (t, J=5.49 Hz, 2H), 4.07 (t, J=5.40 Hz, 2H), 4.16 (t, J=4.48 Hz, 2H), 4.45 (bs, 1H), 6.50-6.82 (complex, 6H), 7.08 (d, J=7.88 Hz, 2H), COOH and OH protons are too broad to observe.

EXAMPLE 46

(±) 3-[4-[2-(2,3-Dihydro-1,4-benzothiazin-4-yl)ethoxy]phenyl]-2-hydroxypropanoic acid

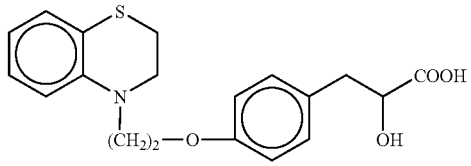

The title compound (0.7 g, 46%) was prepared as a white solid from (±) ethyl 3-[4-[2-(2,3-dihydro-1,4-benzothiazin-4-yl)ethoxy]phenyl]-2-hydroxypropanoate (1.7 g, 4.39 mmol) obtained in example 14 by a procedure analogous to that described in example 26. mp: 74-76° C.

$^1$H NMR (CDCl$_3$, 200 z): δ 2.88-3.18 (complex, 4H), 3.69-3.79 (complex, 4H), 4.15 (t, J=5.72 Hz, 2H), 4.45 (dd, J=6.73 and 4.79 Hz, 1H), 4.51-4.97 (bs, D$_2$O exchangeable, 1H), 6.65-6.89 (complex, 4H), 6.94-7.17 (complex, 4H), COOH proton is too broad to observe.

EXAMPLE 47

(±) 3-[4-[2-(2,3-Dihydro-1,4-benzoxazin-4-yl)ethoxy]phenyl]-2-benzyloxypropanoic acid

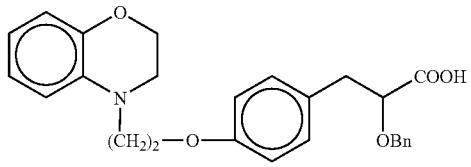

The title compound (0.15 g, 67%) was prepared as a thick liquid from (±) ethyl 3-[4-[2-(2,3-dihydro-1,4-benzoxazin-4-yl)ethoxy]phenyl]-2-benzyloxypropanoate (0.24 g, 0.52 mmol) obtained in example 15 by a procedure analogous to that described in example 26.

$^1$H NMR (CDCl$_3$, 200 MHz): δ 1.40-2.80 (br, 1H, D$_2$O exchangeable), 2.99-3.18 (complex, 2H), 3.51 (t, J=4.34 Hz, 2H), 3.70 (t, J=5.82 Hz, 2H), 4.13-4.24 (complex, 5H), 4.51 (d, J=17.0 Hz, 2H), 6.60-6.89 (complex, 6H), 7.10-7.37 (complex, 7H).

EXAMPLE 48

(±) 3-[4-[2-(2,3-Dihydro-1,4-benzoxazin-4-yl)ethoxy]phenyl]-2-benzyloxypropanoic acid, sodium salt

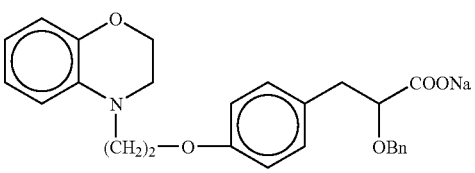

The title compound (0.1 g, 73%) was prepared as a cream colored hygroscopic solid from (±) 3-[4-[2-(2,3-dihydro-1,4-benzoxazin-4-yl)ethoxy]phenyl]-2-benzyloxy propanoic acid (0.13 g, 0.30 mmol) obtained in example 47 by a procedure analogous to that described in example 27.

¹H NMR (DMSO-d₆, 200 MHz): δ 2.62-2.74 (complex, 1H), 2.89-2.98 (complex, 1H), 3.48 (t, J=4.20 Hz, 2H), 3.67 (t, J=5.48 Hz, 2H), 4.12-4.26 (complex, 5H), 4.65 (d, J=12.45 Hz, 2H), 6.45-6.84 (complex, 6H), 7.12-7.25 (complex, 7H).

EXAMPLE 49

(±) 3-[4-[2-(2,3-Dihydro-1,4-benzoxazin-4-yl)ethoxy]phenyl]-2-butoxypropanoic acid

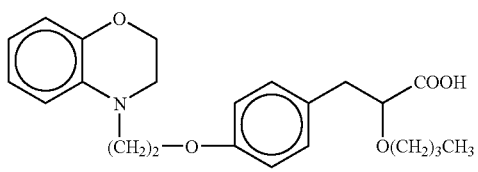

The title compound (0.25 g, 67%) was prepared as a syrupy liquid from (±) ethyl 3-[4-[2-(2,3-dihydro-1,4-benzoxazin-4-yl)ethoxy]phenyl]-2-butoxypropanoate (0.4 g, 0.93 mmol), obtained in example 16 by an analogous procedure to that described in example 26.

¹H NMR (CDCl₃, 200 MHz): δ 0.87 (t, J=7.15 Hz, 3H), 1.25-1.40 (complex, 2H), 1.49-1.66 (complex, 2H), 2.95-3.15 (complex, 2H), 3.43-3.53 (complex, 4H), δ 3.68 (t, J=5.49 Hz, 2H), 4.00-4.12 (complex, 1H), 4.14 (t, J=5.65 Hz, 2H), 4.22 (t, J=4.25 Hz, 2H), 6.60-6.89 (complex, 6H), 7.12 (d, J=8.39 Hz, 2H), COOH proton is too broad to observe.

EXAMPLE 50

(±) 3-[4-[2-(2,3-Dihydro-1,4-benzoxazin-4-yl)ethoxy]phenyl]-2-butoxypropanoic acid, sodium salt

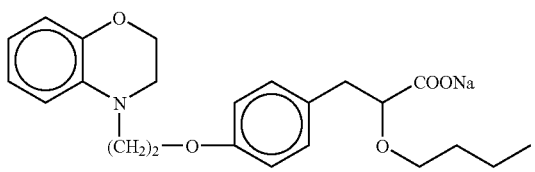

The title compound (0.12 g, 57%) was prepared as a hygroscopic cream color solid from (±) 3-[4-[2-(2,3-dihydro-1,4-benzoxazin-4-yl)ethoxy]phenyl]-2-butoxypropanoic acid (0.2 g, 0.5 mmol) obtained in example 49 by an analogous procedure to that described in example 27.

¹H N (DMSO-d₆, 200 MHz): δ 0.78 (t, J=7.06 Hz, 3H), 1.16-1.56 (complex, 4H), 2.52-2.64 (complex, 1H), 2.79-2.87 (complex, 1H), 2.99-3.18 (complex, 2H), 3.40 (bs, 2H), 3.66 (t, J=5.31 Hz, 2H), 4.10-4.25 (complex, 5H), 6.52-6.90 (complex, 6H), 7.12 (d, J=8.30 Hz, 2H).

EXAMPLE 51

(±) 3-[4-[2-(2,3-Dihydro-1,4-benzoxazin-4-yl)ethoxy]phenyl]-2-hexyloxypropanoic acid

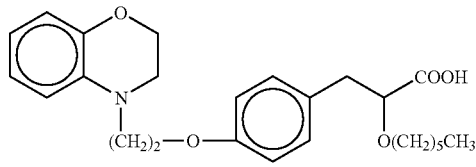

The title compound (0.17 g, 60%) was prepared as a greenish liquid from (±) ethyl 3-[4-[2-(2,3-dihydro-1,4-benzoxazin-4-yl)ethoxy]phenyl]-2-hexyloxypropanoate (0.3 g, 0.65 mmol) obtained in example 17 by a procedure analogous to that described in example 26.

¹HMR (CDCl₃, 200 MHz): δ 0.86 (t, J=5.72 Hz, 3H), 1.25-1.33 (complex, 4H), 1.41-1.75 (complex, 4H), 2.94-3.06 (complex, 2H), 3.36-3.58 (complex, 4H), 3.68 (t, J=5.49 Hz, 2H), 4.01-4.06 (complex, 1H), 4.14 (t, J=5.70 Hz, 2H), 4.22 (t, J=4.15 Hz, 2H), 6.71-7.08 (complex, 6H), 7.12 (d, J=8.40 Hz, 2H), COOH proton is too broad to observe.

EXAMPLE 52

(±) 3-[4-[2-(2,3-Dihydro-1,4-benzoxazin-4-yl)ethoxy]phenyl]-2-hexyloxypropanoic acid, sodium salt

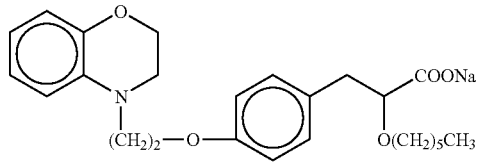

The title compound (0.1 g, 52%) was prepared as a white hygroscopic solid from (±) 3-[4-[2-(2,3-dihydro-1,4-benzoxazin-4-yl)ethoxy]phenyl]-2-hexyloxypropanoic acid (0.18 g, 0.42 mmol) obtained in example 51 by an analogous procedure to that described in example 27.

¹H NMR (DMSO-d₆, 200 MHz): δ 0.82 (t, J=5.72 Hz, 3H), 1.10-1.45 (complex, 8H), 2.75-2.96 (complex, 2H), 3.35-3.56 (complex, 4H), 3.67 (t, J=5.30 Hz, 2H), 4.08-4.21 (complex, 5H), 6.50-6.82 (complex, 6H), 7.12 (d, J=8.00 Hz, 2H).

EXAMPLE 53

(±) 3-[4-[2-(2,3-Dihydro-1,4-benzoxazin-4-yl)ethoxy]phenyl]-2-phenoxypropanoic acid

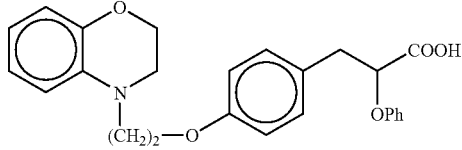

The title compound (0.1 g, 53%) was prepared as a colorless liquid from (±) methyl 3-[4-[2-(2,3-dihydro-1,4-benzoxazin-4-yl)ethoxy]phenyl]-2-phenoxypropanoate (0.2 g, 0.461 mmol) obtained in example 19 by an analogous procedure to that described in example 26.

¹H NMR (CDCl₃, 200 MHz): δ 2.40-2.80 (bs, 1H, D₂O exchangeable), 3.22 (d, J=5.80 Hz, 2H), 3.49 (t, J=4.25 Hz, 2H), 3.67 (t, J=5.81 Hz, 2H), 4.14 (t, J=5.81 Hz, 2H), 4.21 (t, J=4.16 Hz, 2H), 4.82 (t, J=590 Hz, 1H), 6.61-7.02 (complex, 8H), 7.17-7.30 (complex, 5H).

EXAMPLE 54

(±) 3-[4-[2-(2,3-Dihydro-1,4-benzothiazin-4-yl)ethoxy]phenyl]-2-phenoxypropanoic acid

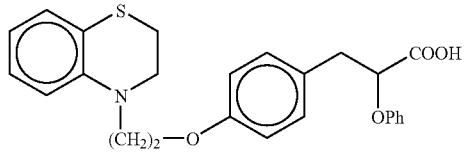

The title compound (0.2 g, 51%) was prepared as a gummy solid from (±) methyl 3-[4-[2-(2,3-dihydro-1,4-benzothiazin-4-yl)ethoxy]phenyl]-2-phenoxypropanoate (0.4 g, 0.9 mmol) obtained in example 21 by a procedure analogous to that described in example 26.

¹H NMR (CDCl₃, 200 MHz): δ 3.02 (t, J=5.00 Hz, 2H), 3.22 (d, J=6.25 Hz, 2H), 3.68-3.78 (complex, 4H), 4.14 (t, J=5.81 Hz, 2H), 4.50 (t, J=6.19 Hz, 1H), 4.90-5.40 (b, 1H, D₂O exchangeable), 6.58-6.86 (complex, 7H), 6.94-7.07 (complex, 2H), 7.18-7.29 (complex, 4H).

EXAMPLE 55

(±) 3-[4-[2-2,3-Dihydro-1,4-benzoxazin-4-yl)ethoxy]phenyl]-2-phenoxypropanoic acid, sodium salt

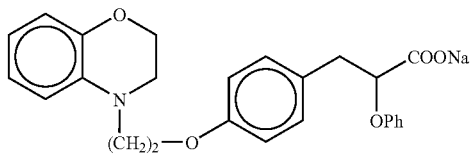

The title compound (0.05 g, 48%) was prepared as a hygroscopic solid from (±) 3-[4-[2-(2,3-dihydro-1,4-benzoxazin-4-yl)ethoxy]phenyl]-2-phenoxypropanoic acid 0.1 g, 0.24 mmol) obtained in example 53 by a procedure analogous to that described in example 27.

¹H NMR (DMSO-d₆, 200 MHz) δ 2.81-3.09 (complex, 2H), 3.42 (bs, 2H), 3.65 (t, J=4.5 Hz, 2H), 4.12 (bs, 4H), 4.22-4.32 (complex, 1H), 6.50-6.92 (complex, 8H), 7.10-7.33 (complex, 5H).

EXAMPLE 56

(±) Methyl 2-methyl-3-[4-[2-(2,3-dihydro-1,4-benzoxazin-4-yl)ethoxy]phenyl]-2-phenoxypropanoate

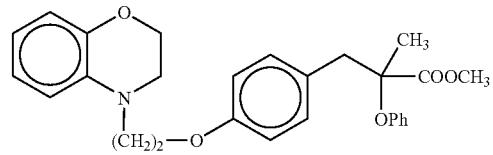

The title compound (0.27 g, 87%) was prepared as a syrupy liquid from (±) methyl 3-[4-[2-(2,3-dihydro-1,4-benzoxazin-4-yl)ethoxy]phenyl]-2-phenoxypropanoate (0.3 g, 0.69 mmol) obtained in example 19 by an analogous procedure to that described in example 7.

¹H NMR (CDCl₃, 200 MHz): δ 1.39 (s, 3H), 3.09, 3.26 (1H each, 2d, J=13.7 Hz each), 3.51 (t, J=4.30 Hz, 2H), 3.66-3.73 (complex, 5H), 4.15 (t, J=5.50 Hz, 2H), 4.22 (t, J=4.24 Hz, 2H), 6.61-7.01 (complex, 9H), 7.12-7.22 (complex, 4H).

EXAMPLE 57

(±) 2-Methyl-3-[4-[2-(2,3-dihydro-1,4-benzoxazin-4-yl)ethoxy]phenyl]-2-phenoxy propanoic acid

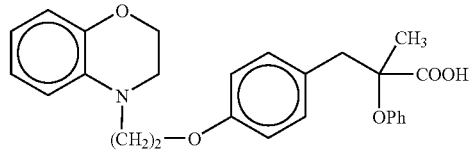

The title compound (0.13 g, 50%) was prepared as a pale yellow hygroscopic solid from (±) methyl 2-methyl-3-[4-[2-2,3-dihydro-1,4-benzoxazin-4-yl)ethoxy]phenyl]-2-phenoxypropanoate (0.27 g, 0.60 mmol) obtained in example 56 by a procedure analogous to that described in example 26.

¹H NMR (CDCl₃, 200 MHz): δ 1.42 (s, 3H), 3.12, 3.29 (1H each, 2d, J=14.1 Hz each), 3.50 (t, J=4.50 Hz, 2H), 3.69 (t, J=5.60 Hz, 2H), 4.16 (t, J=5.81 Hz, 2H), 4.22 (t, J=4.50 Hz, 2H), 6.62-7.17 (complex, 9H), 7.21-7.30 (complex, 4H), COOH proton is too broad to observe.

EXAMPLE 58

(±) 2-Methyl-3-[4-[2-(2,3-dihydro-1,4-benzoxazin-4-yl)ethoxy]phenyl]-2-phenoxy propanoic acid, sodium salt

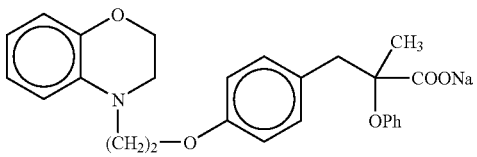

The title compound (0.055 g, 46%) was prepared as a hygroscopic pale yellow powder from (±) 2-methyl-3-[4-[2-(2,3-dihydro-1,4-benzoxazin-4-yl)ethoxy]phenyl]-2-phenoxypropanoic acid (0.13 g, 0.28 mmol) obtained in example 57 by a procedure analogous to that described in example 27.

¹H NMR (CDCl₃, 200 MHz): δ 1.15 (s, 3H), 2.99-3.21 (complex, 2H), 3.47 (bs, 2H), 3.67 (bs, 2H), 4.14 (bs, 4H), 6.53-6.90 (complex, 9H), 7.08-7.30 (complex, 4H).

EXAMPLE 59

(±) Methyl 2-methyl-3-[4-[2-(2,3-dihydro-1,4-benzothiazin-4-yl)ethoxy]phenyl]-2-phenoxypropanoate

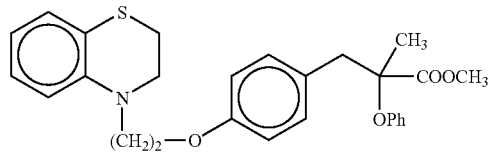

The title compound (0.96 g, 93%) was prepared as a pale yellow liquid from (±) methyl 3-[4-[2-(2,3-dihydro-1,4-benzothiazin-4-yl)ethoxy]phenyl]-2-phenoxypropanoate (1.0 g, 2.22 mmol) obtained in example 21 by an analogous procedure to that described in example 7.

¹H NMR (CDCl₃, 200 MHz): δ 1.40 (s, 3H), 3.03 (t, J=4.90 Hz, 2H), 3.09, 3.27 (1H each, 2d, J=13.7 Hz each), 3.70-3.85 (complex, 7H), 4.16 (t, J=5.8.1 Hz, 2H), 6.60-6.89 (complex, 6H), 6.96-7.30 (complex, 7H).

EXAMPLE 60

(±) 2-Methyl-3-[4-[2-(2,3-dihydro-1,4-benzothiazin-4-yl)ethoxy]phenyl]-2-phenoxy propanoic acid

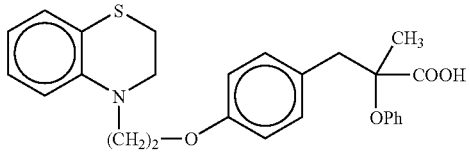

The title compound (0.6 g, 65%) was prepared as a syrupy liquid from (±) methyl 2-methyl-3-[4-[2-(2,3-dihydro-1,4-benzothiazin-4-yl)ethoxy]phenyl]-2-phenoxypropanoate (0.96 g, 2.00 mmol) obtained in example 59 by an analogous procedure to that described in example 26.

¹H NMR (CDCl₃, 200 MHz): δ 1.42 (s, 3H), 3.03 (t, J=5.00 Hz, 2H), 3.12, 3.30 (1H each, 2d, J=13.8 Hz each), 3.70-3.80 (complex, 4H), 4.15 (t, J=5.50 Hz, 2H), 6.58-7.08 (complex, 8H), 7.18-7.30 (complex, 5H), COOH proton is too broad to observe.

EXAMPLE 61

(±) 4-Nitrophenyl 3-[4-[2-(2,3-dihydro-1,4-benzothiazin-4-yl)ethoxy]phenyl]-2-ethoxypropanoate

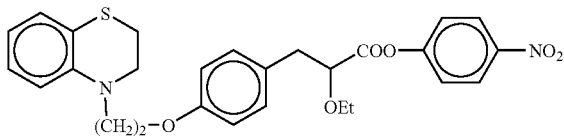

The title compound (0.15 g, 38%) was prepared as a yellow liquid from (±) 3-[4-[2-2,3-dihydro-1,4-benzothiazin-4-yl)ethoxy]phenyl]-2-ethoxypropanoic acid (0.3 g, 0.77 mmol) obtained in example 29 and 4-nitrophenol by an analogous procedure to that described in example 32.

¹H NMR (CDCl₃, 200 MHz): δ 1.24 (t, J=6.92 Hz, 3H), 3.04 (t, J=5.16 Hz, 2H), 3.12 (d, J=6.63 Hz, 2H), 3.46-3.65 (complex, 1H), 3.70-3.86 (complex, 5H), 4.16 (t, J=5.23 Hz, 2H), 4.26 (t, J=5.50 Hz, 1H), 6.62-6.74 (complex, 2H), 6.84 (d, J=8.62 Hz, 2H), 6.94-7.22 (complex, 6H), 8.23 (d, J=9.00 Hz, 2H).

EXAMPLE 62

(±) 3-[4-(4-Benzyl-3,4-dihydro-1,4-benzoxazin-2-yl)methoxyphenyl]-2-ethoxy propanoic acid

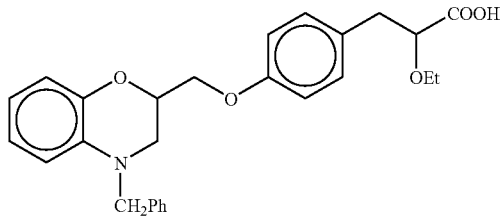

The title compound (0.4 g, 57%) was prepared as a syrupy liquid from (±) methyl 3-[4-(4-benzyl-3,4-dihydro-1,4-benzoxazin-2-yl)methoxyphenyl]-2-ethoxypropanoate (0.8 g, 2.16 mmol) obtained in example 25 by an analogous procedure to that described in example 26.

¹H NMR (CDCl₃, 200 MHz): δ 1.17 (t, J=7.00 Hz, 3H), 2.99-3.13 (complex, 2H), 3.31-3.65 (complex, 4H), 4.01-4.24 (complex, 3H), 4.45 (d, J=3.40 Hz, 2H), 4.52-4.59 (complex, 1H), 6.62-6.68 (complex, 6H), 7.14 (d, J=8.60 Hz, 2H), 7.27 (s, 5H), COOH proton is too broad to observe.

EXAMPLE 63

(±) 3-[4-(4-Benzyl-3,4-dihydro-1,4-benzoxazin-2-yl) methoxyphenyl]-2-ethoxy propanoic acid, sodium salt

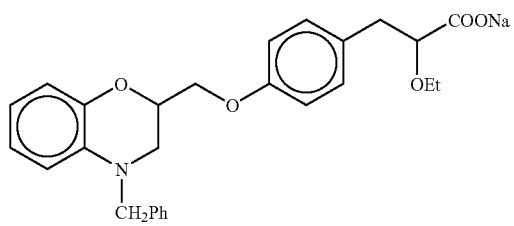

The title compound (0.15 g, 75%) was prepared as a colorless hygroscopic solid from (±) 3-[4(4-benzyl-3,4-dihydro-1,4-benzoxazin-2-yl)methoxyphenyl]-2-ethoxy propanoic acid (0.2 g, 0.44 mmol) obtained in example 62 by an analogous procedure to that described in example 27.

¹H NMR (DMSO-d₆, 200 MHz): δ 0.99 (t, J=6.97 Hz, 3H), 2.60-2.90 (complex, 2H), 3.30-3.65 (complex, 5H), 4.16 (d, J=5.00 Hz, 2H), 4.40-4.65 (complex, 3H), 6.55-6.89 (complex, 6H), 7.14 (d, J=8.50 Hz, 2H), 7.32 (s, 5H).

EXAMPLE 64

(±) 4-Nitrophenyl 3-[4-(4-benzyl-3,4-dihydro-1,4-benzoxazin-2-yl)methoxy phenyl]-2-ethoxypropanoate

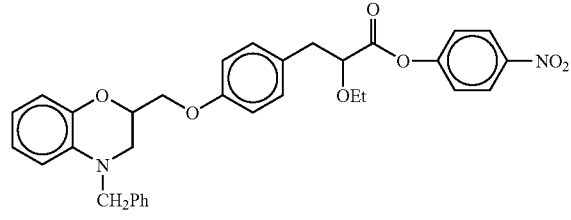

The title compound (0.6 g, 100%) was prepared as a dark brown liquid from (±) 3-[4-(4-benzyl-3,4-dihydro-1,4-benzoxazin-2-yl)methoxyphenyl]-2-ethoxy propanoic acid (0.5 g, 1.34 mmol) obtained in example 62 and 4-nitro phenol by a procedure analogous to that described in example 32.

¹H NMR (CDCl₃, 200 MHz): δ 1.25 (t, J=7.00 Hz, 3H), 3.14 (d, J=6.60 Hz, 2H), 3.33-3.55 (complex, 3H), 3.69-3.77 (complex, 1H), 4.05-4.31 (complex, 3H), 4.46 (d, J=3.40 Hz, 2H), 4.55-4.61 (complex, 1H), 6.63-6.68 (complex, 6H), 7.11-7.28 (complex, 7H), 7.52 (d, J=7.60 Hz, 2H), 8.23 (d, J=9.00 Hz, 2H).

EXAMPLE 65

(−) Ethyl 2-ethoxy-3-[4-[2-(2,3-dihydro-1,4-benzothiazin-4-yl)ethoxy]phenyl]propanoate

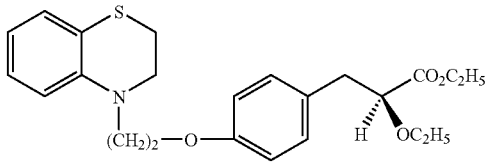

To a stirred solution of (−) ethyl 2-ethoxy-3-(4-hydroxyphenyl)propanoate (0.5 g, 2.1 mmol) in dry N,N-dimethyl formamide (0.8 mL) was added anhydrous potassium carbonate (1.16 g, 8.4 mmol) and stirred at about 25° C. for 20 minutes and mesylate of 2,3-dihydro-1,4-benzothiazin-1-ethanol (0.57 g, 2.1 mmol) in 4 mL of dry DMF was added. The reaction mixture was stirred at ~60° C. for 18 h, cooled to about 25° C. and filtered. The filtrate was diluted with ethylacetate (100 mL) and washed with water (3×100 mL), dried over anhydrous $Na_2SO_4$ and concentrated. The crude compound was chromatographed over silica gel using 10% ethylacetate in pet. ether as eluent to afford the title compound as pale brown colour oil (0.63 g, 70%). $[\alpha]^{25}_D$=−12.5° (c=1.0, $CHCl_3$).

$^1$HNMR ($CDCl_3$): δ 1.10-1.30 (m, 6H), 2.94 (d, J=6.42 Hz, 2H), 3.01-3.10 (m, 2H), 3.28-3.68 (m, 2H), 3.70-3.80 (m, 4H), 3.95 (t, J=6.42 Hz, 1H), 4.10-4.22 (m, 4H), 6.55-6.74 (m, 2H), 6.80 (d, J=8.63 Hz, 2H), 6.98-7.10 (m, 2H), 7.14 (d, J=8.63 Hz, 2H).

EXAMPLE 66

(±) Ethyl 2-ethoxy-3-[4-[2-(2,3-dihydro-1,4-benzothiazin-4-yl)ethoxy]phenyl]propanoate

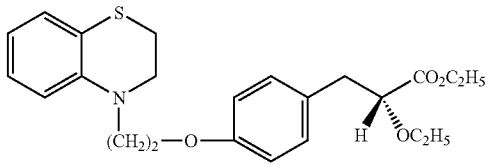

The title compound (0.9 g, 76%) was prepared as pale brown oil from (+) ethyl 2-ethoxy-3-4-hydroxyphenyl)propanoate (0.68 g, 2.8 mmol), mesylate of 2,3-dihydro-1,4-benzothiazin-1-ethanol (0.78 g, 2.8 mmol) and anhydrous $K_2CO_3$ (1.57 g, 11.3 mmol) by a similar procedure to that described in example 65. $[\alpha]^{25}_D$=10.8° (c=1.05, $CHCl_3$).

$^1$HNMR ($CDCl_3$): δ 1.10-1.30 (m, 6H), 2.93 (d, J=6.55 Hz, 2H), 3.00-3.07 (m, 2H), 3.25-3.68 (m, 2H), 3.69-3.80 (m, 4H), 3.96 (t, J=6.55 Hz, 1H), 4.10-4.20 (m, 4H), 6.55-6.75 (m, 2H), 6.80 (d, J=8.30 Hz, 2H), 6.98-7.10 (m, 2H), 7.14 (d, J=8.30 Hz, 2H).

EXAMPLE 67

(−) 2-Ethoxy-3-[4-[2-(2,3-dihydro-1,4-benzothiazin-4-yl)ethoxy]phenyl]propanoic acid

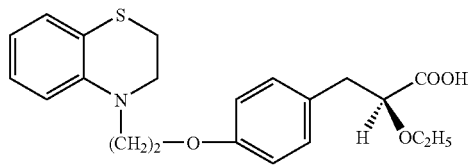

To a stirred methanolic solution of (−)-ethyl 2-ethoxy-3-[4-[2-(2,3-dihydro-1,4-benzothiazin-4-yl)ethoxy]phenyl] propanoate (0.050 g, 0.12 mmol) obtained in example 65, aqueous sodium hydroxide solution (0.050 g in 1 mL of water) was added at about 26° C. for hydrolysis of ester. After 20 minutes methanol was evaporated under reduced pressure below 30° C. (water bath temperature) immediately the residue was diluted with ice cold water (5 mL) and cooled to ~3° C. (ice bath). The contents were acidified with 0.5 N HCl to the pH 7.0 and washed thoroughly with 0.3% ethyl acetate in diethylether (3×10 mL), extracted with ethylacetate (3×10 mL). The extracts were washed with water, brine, dried over anhydrous $Na_2SO_4$ and the solvent was evaporated under reduced pressure below 30° C. to yield the title compound as a colourless sticky mass (0.037 g, 80%). $[\alpha]^{25}_D$=−15.8° (c=1.050, MeOH).

$^1$HNMR ($CDCl_3$): δ 1.17 (t, J=7.01 Hz, 3H), 2.88-3.15 (m, 4H), 3.32-3.68 (m, 2H), 3.70-3.80 (m, 4H), 4.00-4.10 (m, 1H), 4.15 (t, J=5.81 Hz, 2H), 6.53-6.78 (m, 2H), 6.81 (d, J=8.63 Hz, 2H), 6.95-7.10 (m, 2H), 7.15 (d, J=8.63 Hz, 2H).

EXAMPLE 68

(±) 2-ethoxy-3-[4-[2-(2,3-dihydro-1,4-benzothiazin-4-yl)ethoxy]phenyl]propanoic acid

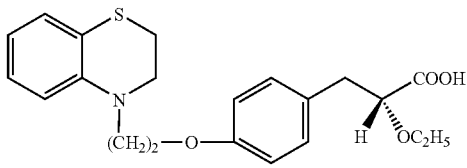

The title compound (0.07 g, 78%) was prepared as off white sticky mass from (+) ethyl 2-ethoxy-3-[4-[2-(2,3-dihydro-1,4-benzothiazin-4-yl)ethoxy]phenyl] propanoate (0.1 g, 0.24 mmol) obtained in example 66 and sodium hydroxide (0.1 g, 2.4 mmol) by a similar procedure to that described in example 67.

$^1$HNMR ($CDCl_3$): δ 1.15 (t, J=6.98 Hz, 3H), 2.87-3.14 (m, 4H), 3.30-3.70 (m, 2H) 3.72-3.82 (m, 4H), 4.00-4.12 (m, 1H), 4.12 (t, J=5.78 Hz, 2H), 6.55-6.70 (m, 2H), 6.81 (d, J=8.62 Hz, 2H), 6.87-7.10 (m, 2H), 7.14 (d, J=8.62 Hz, 2H).

EXAMPLE 69

(±) 3-[4-[2-(2,3-Dihydro-1,4-benzothiazin-4-yl) ethoxy]phenyl]-2-ethoxypropanoic acid, magnesium salt

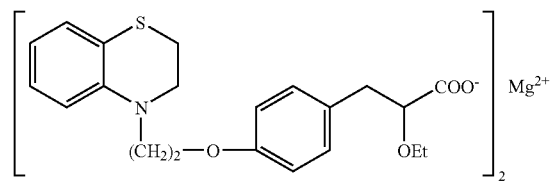

To a solution of (±) 3-[4-[2-(2,3-dihydro-1,4-benzothiazin-4-yl)ethoxy]phenyl]-2-ethoxypropanoic acid (100 mg, 0.258 mmol) obtained in example 29 in methanol (5 mL) was added magnesium hydroxide (7.5 mg, 0.129 mmol) and stirred the reaction mixture at 30° C. for 24 hours and evaporated the solvent, washed the residue with dry diethyl ether to remove unreacted starting material. The white powder was dried at 50° C. under vacuum for 7 hours to yield the title compound as a white powder (90 mg, 88%). mp: 158° C.-160° C.

¹H NMR (d₄ MeOH): δ 1.09 (t, J=7.00 Hz, 3H), 2.78 (dd, J=8.40 and 14.0 Hz, 1H), 2.90-3.05 (m, 3H), 3.15-3.67 (m, 2H), 3.69-3.73 (m, 4H), 3.75-3.90 (m, 1H), 4.14 (t, J=5.40 Hz, 2H), 6.55 (d, J=7.50 Hz, 1H), 6.70-6.82 (m, 3H), 6.90 (d, J=7.50 Hz, 2H), 7.16 (d, J=8.40 Hz, 2H).

EXAMPLE 70

(−) 3-[4-[2-(2,3-Dihydro-1,4-benzothiazin-4-yl)ethoxy]phenyl]-2-ethoxypropanoic acid, sodium salt

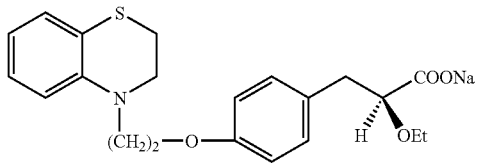

A mixture of (−) 3-[4-[2-(2,3-dihydro-1,4-benzothiazin-4-yl)ethoxy]phenyl]-2-ethoxypropanoic acid (0.2 g, 0.51 mmol) obtained in example 67 and sodium methoxide (0.0279 g, 0.51 mmol) in methanol (4 mL) was stirred at room temperature for 2 hours. Methanol was removed under reduced pressure and residue was triturated with ether (3×10 mL), separated solid was filtered and dried over $P_2O_5$ under vacuum to yield the title compound as an hygroscopic solid (0.105 g, 50%).

¹HNMR (DMSO-d₆): δ 0.92-0.99 (t, J=6.64 Hz, 3H), 2.50-2.77 (m, 3H), 3.02-3.10 (m, 3H), 3.44-3.50 (t, J=8.90 Hz, 1H), 3.55-3.69 (m, 4H), 4.11-4.13 (m, 2H), 6.53-6.57 (d, J=7.05 Hz, 1H), 6.77-6.82 (d, J=8.30 Hz, 2H), 6.90-7.12 (m, 3H), 7.20-7.22 (d, J=4.75 Hz, 2H).

EXAMPLE 71

(−) 3-[4-[2-(2,3-Dihydro-1,4-benzothiazin-4-yl)ethoxy]phenyl]-2-ethoxypropanoic acid, magnesium salt

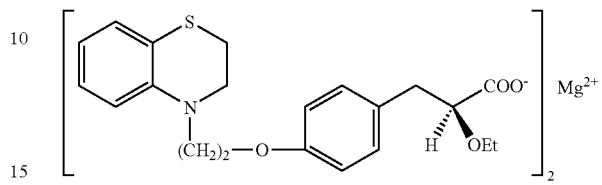

A mixture of (−) 3-[4-[2-(2,3-dihydro-1,4-benzothiazin-4-yl)ethoxy]phenyl]-2-ethoxypropanoic acid (0.320 g, 0.82 mmol) obtained in example 67 and magnesium hydroxide (0.024 g, 0.41 mmol) in methanol (12 mL) was refluxed for 15 h then cooled to room temperature, methanol was removed under reduced pressure separated solid was triturated with pet ether and filtered and dried over $P_2O_5$ to yield the title compound (0.250 g, 73%). mp: 275° C.-285° C. $[\alpha]^{25}$ D=−70.5° (c=1.0, CHCl₃).

¹HNMR (CDCl₃+CD₃OD): δ 1.10 (t, J=7.06 Hz, 3H), 2.81-3.02 (m, 3H), 3.27-3.31 (m, 2H), 3.55-3.79 (m, 5H), 3.81-3.86 (t, J=3.74 Hz, 1H), 4.12-4.17 (t, J=5.49 Hz, 2H), 6.00-6.54 (d, J=7.47 Hz, 1H), 6.79-6.82 (d, J=7.56 Hz, 2H), 6.90-6.94 (m, 3H), 7.14-7.19 (d, J=8.39 Hz, 2H).

EXAMPLE 72

(−) 3-[4-[2-(2,3-Dihydro-1,4-benzothiazin-4-yl)ethoxy]phenyl]-2-ethoxypropanoic acid, arginine salt

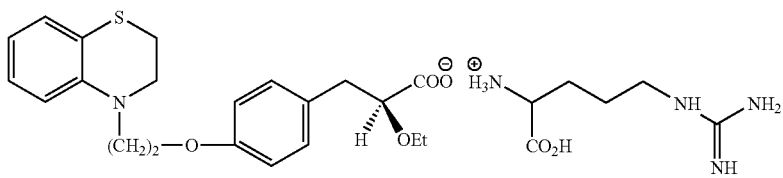

L-Arginine (0.072 g, 0.4 mmol) in water (0.360 mL) was added to a solution of (−) 3-[4-[2-2,3-dihydro-1,4-benzothiazin-4-yl)ethoxy]phenyl]-2-ethoxypropanoic acid (0.180 g, 0.46 mmol) obtained in example 67 in ethanol (4 mL) at 50° C., then cooled to room temperature and stirred for 10 h. Solvent was removed under reduced pressure and traces of water was removed azeotropically by using toluene, separated solid was dried under vacuum to yield the title compound (0.175 g, 99.5%). mp 115° C.-125° C. $[\alpha]25_D$=−13.00° (c=1.0, MeOH).

¹HNMR (CD₃OD): δ 1.05-1.12 (t, J=6.96 Hz, 3H), 1.69-1.85 (m, 4H), 2.79-3.02 (m, 5H), 3.15-3.30 (m, 6H), 3.51-3.60 (q, J=6.73 Hz, 2H), 3.62-3.81 (m, 6H), 4.12-4.18 (t, J=5.49 Hz, 2H), 6.54-6.58 (t, J=7.38 Hz, 1H), 6.78-6.96 (m, 5H), 7.15-7.19 (d, J=8.21 Hz, 2H).

EXAMPLE 73

3-[4-[2-(2,3-Dihydro-1,4-benzoxazin-4-yl)ethoxy]phenyl]-2-ethoxypropanoic acid, arginine salt

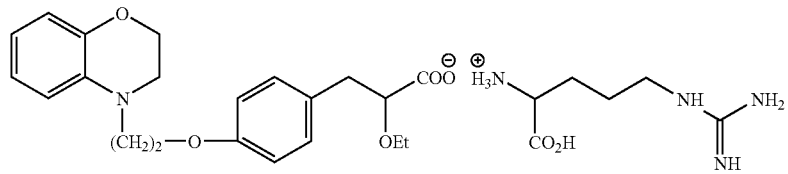

L-Arginine (0.152 g, 0.87 mmol) in water (0.7 mL) was added to a solution of 3-[4-[2-(2,3-dihydro-1,4-benzoxazin-4-yl)ethoxy]phenyl]-2-ethoxypropanoic acid (0.360 g, 0.97 mmol) obtained in example 26 in ethanol (9 mL) at 50° C., then cooled to room temperature and stirred for 10 h. Solvent was removed under reduced pressure and traces of water was removed azeotropically by using toluene, separated solid was dried under vacuum to yield the title compound (0.3 g, 56%). mp: 180° C.-190° C.

$^1$HNMR (CD$_3$OD): δ 0.99-1.12 (t, J=6.92 Hz, 3H), 1.60-1.76 (m, 4H), 2.75 (dd, J=10.0 Hz and 5.4 Hz, 2H), 3.05-3.39 (m, 8H), 3.45-3.74 (m, 10H), 4.05 (t, J=5.40 Hz, 3H), 6.43-6.65 (m, 4H), 6.69 (d, J=8.62 Hz, 2H), 7.06 (d, J=8.62 Hz, 2H).

EXAMPLE 74

(−) Ethyl 2-ethoxy-3-[4-[2-2,3-dihydro-1,4-benzoxazin-4-yl)ethoxy]phenyl]propanoate

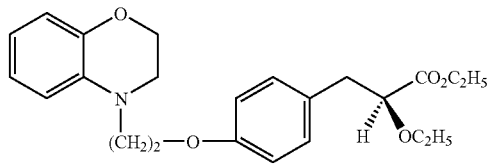

Dry N,N-dimethyl formamide (800 mL) was added to a mixture of 2,3-dihydro-1,4-benzoxazin-1-ethanol methanesulfonate (27.0 g, 0.1.5 mmol), potassium carbonate (58.0 g, 0.420 mmol) and (−) ethyl 2-ethoxy-3-(4-hydroxyphenyl)propanoate (25.0 g, 0.105 mmol) at 25° C. and the contents were heated at 60° C. for 16 h. After the completion of the reaction, the contents were filtered, washed with DMF, diluted with excess water and extracted with ethylacetate. The organic layer was washed thoroughly with water, brine, dried over anhydrous Na$_2$SO$_4$ and concentrated under reduced pressure. The crude compound was chromatographed over silica gel using 5% ethylacetate in pet. ether as eluent to afford the title compound as a brown color liquid (18.2 g, 44%).[α]$^{25}$$_D$=−12.1° (c=1.0, CHCl$_3$).

$^1$HNMR (CDCl$_3$): δ 1.10-1.30 (m, 6H), 2.95 (d, J=6.74 Hz, 2H), 3.20-3.60 (m, 4H), 3.66 (t, J=5.58 Hz, 2H), 3.96 (t, J=6.74 Hz, 1H), 4.10-4.30 (m, 6H), 6.82 (d, J=8.63 Hz, 2H), 6.58-6.90 (m, 4H), 7.15 (d, J=8.63 Hz, 2H).

EXAMPLE 75

(−) 2-Ethoxy-3-[4-[2-(2,3-dihydro-1,4-benzoxazin-4-yl)ethoxy]phenyl]propanoic acid

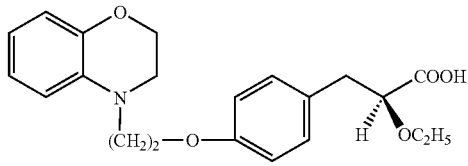

To a solution of (−)-ethyl 2-ethoxy-3-[4-[2-(2,3-dihydro-1,4-benzoxazin-4-yl)ethoxy]phenyl]propanoate (17.0 g, 0.0426 mmol) obtained in example 74, in methanol (500 mL) 10% aqueous sodium hydroxide solution (135 mL) was added to at about 25° C. and stirred for 30 min. Methanol was evaporated under reduced pressure at 20° C. (water bath), the residue was diluted immediately with ice cold water. The aqueous layer was washed with diethyl ether, acidified with 2N HCl, and extracted with ethylacetate. The organic layer was thoroughly washed with water, brine, dried over Na$_2$SO$_4$ and the solvent was evaporated under reduced pressure at 25° C. to yield the title compound as a pale brown thick liquid (14.1 g, 89%). %).[α]$^{25}$$_D$=−18.3° (c=1.0, MeOH).

$^1$HNMR (CDCl$_3$): δ 1.17 (t, J=6.97 Hz, 3H), 2.95 (dd, J=5.99 and 14.11 Hz, 1H), 3.08 (dd, J=4.24 and 14.11 Hz, 1H), 3.30-3.65 (m, 4H), 3.69 (t, J=5.49 Hz, 2H), 4.00-4.10 (m, 1H), 4.12 (t, J=5.49 Hz, 2H), 4.20 (t, J=4.38 Hz, 2H), 6.80 (d, J=8.40 Hz, 2H), 6.55-6.90 (m, 4H), 7.1.5 (d, J=8.40 Hz, 2H).

EXAMPLE 76

(−) 3-[4-[2-(2,3-Dihydro-1,4-benzoxazin-4-yl)ethoxy]phenyl]-2-ethoxypropanoic acid, magnesium salt

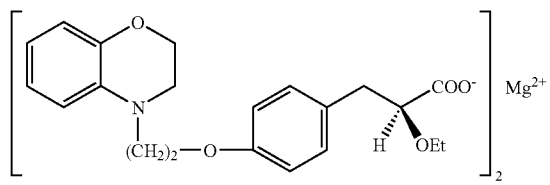

Magnesium hydroxide (1.10 g, 0.0188 mmol) was added to a stirred solution of (−) 3-[4-[2-(2,3-dihydro-1,4-benzothiazin-4-yl)ethoxy]phenyl]-2-ethoxypropanoic acid (14.0 g, 0.0377 mmol) obtained in example 75, in dry methanol (12 mL) under nitrogen atmosphere at 25 C and the contents were refluxed for 18 h. The solvent was evaporated under reduced pressure and the solid was thoroughly triturated with dry diethyl ether and dried under high vacuum at 65° C. (oil bath) for 30 minutes to yield the title compound as a white solid (12.2 g, 83%). mp: 255° C.-260° C. $[\alpha]^{25}_D = -22.3°$ (c=1.0, MeOH: CHCl$_3$ (1:1)).

$^1$HNMR (CDCl$_3$+CD$_3$OD): δ 0.99 (t, J=6.97 Hz, 3H), 2.70 (dd, J=8.40 and 4.12 Hz, 1H), 2.90 (dd, J=4.12 and 14.20 Hz, 1H), 3.10-3.55 (m, 4H), 3.57 (t, J=5.40 Hz, 2H), 3.70-3.80 (m, 1H), 4.00-4.10 (m, 4H), 6.70 (d, J=8.31 Hz, 2H), 6.35-6.80 (m, 4H), 7.07 (d, J=8.31 Hz, 2).

EXAMPLE 77

(−) 3-[4-[2-(2,3-Dihydro-1,4-benzoxazin-4-yl)ethoxy]phenyl]-2-ethoxypropanoic acid, arginine salt

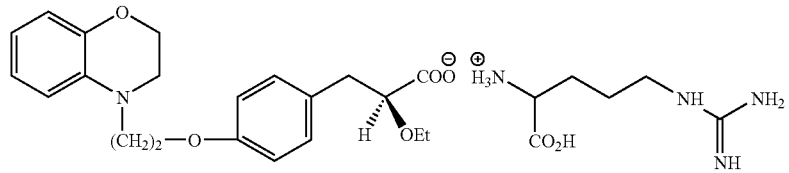

L-Arginine (6.16 g, 0.0354 mmol) in water (20 mL) was added to a stirred solution of (−) 3-[4-[2-(2,3-dihydro-1,4-benzoxazin-4-yl)ethoxy]phenyl]-2-ethoxypropanoic acid (19.6 g, 0.0395 mmol) obtained in example 75 in ethanol (300 mL) at 50° C., then cooled to room temperature and stirred for 15 h. The solvent was removed azeotropically using toluene, separated solid was triturated with dry diethyl ether, filtered and dried under vacuum over CaCl$_2$ overnight to yield the title compound as a white color powder (16.2 g, 76%). mp: 184° C.-186° C. $[\alpha]^{25}_D = -23.4°$ (c=1.0, MeOH).

$^1$HNMR (CD$_3$OD): δ 0.99 (t, J=7.06 Hz, 3H), 1.50-1.85 (m, 4H), 2.68 (dd, J=8.54 Hz and 14.22 Hz, 1H), 2.80 (dd, J=4.35 Hz and 14.22 Hz, 1H), 3.00-3.20 (m, 3H), 3.25-3.48 (m, 4H), 3.56 (t, J=5.39 Hz, 2H), 3.70 (dd, J=4.24, 8.39 Hz, 1H), 4.06 (m, 4H), 6.66 (d, J=8.53 Hz, 2H), 6.75-6.35 (m, 4H), 7.06 (d, J=8.53 Hz, 2H).

The compounds of the present invention lowered random blood sugar level, triglyceride, total cholesterol, LDL, VLDL and increased HDL. This was demonstrated by in vitro as well as in vivo animal experiments.

Demonstration of Efficacy of Compounds

A) In Vitro:

a) Determination of hPPARα Activity

Ligand binding domain of hPPARα was fused to DNA binding domain of Yeast transcription factor GAL4 in eucaryotic expression vector. Using superfect (Qiagen, Germany) as transfecting reagent HEK-293 cells were transfected with this plasmid and a reporter plasmid harboring the luciferase gene driven by a GAL4 specific promoter. Compound was added at different concentrations after 42 hrs of transfection and incubated overnight. Luciferase activity as a function of compound binding/activation capacity of PPARα was measured using Packard Luclite kit (Packard, USA) in Top Count (Ivan Sadowski, Brendan Bell, Peter Broag and Melvyn Hollis. Gene, 1992, 118: 137-141; Superfect Transfection Reagent Handbook. February 1997. Qiagen, Germany).

b) Determination of hPPARγ Activity

Ligand binding domain of hPPARγ1 was fused to DNA binding domain of Yeast transcription factor GAL4 in eucaryotic expression vector. Using lipofectamine (Gibco BRL, USA) as transfecting reagent HEK-293 cells were transfected with this plasmid and a reporter plasmid harboring the luciferase gene driven by a GAL4 specific promoter. Compound was added at 1 μM concentration after 48 hrs of transfection and incubated overnight. Luciferase activity as a function of drug binding/activation capacity of PPARγ1 was measured using Packard Luclite kit (Packard, USA) in Packard Top Count (Ivan Sadowski, Brendan Bell, Peter Broag and Melvyn Hollis. Gene. 1992, 118: 137-141; Guide to Eukaryotic Transfections with Cationic Lipid Reagents. Life Technologies, GIBCO BRL, USA).

c) Determination of HMG CoA Reductase Inhibition Activity

Liver microsome bound reductase was prepared from 2% cholestyramine fed rats at mid-dark cycle. Spectrophotometric assays were carried out in 100 mM KH$_2$PO$_4$, 4 mM DTT, 0.2 mM NADPH, 0.3 mM HMG CoA and 125 μg of liver microsomal enzyme. Total reaction mixture volume was kept as 1 ml. Reaction was started by addition of HMG CoA. Reaction mixture was incubated at 37° C. for 30 min and decrease in absorbance at 340 nm was recorded. Reaction mixture without substrate was used as blank (Goldstein, J. L and Brown, M. S. Progress in understanding the LDL receptor and HMG CoA reductase, two membrane proteins that regulate the plasma cholesterol. J. Lipid Res. 1984, 25: 1450-1461). The test compounds inhibited the HMG CoA reductase enzyme.

B) In Vivo a) Efficacy in Genetic Models

Mutation in colonies of laboratory animals and different sensitivities to dietary regimens have made the development of animal models with non-insulin dependent diabetes and hyperlipidemia associated with obesity and insulin resistance possible. Genetic models such as db/db and ob/ob (Diabetes, (1982) 31(1): 1-6) mice and zucker fa/fa rats have been developed by the various laboratories for understanding the pathophysiology of disease and testing the efficacy of new antidiabetic compounds (Diabetes, (1983) 32: 830-838; Annu. Rep. Sankyo Res. Lab. (1994). 46: 1-57). The homozygous animals, C57 BL/KsJ-db/db mice developed by Jackson Laboratory, U.S., are obese, hyperglycemic, hyperinsulinemic and insulin resistant (J. Clin. Invest., (1990) 85: 962-967), whereas heterozygous are lean and normoglycemic. In db/db model, mouse progressively develops insulinopenia with age, a feature commonly observed in late stages of human type II diabetes when blood sugar levels are insufficiently controlled. The state of pancreas and its course vary according to the models. Since this model resembles that of type II diabetes mellitus, the compounds of the present invention were tested for blood sugar and triglycerides lowering activities.

Male C57BL/KsJ-db/db mice of 8 to 14 weeks age, having body weight range of 35 to 60 grams, bred at Dr. Reddy's Research Foundation (DRF) animal house, were used in the experiment. The mice were provided with standard feed (National Institute of Nutrition (NIN), Hyderabad, India) and acidified water, ad libitum. The animals having more than 350 mg/dl blood sugar were used for testing. The number of animals in each group was 4.

Test compounds were suspended on 0.25% carboxymethyl cellulose and administered to test group at a dose of 0.1 mg to 30 mg/kg through oral gavage daily for 6 days. The control group received vehicle (dose 10 ml/kg). On 6th day the blood samples were collected one hour after administration of test compounds/vehicle for assessing the biological activity.

The random blood sugar and triglyceride levels were measured by collecting blood (100 µl) through orbital sinus, using heparinised capillary in tubes containing EDTA which was centrifuged to obtain plasma. The plasma glucose and triglyceride levels were measured spectrometrically, by glucose oxidase and glycerol-3-$PO_4$ oxidase/peroxidase enzyme (Dr. Reddy's Lab. Diagnostic Division Kits, Hyderabad, India) methods respectively.

The blood sugar and triglycerides lowering activities of the test compound was calculated according to the formula.

No adverse effects were observed for any of the mentioned compounds of invention in the above test.

| Compound | Dose (mg/kg) | Reduction in Blood Glucose Level (%) | Triglyceride Lowering (%) |
| --- | --- | --- | --- |
| Example 41 | 3 | 53 | 27 |
| Example 50 | 3 | 45 | 23 |
| Example 44 | 10 | 47 | 74 |

The ob/ob mice were obtained at 5 weeks of age from Bomholtgard, Denmark and were used at 8 weeks of age. Zucker fa/fa fatty rats were obtained from IffaC redo, France at 10 weeks of age and were used at 13 weeks of age. The animals were maintained under 12 hour light and dark cycle at 25±1° C. Animals were given standard laboratory chow (NIN, Hyderabad, India) and water, ad libitum (Fujiwara, T., Yoshioka, S., Yoshioka, T., Ushiyama, I and Horikoshi, H. Characterization of new oral antidiabetic agent CS-045. Studies in KK and ob/ob mice and Zucker fatty rats. Diabetes, 1988, 37: 1549-1558).

The test compounds were administered at 0.1 to 30 mg/kg/day dose for 9 days. The control animals received the vehicle (0.25% carboxymethylcellulose, dose 10 ml/kg) through oral gavage.

The blood samples were collected in fed state 1 hour after drug administration on 0 and 9 day of treatment. The blood was collected from the retro-orbital sinus through heparinised capillary in EDTA containing tubes. After centrifugation, plasma sample was separated for triglyceride, glucose, free fatty acid, total cholesterol and insulin estimations. Measurement of plasma triglyceride, glucose, total cholesterol were done using commercial kits (Dr. Reddy's Laboratory, Diagnostic Division, India). The plasma free fatty acid was measured using a commercial kit from Boehringer Mannheim, Germany. The plasma insulin was measured using a RIA kit (BARC, India). The reduction of various parameters examined are calculated according to the formula given below.

In ob/ob mice oral glucose tolerance test was performed after 9 days treatment. Mice were fasted for 5 hrs and challenged with 3 gm/kg of glucose orally. The blood samples were collected at 0, 15, 30, 60 and 120 min for estimation of plasma glucose levels.

The experimental results from the db/db mice, ob/ob mice, Zucker fa/fa rats suggest that the novel compounds of the present invention also possess therapeutic utility as a prophylactic or regular treatment for diabetes, obesity, cardiovascular disorders such as hypertension, hyperlipidaemia and other diseases; as it is known from the literature that such diseases are interrelated to each other.

Blood glucose level and triglycerides are also lowered at doses greater than 10 mg/kg. Normally, the quantum of reduction is dose dependent and plateaus at certain dose.

b) Plasma Triglyceride and Cholesterol Lowering Activity in Hypercholesterolemic Rat Models Male Sprague Dawley rats (NIN stock) were bred in DRF animal house. Animals were maintained under 12 hour light and dark cycle at 25±1° C. Rats of 180-200 gram oody weight range were used for the experiment. Animals were made hypercholesterolemic by feeding 2% cholesterol and 1% sodium cholate mixed with standard laboratory chow [National Institute of Nutrition (NIN), Hyderabad, India] for 6 days. Throughout the experimental period the animals were maintained on the same diet (Petit, D., Bonnefis, M. T., Rey, C and Infante, R. Effects of ciprofibrate on liver lipids and lipoprotein synthesis in normo- and hyperlipidemic rats. Atherosclerosis. 1988, 74: 215-225).

The test compounds were administered orally at a dose 0.1 to 30 mg/kg/day for 3 days. Control group was treated with vehicle alone (0.25% Carboxymethylcellulose; dose 10 ml/kg).

The blood samples were collected in fed state 1 hour after drug administration on 0 and 3 day of compound treatment. The blood was collected from the retro-orbital sinus through heparinised capillary in EDTA containing tubes. After centrifugation, plasma sample was separated for total cholesterol, HDL and triglyceride estimations. Measurement of plasma triglyceride, total cholesterol and HDL were done using commercial kits (Dr. Reddy's Laboratory, Diagnostic Division, India). LDL and VLDL cholesterol were calculated from the data obtained for total cholesterol, HDL and triglyceride. The reduction of various parameters examined are calculated according to the formula.

| Example No. | Dose mg/kg | Triglyceride (%) ↓ | Total Cholesterol (%) ↓ | HDL (%) ↑ | LDL (%) ↓ | VLDL (%) ↓ |
| --- | --- | --- | --- | --- | --- | --- |
| Example 27 | 1 | 43 | 57 | 37 | 58 | 79 |
| Example 44 | 1 | 50 | 42 | 46 | 44 | 53 |

↓ reduction; ↑ increase

C) Plasma Triglyceride and Total Cholesterol Lowering Activity in Swiss Albino Mice and Guinea Pigs Male Swiss albino mice (SAM) and male Guinea pigs were obtained from NIN and housed in DRF animal house. All these animals were maintained under 12 hour light and dark cycle at 25±1° C. Animals were given standard laboratory chow (NIN, Hyderabad. India) and water, ad libitum. SAM of 20-25 g body weight range and Guinea pigs of 500-700 g body weight range were used (Oliver, P., Plancke, M. O., Marzin, D., Clavey, V., Sauzieres, J and Fruchart, J.

C. Effects of fenofibrate, gemfibrozil and nicotinic acid on plasma lipoprotein levels in normal and hyperlipidemic mice. Atherosclerosis. 1988, 70: 107-114).

The test compounds were administered orally to Swiss albino mice at 0.3 to 30 mg/kg/day dose for 6 days. Control mice were treated with vehicle (0.25% Carboxymethylcellulose; dose 10 ml/kg). The test compounds were administered orally to Guinea pigs at 0.3 to 30 mg/kg/day dose for 6 days. Control animals were treated with vehicle (0.25% Carboxymethylcellulose; dose 5 ml/kg).

The blood samples were collected in fed state 1 hour after drug administration on 0 and 6 day of treatment. The blood was collected from the retro-orbital sinus through heparinised capillary in EDTA containing tubes. After centrifugation, plasma sample was separated for triglyceride and total cholesterol (Wieland, O. Methods of Enzymatic analysis. Bergermeyer, H. O., Ed., 1963. 211-214; Trinder, P. Ann. Clin. Biochem. 1969, 6: 24-27). Measurement of plasma triglyceride, total cholesterol and HDL were done using commercial kits (Dr. Reddy's Diagnostic Division, Hyderabad, India).

| Compound | Dose (mg/kg) | Triglyceride Lowering (%) |
|---|---|---|
| Example 33 | 3 | 55 |
| Example 41 | 10 | 54 |
| Example 43 | 3 | 49 |
| Example 63 | 3 | 57 |

C) Body Weight Reducing Effect in Cholesterol Fed Hamsters:

Male Syrian Hamsters were procured from NW, Hyderabad, India. Animals were housed at DRF animal house under 12 hour light and dark cycle at 25±1° C. with free access to food and water. Animals were maintained with 1% cholesterol containing standard laboratory chow (NIN) from the day of treatment.

The test compounds were administered orally at 1 to 30 mg/kg/day dose for 15 days. Control group animals were treated with vehicle (Mill Q water, dose 10 ml/kg/day). Body weights were measured on every $3^{rd}$ day.

| Example No. | Dose (mg/kg/day) | Body weight Reduction (%) |
|---|---|---|
| Example 27 | 10 | 12 |
| Example 30 | 10 | 18 |

Formulae for Calculation:

1. Percent reduction in Blood sugar/triglycerides/total cholesterol were calculated according to the formula:

$$\text{Percent reduction (\%)} = \left[1 - \frac{TT/OT}{TC/OC}\right] \times 100$$

OC=Zero day control group value

OT=Zero day treated group value

TC=Test day control group value

TT=Test day treated group value

2. LDL and VLDL cholesterol levels were calculated according to the formula:

$$LDL \text{ cholesterol in mg/dl} = \left[\text{Total cholesterol} - HDL \text{ cholesterol} - \frac{\text{Triglyceride}}{5}\right] \text{mg/dl}$$

VLDL cholesterol in mg/dl=[Total cholesterol−HDL cholesterol−LDL cholesterol] mg/dl

The invention claimed is:

1. A compound which is selected from the group consisting of (±) 3-[2-(2,3-dihydro-1,4-benzothiazin-4-yl)methylbenzofuran-5-yl]-2-ethoxypropanoic acid; (+) 3-[2-(2,3-dihydro-1,4-benzothiazin-4-yl)methylbenzofuran-5-yl]-2-ethoxypropanoic acid; (−) 3-[2-(2,3-dihydro-1,4-benzothiazin-4-yl)methylbenzofuran-5-yl]-2-ethoxypropanoic acid; (±) 3-[4-[2-(2,3-dihydro-1,4-benzothiazin-4-yl)ethoxy]phenyl]-2-ethoxypropanoic acid; (+) 3-[4-[2-(2,3-dihydro-1,4-benzothiazin-4-yl)ethoxy]phenyl]-2-ethoxypropanoic acid; (−) 3-[4-[2-(2,3-dihydro-1,4-benzothiazin-4-yl)ethoxy]phenyl]-2-ethoxypropanoic acid; (±) 3-[4-[2-(3-oxo-2H-1,4-benzothiazin-4-yl)ethoxy]phenyl]-2-ethoxypropanoic acid; (+) 3-[4-[2-(3-oxo-2H-1,4-benzothiazin-4-yl)ethoxy]phenyl]-2-ethoxypropanoic acid; (−) 3-[4-[2-(3-oxo-2H-1,4-benzothiazin-4-yl)ethoxy]phenyl]-2-ethoxypropanoic acid; (±) 3-[6-[2-(2,3-dihydro-1,4-benzothiazin-4-yl)ethoxy]naphthyl]-2-ethoxypropanoic acid; (+) 3-[6-[2-(2,3-dihydro-1, 4-benzothiazin-4-yl)ethoxy]naphthyl]-2-ethoxypropanoic acid; (−) 3-[6-[2-(2,3-dihydro-1,4-benzothiazin-4-yl)ethoxy]naphthyl]-2-ethoxypropanoic acid; (±) 3-[4-[2-(2,3-dihydro-1,4-benzothiazin-4-yl)ethoxy]phenyl]-2-hydroxypropanoic acid; (+) 3-[4-[2-(2,3-dihydro-1,4-benzothiazin-4-yl)ethoxy]phenyl]-2-hydroxypropanoic acid; (−) 3-[4-[2-(2,3-dihydro-1,4-benzothiazin-4-yl)ethoxy]phenyl]-2-hydroxypropanoic acid; (±) 3-[4-[2-(2,3-dihydro-1,4-benzothiazin-4-yl)ethoxy]phenyl]-2-phenoxypropanoic acid; (+) 3-[4-[2-(2,3-dihydro-1,4-benzothiazin-4-yl)ethoxy] phenyl]-2-phenoxypropanoic acid; (−)3-[4-[2-(2,3-dihydro-1,4-benzothiazin-4-yl)ethoxy]phenyl]-2-phenoxypropanoic acid; (±) 2-methyl-3-[4-[2-(2,3-dihydro-1,4-benzothiazin-4-yl)ethoxy]phenyl]-2-phenoxy propanoic acid; (+) 2-methyl-3-[4-[2-(2,3-dihydro-1,4-benzothiazin-4-yl)ethoxy]phenyl]-2-phenoxy propanoic acid; (−) 2-methyl-3-[4-[2-(2,3-dihydro-1,4-benzothiazin-4-yl)ethoxy]phenyl]-2-phenoxy propanoic acid; and the pharmaceutically acceptable salts thereof.

2. A compound which is selected from the group consisting of (±) 3-[4-[2-(2,3-dihydro-1,4-benzothiazin-4-yl)ethoxy]phenyl]-2-ethoxypropanoic acid; (+) 3-[4-[2-(2,3-dihydro-1,4-benzothiazin-4-yl)ethoxy]phenyl]-2-ethoxypropanoic acid; (−) 3-[4-[2-(2,3-dihydro-1,4-benzothiazin-4-yl)ethoxy]phenyl]-2-ethoxypropanoic acid; (±) 3-[4-[2-(3-oxo-2H-1,4-benzothiazin-4-yl) ethoxy]phenyl]-2-ethoxypropanoic acid; (+) 3-[4-[2-(3-oxo-2H-1,4-benzothiazin-4-yl)ethoxy]phenyl]-2-ethoxypropanoic acid; (−) 3-[4-[2-(3-oxo-2H-1,4-benzothiazin-4-yl)ethoxy]phenyl]-2-ethoxypropanoic acid; (±) 3-[4-[2-(2,3-dihydro-1,4-benzothiazin-4-yl)ethoxy]phenyl]-2-hydroxypropanoic acid; (+) 3-[4-[2-(2,3-dihydro-1,4-benzothiazin-4-yl)ethoxy]phenyl]-2-hydroxypropanoic acid; (−) 3-[4-[2-(2,3-dihydro-1,4-benzothiazin-4-yl)ethoxy]phenyl]-2-hydroxypropanoic acid; (±) 3-[4-[2-(2,3-dihydro-1,4-benzothiazin-4-yl)ethoxy]phenyl]-2-phenoxypropanoic acid; (+) 3-[4-[2-(2,3-dihydro-1,4-benzothiazin-4-yl)ethoxy]phenyl]-2- phenoxypropanoic acid; (−) 3-[4-[2-(2,3-dihydro-1,4-benzothiazin-4-yl)ethoxy]phenyl]-2-phenoxypropanoic acid; (±) 2-methyl-3-[4-[2-(2,3-dihydro-1,4-benzothiazin-4-yl)ethoxy]phenyl]-2-phenoxy propanoic acid; (+) 2-methyl-3-[4-[2-(2,3-dihydro-1,4-benzothiazin-4-yl)ethoxy]phenyl]-2-phenoxy propanoic acid; (−) 2-methyl-3-[4-[2-(2,3-dihydro-1,4-benzothiazin-4-yl)ethoxy]phenyl]-2-phenoxy propanoic acid; and the pharmaceutically acceptable salts thereof.

3. A compound which is selected from the group consisting of (±) 3-[4-[2-(2, 3-dihydro-1,4-benzothiazin-4-yl)ethoxy]phenyl]-2-ethoxypropanoic acid; (+) 3-[4-[2-(2,3-dihydro-1,4-benzothiazin-4-yl)ethoxy]phenyl]-2-ethoxypropanoic acid; (−) 3-[4-[2-(2,3-dihydro-1,4-benzothiazin-4-yl)ethoxy]phenyl]-2-ethoxypropanoic acid; (±) 3-[4-[2-(3-oxo-2H-1,4-benzothiazin-4-yl)ethoxy]phenyl]-2-ethoxypropanoic acid; (+) 3-[4-[2-(3-oxo-2H-1,4-benzothiazin-4-yl)ethoxy]phenyl]-2-ethoxypropanoic acid; (−) 3-[4-[2-(3-oxo-2H-1,4-benzothiazin-4-yl)ethoxy]phenyl]-2-ethoxypropanoic acid; and the pharmaceutically acceptable salts thereof.

4. The compound according to claim 1, 2, or 3, wherein the pharmaceutically acceptable salt is selected from: Li, Na, K, Ca, Mg, Fe, Cu, Zn, Mn, N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, benzylamine, phenylethylamine, dialkylamine, trialkylamine, thiamine, aminopyrimidine, aminopyridine, purine, spermidine, alkylphenylamine, glycinol, phenyl glycinol, glycine, alanine, valine, leucine, isoleucine, norleucine, tyrosine, cystine, cysteine, methionine, proline, hydroxy proline, histidine, ornithine, lysine, arginine, serine, threonine, phenylalanine, guanidine, substituted guanidine, ammonium, substituted ammonium or aluminum salts.

5. The compound according to claim 4, wherein the pharmaceutically acceptable salt is Na or Mg.

* * * * *